(12) United States Patent
Bae et al.

(10) Patent No.: US 9,200,196 B2
(45) Date of Patent: Dec. 1, 2015

(54) CHRYSENE DERIVATIVES AND ORGANIC ELECTRICAL DEVICE USING THE SAME

(75) Inventors: Jae-Soon Bae, Daejeon (KR); Jeung-Gon Kim, Daejeon (KR); Ji-Eun Kim, Daejeon (KR); Hye-Young Jang, Daejeon (KR); Jun-Gi Jang, Daejeon (KR); Sang-Young Jeon, Daejeon (KR)

(73) Assignee: LG CHEM, LTD., Seoul (KR)

( * ) Notice: Subject to any disclaimer, the term of this patent is extended or adjusted under 35 U.S.C. 154(b) by 484 days.

(21) Appl. No.: 13/129,768

(22) PCT Filed: Nov. 18, 2009

(86) PCT No.: PCT/KR2009/006779
§ 371 (c)(1),
(2), (4) Date: May 17, 2011

(87) PCT Pub. No.: WO2010/058946
PCT Pub. Date: May 27, 2010

(65) Prior Publication Data
US 2011/0227053 A1 Sep. 22, 2011

(30) Foreign Application Priority Data
Nov. 18, 2008 (KR) ........................ 10-2008-0114661

(51) Int. Cl.
*H01L 51/54* (2006.01)
*H01L 51/46* (2006.01)
(Continued)

(52) U.S. Cl.
CPC ................ *C09K 11/06* (2013.01); *C07C 15/38* (2013.01); *C07C 211/54* (2013.01); *C07C 211/61* (2013.01); *H01L 51/0054* (2013.01); *C07C 2103/24* (2013.01); *C07C 2103/26* (2013.01); *C07C 2103/48* (2013.01); *C07C 2103/50* (2013.01); *C09K 2211/1011* (2013.01); *C09K 2211/1037* (2013.01); *C09K 2211/1044* (2013.01); *C09K 2211/1092* (2013.01); *H01L 51/006* (2013.01); *H01L 51/008* (2013.01); *H01L 51/5012* (2013.01); *H01L 51/5048* (2013.01);
(Continued)

(58) Field of Classification Search
None
See application file for complete search history.

(56) References Cited

U.S. PATENT DOCUMENTS

2006/0134456 A1    6/2006  Ikeda et al.
2006/0210830 A1*   9/2006  Funahashi et al. ............ 428/690

(Continued)

FOREIGN PATENT DOCUMENTS

JP    2006-052323 A    2/2006
JP    2006-052324 A    2/2006

(Continued)

OTHER PUBLICATIONS

Larock, Richard C. et al., "Synthesis of Polcyclic Aromatic Hydrocarbons by Pd-Catalyzed Annulation of Alkynes", Journal of Organic Chemistry (1997), 62(22), pp. 7536-7537, ISSN: 0022-3263.

(Continued)

*Primary Examiner* — J. L. Yang
(74) *Attorney, Agent, or Firm* — Dentons US LLP

(57) ABSTRACT

The present invention relates to a novel chrysene derivative and an organic electronic device using the same. A chrysene according to the present invention may act as a hole injection, hole transport, electron injection and transport, or light emitting material in an organic light emitting device and an organic electronic device, and in particular, may be used alone as a light emitting host or a dopant.

20 Claims, 2 Drawing Sheets

(51) Int. Cl.
  H01L 51/30 (2006.01)
  C07D 409/04 (2006.01)
  C07C 211/54 (2006.01)
  C07D 209/86 (2006.01)
  C07D 277/22 (2006.01)
  C07D 239/26 (2006.01)
  C07D 333/08 (2006.01)
  C07C 211/61 (2006.01)
  C07D 409/14 (2006.01)
  C07C 13/58 (2006.01)
  C09K 11/06 (2006.01)
  C07C 15/38 (2006.01)
  H01L 51/00 (2006.01)
  H01L 51/50 (2006.01)

(52) U.S. Cl.
  CPC ........... H01L 51/5088 (2013.01); Y02E 10/549 (2013.01)

(56) References Cited

U.S. PATENT DOCUMENTS

2007/0237984 A1    10/2007  Matsuura et al.
2008/0278072 A1*   11/2008  Noh et al. .................... 313/504
2011/0034733 A1    2/2011   Funahashi et al.

FOREIGN PATENT DOCUMENTS

JP    2006-256979 A     9/2006
WO    WO 2007/108666 A1 9/2007
WO    2008120808 A1     10/2008
WO    WO 2008/120808    10/2008

OTHER PUBLICATIONS

Tuanli, Yae et al., "Synthesis of Polycyclic Aromatic Iodides via ICE-Induced Intramolecular Cyclization", Organic Letters (2004), vol. 6, No. 16, pp. 2677-2680, ISSN: 1523-7060.
Hohmann, F. et al, "Alkyne-Carbene Chelate Complexes of Chromium: Arrested Intermediates in the Benzannulation Reaction and Precursors of Densely Functionalized Centrosymmetric Chrysenes", Chem. Eur. J., 1997, vol. 3(6), p. 853-859.
Kind, C., et al. "A Quantum Chemical Study of Racemization Pathways in Substituted Chrysene Derivatives", Chem. Eur. J., 2003, vol. 9(7), p. 1610-1619.
Angew, Chem, Int, Ed, Eng 1., 1992, vol. 31(9), p. 1236-1238.
Yao, T., et al. Syntheses of Polycyclic Aromatic Iodides via ICI-Induced Intramolecular Cyclization, J. Org Chem., Organic Letters., 2004, vol. 6(16), p. 2677-2680.
Yao, T., et al., Synthesis of Polycyclic Aromatics and Heteroaromatics via Electrophilic Cyclization, J. Org Chem., 2005, vol. 70, p. 3511-3517.
Misra, B., et al. Dimethylchrysene Diol Epoxides: Mutagenicity in Salmonella typhimurium, Tumorigenicity in Newborn Mice, and Reactivity with Deoxyadenosine in DNA, Chem. Res. Toxicol., 1992, vol. 5, p. 248-254.
Oros, D.R., et al. "Identification and Emission Rates of Molecular Tracers in Coal Smoke Particulate Matter", Fuel, 2000, vol. 79, p. 515-536.
Bhattacharyya, S.C, "Constituents of Centalla Asiatica Part II Structure of the Triterpene Acids", Journal Indian Chem. Soc., 1956, vol. 33(9), p. 630-634.
Yao, T. et al., "Synthesis of Polycyclic Aromatic Iodides via ICI-Induced Intramolecular Cyclization" Oranic Letters, 2005, vol. 7(24), p. 5453-5456.

* cited by examiner

CHRYSENE DERIVATIVES AND ORGANIC ELECTRICAL DEVICE USING THE SAME

TECHNICAL FIELD

The present invention relates to a novel chrysene derivative and an organic electronic device using the same. This application is a national stage application of PCT/KR2009/006779, filed on Nov. 18, 2009, which claims priority from Korean Patent Application No. 10-2008-0114661 filed on Nov. 18, 2008 in the KIPO, all of which are incorporated herein by reference in their entirety.

BACKGROUND ART

An organic electronic device means a device that requires exchanging of electric charges between electrodes using holes and/or electrons and organic materials. The organic electronic device may be largely divided into the following categories according to an operation principle. First, there is an electronic device in which an exciton is formed in an organic layer by a photon that flows from an external light source to the device, the exciton is separated into electrons and holes, and the electrons and the holes are transferred to the other electrodes and used as a current source (voltage source). Second, there is an electronic device in which holes and/or electrons are injected into an organic material semiconductor forming an interface in respects to the electrode by applying a voltage or a current to two or more electrodes, and the device is operated by the injected electrons and holes.

As examples of the organic electronic device, there are an organic light emitting device, an organic solar cell, an organic photoconductor (OPC), an organic transistor and the like, and all of them require a hole injection or transport material, an electron injection or transport material or a light emitting material in order to drive the device.

Hereinafter, an organic light emitting device will be mainly described in detail. However, in the organic electronic devices, all of the hole injection or transport material, an electron injection or transport material or a light emitting material are operated on the basis of the similar principle.

In general, an organic light emitting phenomenon means a phenomenon that converts electric energy into light energy by using an organic material. The organic light emitting device using the organic light emitting phenomenon has a structure which generally comprises an anode, a cathode, and an organic layer that is disposed between them. Herein, most organic layers have a multilayered structure that comprises different materials in order to increase efficiency and stability of the organic light emitting device, and for example, it may comprise a hole injection layer, a hole transport layer, a light emitting layer, an electron transport layer, an electron injection layer and the like. In the organic light emitting device structure, if a voltage is applied between two electrodes, holes are injected from an anode and electrons are injected from a cathode to the organic material layer, and when the injected holes and the electrons meet each other, an exciton is formed, and light is emitted when the exciton falls to a bottom state. It is known that this organic light emitting device has properties such as magnetic light emission, high brightness, high efficiency, low driving voltage, a wide viewing angle, high contrast, high speed response and the like.

In the organic light emitting device, the material that is used in the organic material layer may be classified into a light emitting material and an electric charge material, for example, a hole injection material, a hole transport material, an electron transport material, an electron injection material according to a function thereof. The light emitting material may be classified into a high molecule type and a low molecule type according to the molecular weight, and a fluorescent material and a phosphorescent material according to a mechanism of light emission. In addition, the light emitting material may be classified into blue, green, and red light emitting materials and yellow and orange light emitting materials in order to realize better natural colors according to the emission color.

Meanwhile, in the case of when only one material is used as a light emitting material, by interaction between molecules, there are problems in that the maximum light emitting wavelength moves to the long wavelength, the color purity is lowered, or efficiency of the device is lowered because of reduced effect of light emission. Therefore, in order to increase color purity and increase emission efficiency through transferring of energy, a host/dopant system may be used as the light emitting material. The principle is that if a small amount of dopant that has a smaller energy band gap than a host forming the light emitting layer is mixed with the light emitting layer, the exciton that is generated from the light emitting layer is transported to the dopant to emit light at high efficiency. At this time, since the wavelength of the host is moved to the wavelength bandwidth of the dopant, a desired wavelength of light may be obtained according to the kind of dopant.

In order to sufficiently show excellent properties of the above organic light emitting device, a material constituting the organic material layer in the device, for example, the hole injection material, the hole transport material, the light emitting material, the electron transport material, the electron injection material and the like should be supported by stable and efficient materials. However, the development of a stable and efficient organic material layer material for organic light emitting devices has not yet been made. Therefore, there is a demand for developing a novel material, and the demand for developing the novel material is similarly applied to the other organic electronic device.

DISCLOSURE

Technical Problem

The present invention has been made to solve the above problems in the related art, and it is an object of the present invention to provide a novel stable and efficient chrysene derivative and an organic electronic device using the same.

Technical Solution

In order to solve the above object, an aspect of the present invention provides a compound that is represented by the following Formula 1.

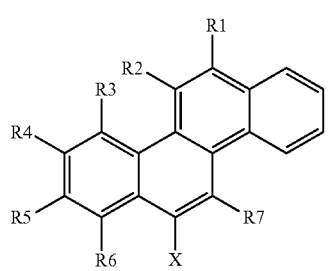

[Formula 1]

wherein

R1 is selected from the group consisting of substituted or unsubstituted $C_1$~$C_{40}$ alkyl group; substituted or unsubstituted $C_3$~$C_{40}$ cycloalkyl group; substituted or unsubstituted $C_2$~$C_{40}$ heterocycloalkyl group; substituted or unsubstituted $C_2$~$C_{40}$ alkenyl group; substituted or unsubstituted $C_1$~$C_{40}$ alkoxy group; substituted or unsubstituted amino group; substituted or unsubstituted $C_6$~$C_{40}$ aryl group; substituted or unsubstituted $C_3$~$C_{40}$ heteroaryl group that comprises O, N, or S as a heteroatom; and substituted or unsubstituted $C_3$~$C_{40}$ heteroarylamine group that comprises O, N, or S as a heteroatom, R2 is selected from the group consisting of substituted or unsubstituted $C_1$~$C_{40}$ alkyl group; substituted or unsubstituted $C_3$~$C_{40}$ cycloalkyl group; substituted or unsubstituted $C_3$~$C_{40}$ heterocycloalkyl group; substituted or unsubstituted $C_2$~$C_{40}$ alkenyl group; substituted or unsubstituted $C_1$~$C_{40}$ alkoxy group; substituted or unsubstituted amino group; substituted or unsubstituted $C_6$~$C_{40}$ aryl group; substituted or unsubstituted $C_3$~$C_{40}$ heteroaryl group that comprises O, N, or S as a heteroatom; substituted or unsubstituted $C_5$~$C_{40}$ arylamine group; and substituted or unsubstituted $C_3$~$C_{40}$ heteroarylamine group that comprises O, N, or S as a heteroatom, R3 to R7 are each independently selected from the group consisting of hydrogen; substituted or unsubstituted $C_1$~$C_{40}$ alkyl group; substituted or unsubstituted $C_3$~$C_{40}$ cycloalkyl group; substituted or unsubstituted $C_2$~$C_{40}$ heterocycloalkyl group that comprises O, N, or S as a heteroatom; substituted or unsubstituted $C_2$~$C_{40}$ alkenyl group; substituted or unsubstituted $C_1$~$C_{40}$ alkoxy group; substituted or unsubstituted amino group; substituted or unsubstituted $C_6$~$C_{40}$ aryl group; substituted or unsubstituted $C_3$~$C_{40}$ heteroaryl group that comprises O, N, or S as a heteroatom; substituted or unsubstituted $C_5$~$C_{40}$ arylamine group; and substituted or unsubstituted $C_3$~$C_{40}$ heteroarylamine group that comprises O, N, or S as a heteroatom, and may form an aliphatic, aromatic, heteroaliphatic or heteroaromatic condensate ring or a spiro bond in conjunction with an adjacent group, X is selected from the group consisting of hydrogen; substituted or unsubstituted $C_1$~$C_{40}$ alkyl group; substituted or unsubstituted $C_3$~$C_{40}$ cycloalkyl group; substituted or unsubstituted $C_2$~$C_{40}$ heterocycloalkyl group that comprises O, N, or S as a heteroatom; substituted or unsubstituted $C_2$~$C_{40}$ alkenyl group; substituted or unsubstituted $C_1$~$C_{40}$ alkoxy group; substituted or unsubstituted amino group; substituted or unsubstituted $C_6$~$C_{40}$ aryl group; substituted or unsubstituted $C_3$~$C_{40}$ heteroaryl group that comprises O, N, or S as a heteroatom; and substituted or unsubstituted $C_3$~$C_{40}$ heteroarylamine group that comprises O, N, or S as a heteroatom, and may form an aliphatic, aromatic, heteroaliphatic or heteroaromatic condensate ring or a spiro bond in conjunction with an adjacent group, and all of R3 to R7, and X are not hydrogen In order to accomplish the above object, a second aspect of the present invention provides an organic electronic device which comprises a first electrode, a second electrode, and one or more organic material layers that are disposed between the first electrode and the second electrode, wherein one or more layers of the organic material layers comprise the compound that is represented by Formula 1.

Advantageous Effects

A compound according to the present invention may act as a hole injection, hole transport, electron injection and transport, or light emitting material in an organic light emitting device and an organic electronic device, and the organic electronic device according to the present invention shows excellent properties in terms of efficiency, a driving voltage, and stability.

BEST MODE

Figure 1:
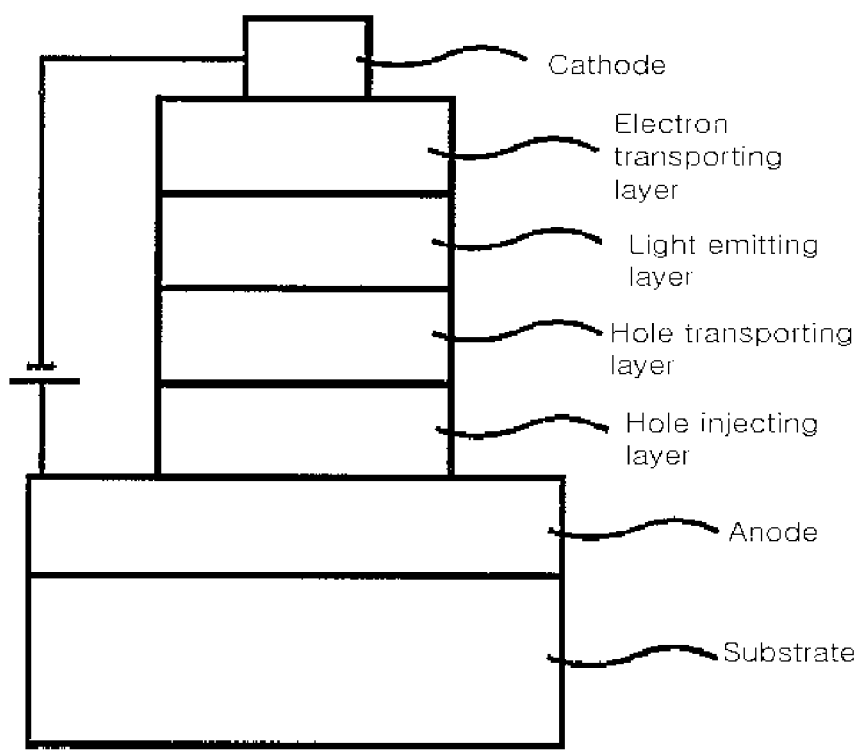
FIG. 1 is a schematic view that illustrates a structure of an organic light emitting device according to an embodiment of the present invention.
Figure 2:
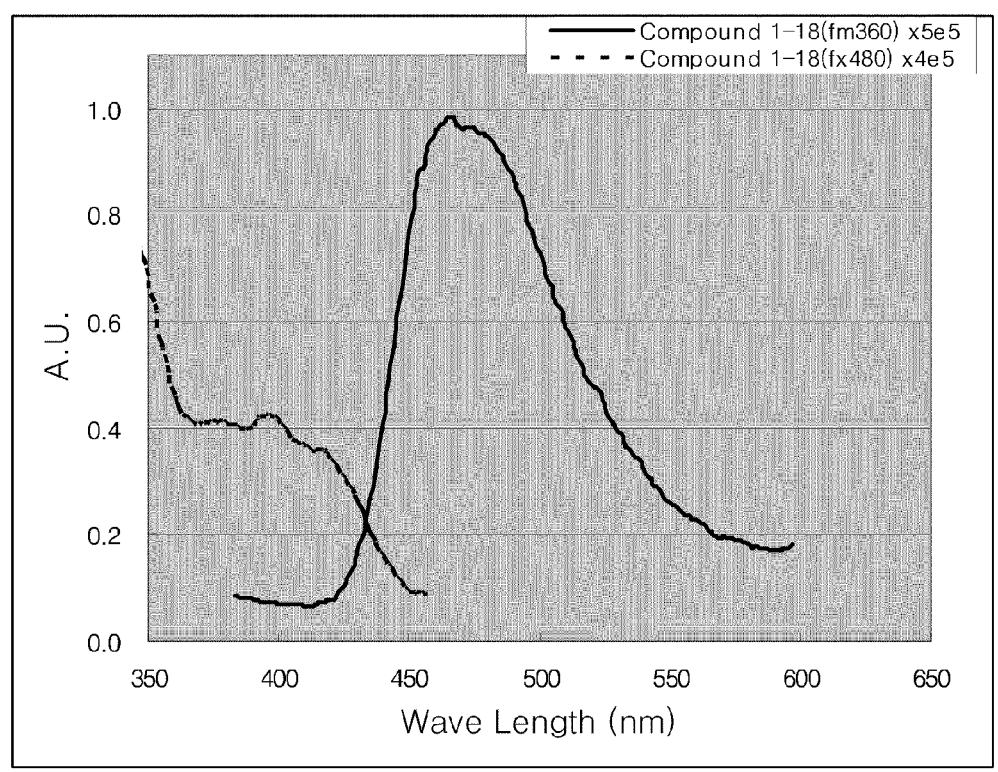
FIG. 2 is a graph that illustrates an excitation wavelength and a light emission wavelength of the film (200A) of a compound 1-18.

Hereinafter, the present invention will be described in more detail.

An aspect of the present invention relates to a compound that is represented by Formula 1.

The substituent group of Formula 1 will be described in detail below.

In R2 to R7, in the case of when alkyl group, cycloalkyl group, heterocycloalkyl group, alkenyl group, alkoxy group, amino group, aryl group, heteroaryl group, arylamine group and heteroarylamine group are substituted by the other functional group, they are substituted by one or more groups that are selected from the group consisting of halogen, deuterium, amino group, nitrile group, nitro group, $C_1$~$C_{40}$ alkyl group, $C_2$~$C_{40}$ alkenyl group, $C_1$~$C_{40}$ alkoxy group, $C_3$~$C_{40}$ cycloalkyl group, $C_2$~$C_{40}$ heterocycloalkyl group that comprises O, N or S as a heteroatom, $C_6$~$C_{40}$ aryl group and $C_3$~$C_{40}$ heteroaryl group that comprises O, N or S as a heteroatom, in R1 and X, in the case of when alkyl group, cycloalkyl group, heterocycloalkyl group, alkenyl group, alkoxy group, amino group, aryl group, heteroaryl group and heteroarylamine group are substituted by the other functional group, they are substituted by one or more groups that are selected from the group consisting of halogen, deuterium, nitrile group, nitro group, $C_1$~$C_{40}$ alkyl group, $C_2$~$C_{40}$ alkenyl group, $C_1$~$C_{40}$ alkoxy group, $C_3$~$C_{40}$ cycloalkyl group, $C_2$~$C_{40}$ heterocycloalkyl group that comprises O, N or S as a heteroatom, $C_6$~$C_{40}$ aryl group and $C_3$~$C_{40}$ heteroaryl group that comprises O, N or S as a heteroatom.

In the case of when there is no specific description in Formula 1, the alkyl group and alkoxy group have preferably 1 to 40 carbon atoms and more preferably 1 to 20 carbon atoms. In addition, the alkenyl group has preferably 2 to 40 carbon atoms and more preferably 2 to 20 carbon atoms. In addition, the aryl group has preferably 6 to 40 carbon atoms and more preferably 6 to 20 carbon atoms. In addition, the heteroring group has preferably 4 to 40 carbon atoms and more preferably 4 to 20 carbon atoms. In addition, the aryl amine group has preferably 6 to 60 carbon atoms and more preferably 6 to 24 carbon atoms. In addition, the heteroarylamine group has preferably 4 to 60 carbon atoms and more preferably 4 to 20 carbon atoms.

In the case of when there is no specific description in Formula 1, the term "substituted or unsubstituted" means that it is substituted or unsubstituted by one or more substituent groups that are selected from the group consisting of halogen group, alkyl group, alkenyl group, alkoxy group, aryl group, arylalkyl group, arylalkenyl group, heteroring group, carbazolyl group, fluorenyl group, nitrile group and acetylene group, but they are not limited thereto.

In Formula 1, R1 is selected from the group consisting of substituted or unsubstituted $C_6\sim C_{40}$ aryl group; substituted or unsubstituted $C_3\sim C_{40}$ heteroaryl group that comprises O, N or S as a heteroatom; and substituted or unsubstituted $C_3\sim C_{40}$ heteroarylamine group that comprises O, N or S as a heteroatom, R2 may be selected from the group consisting of substituted or unsubstituted $C_6\sim C_{40}$ aryl group; substituted or unsubstituted $C_3\sim C_{40}$ heteroaryl group that comprises O, N or S as a heteroatom; substituted or unsubstituted $C_5\sim C_{40}$ arylamine group; and substituted or unsubstituted $C_3\sim C_{40}$ heteroarylamine group that comprises O, N or S as a heteroatom.

In addition, R1 is selected from the group consisting of $C_6\sim C_{20}$ aryl group; $C_6\sim C_{40}$ aryl group or $C_6\sim C_{20}$ aryl group that comprises O, N or S as a heteroatom and substituted by $C_3\sim C_{40}$ heteroaryl group; and $C_3\sim C_{20}$ heteroaryl group that is substituted by $C_6\sim C_{20}$ aryl group and comprises O, N or S as a heteroatom, and R2 may be selected from the group consisting of $C_6\sim C_{20}$ aryl group; $C_6\sim C_{20}$ aryl group that is substituted by $C_6\sim C_{40}$ aryl group, $C_3\sim C_{40}$ heteroaryl group that comprises O, N or S as a heteroatom or $C_5\sim C_{40}$ arylamine group; $C_3\sim C_{20}$ heteroaryl group that is substituted by $C_6\sim C_{20}$ aryl group and comprises O, N or S as a heteroatom; and $C_6\sim C_{20}$ arylamine group.

It is preferable that detailed examples of R1 are selected from the group consisting of substituent groups represented by the following Structural Formulas, but they are not limited thereto.

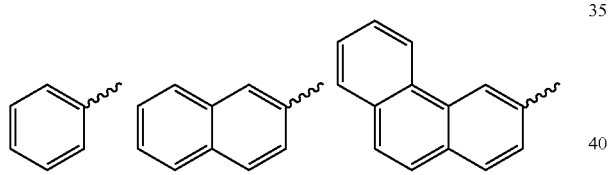

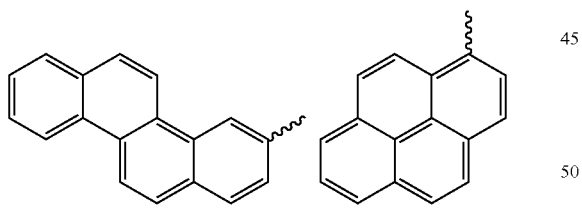

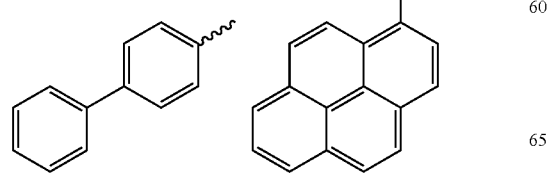

-continued

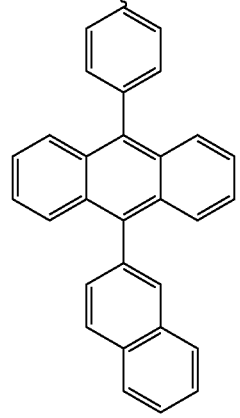

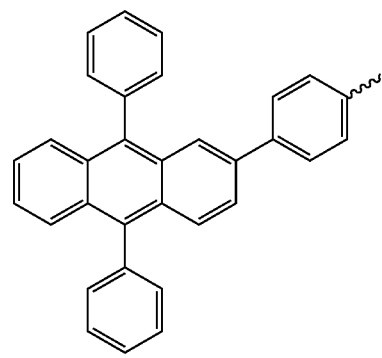

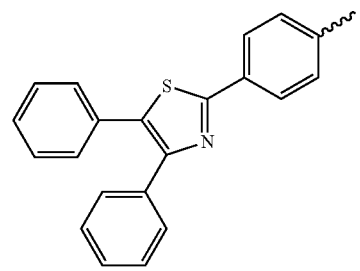

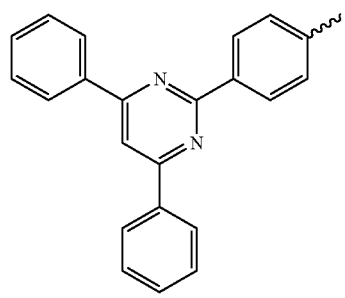

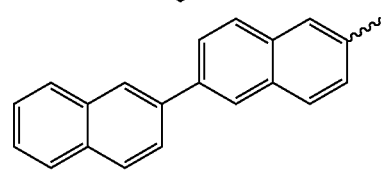

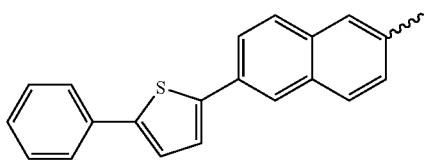

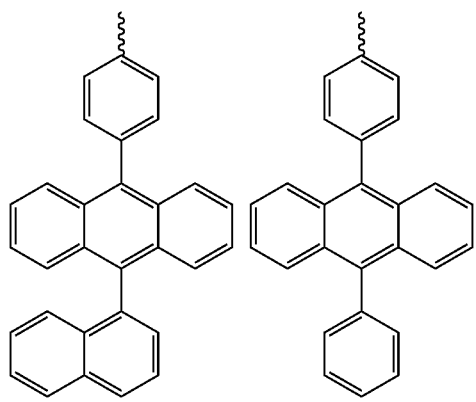
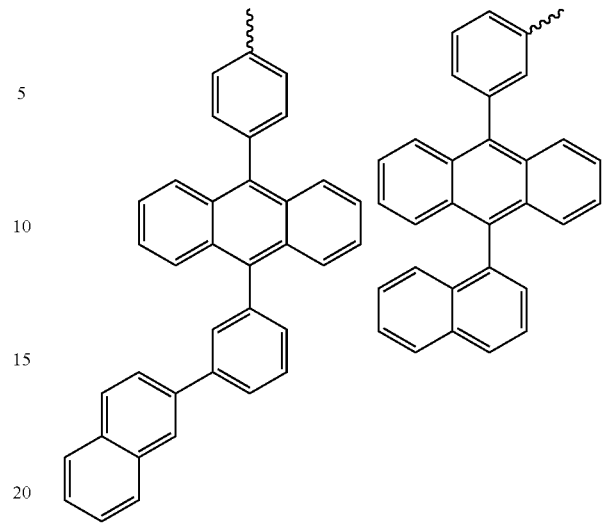
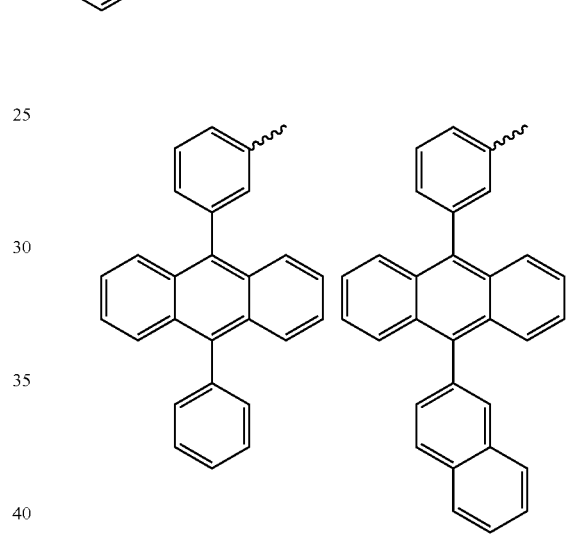
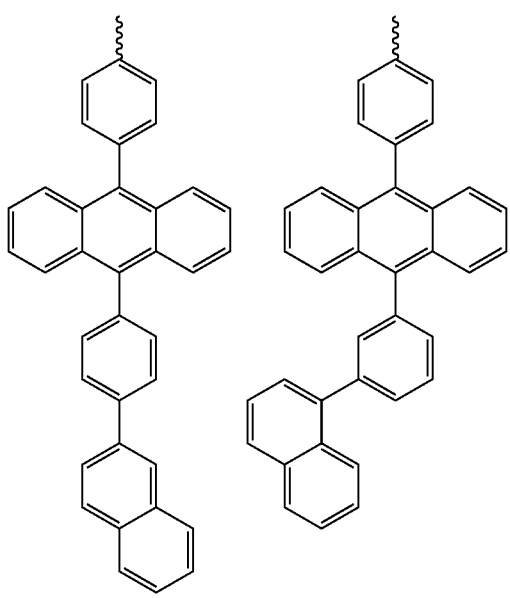
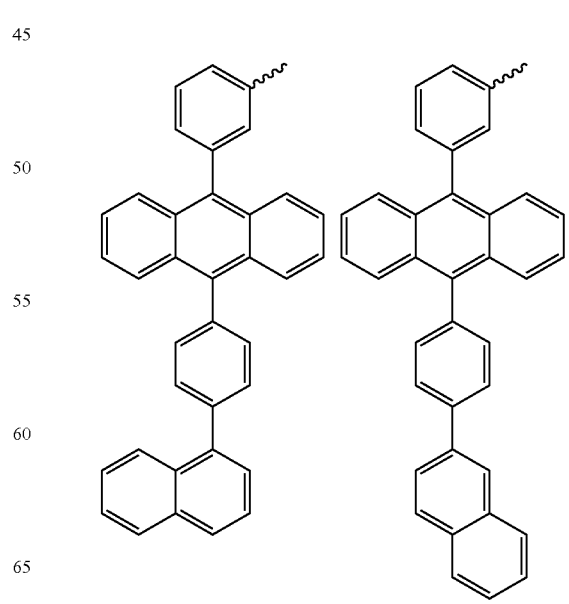

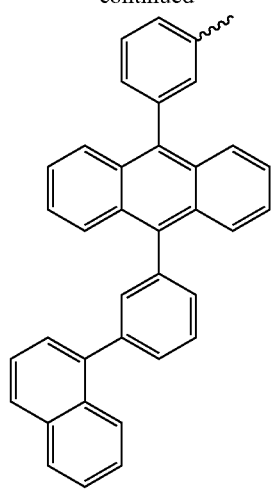
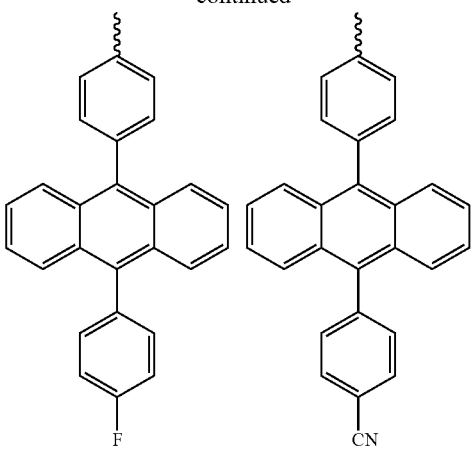

-continued
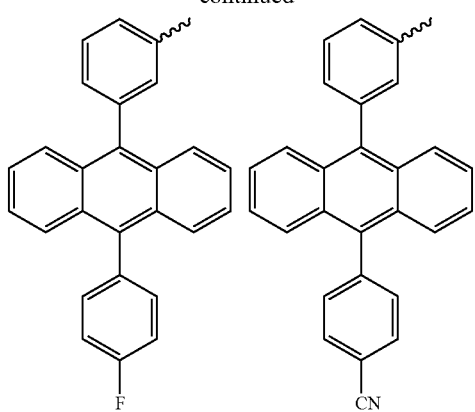
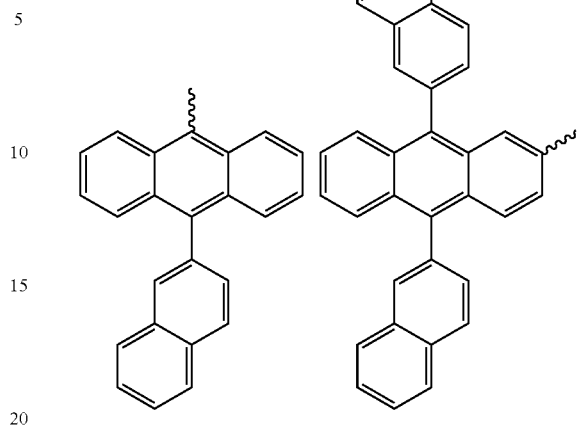
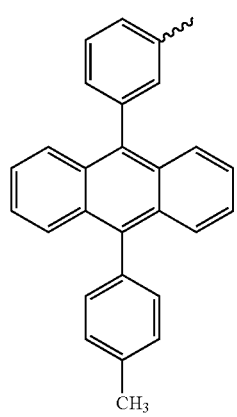
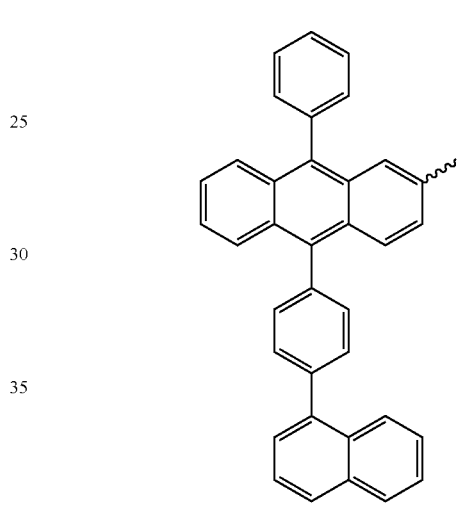
It is preferable that detailed examples of R2 are selected from the group consisting of substituent groups represented by the following Structural Formulas, but they are not limited thereto.
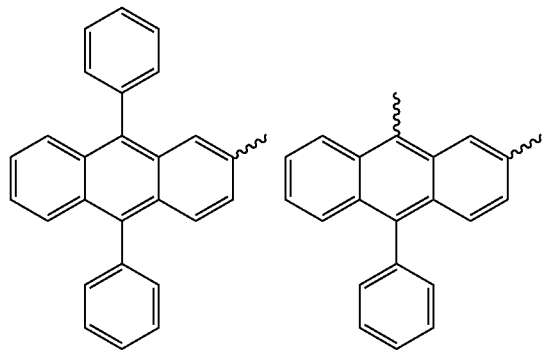
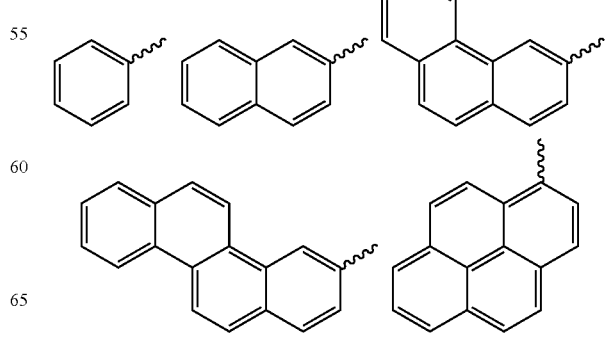

-continued
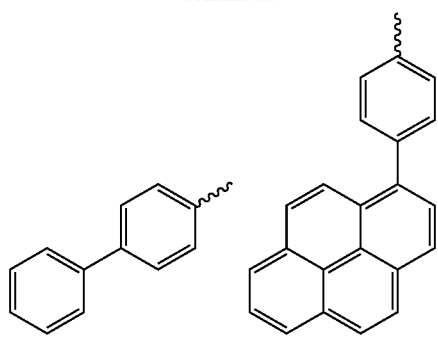
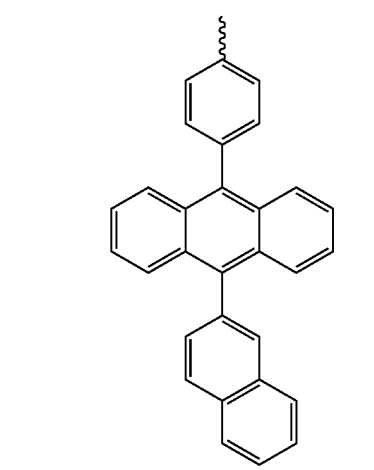
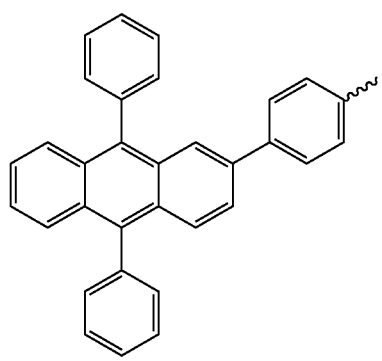
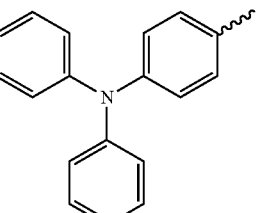
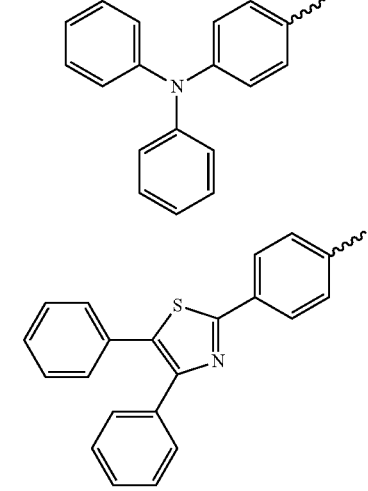
-continued
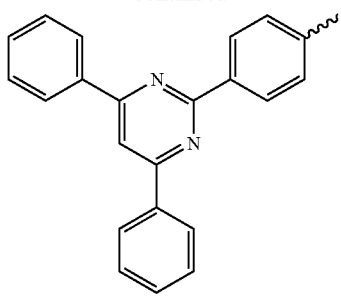
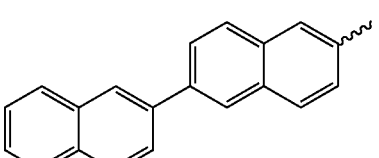
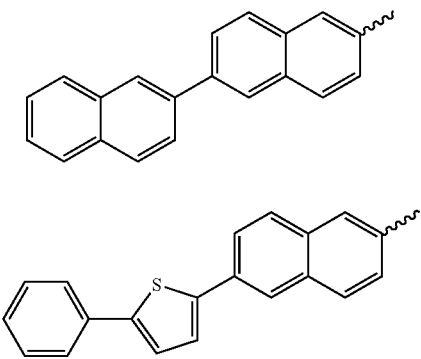
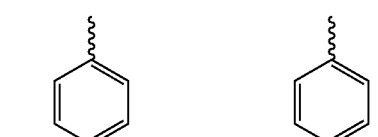
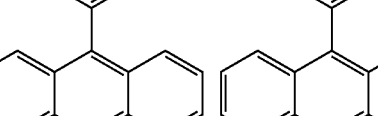

-continued
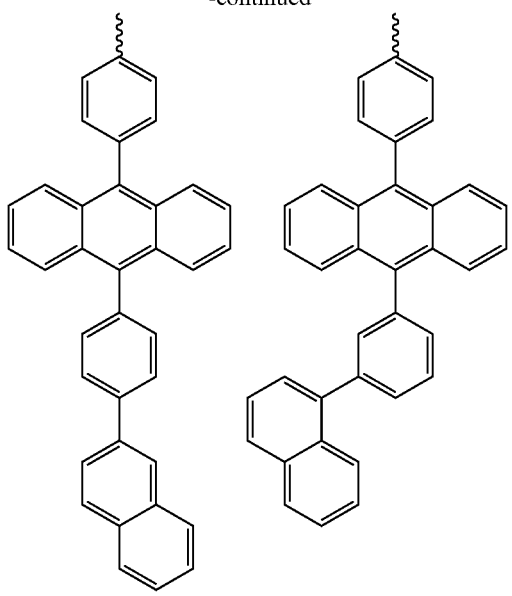
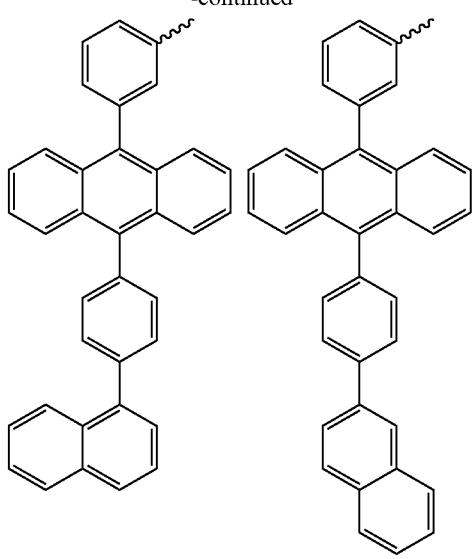
-continued
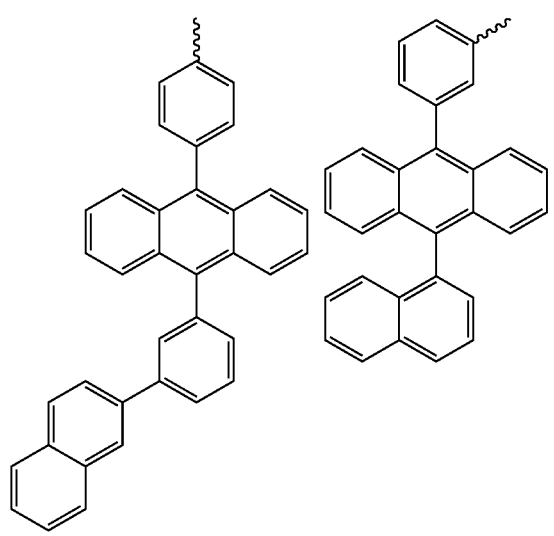
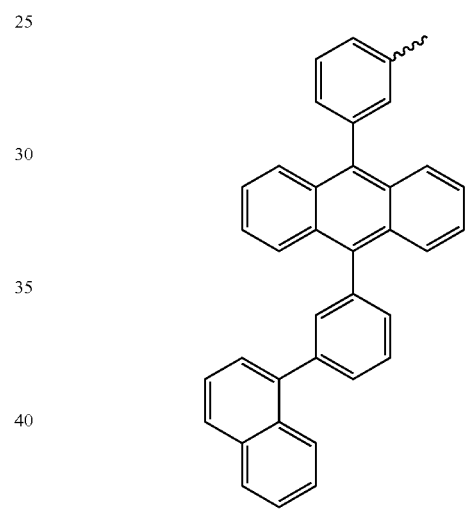
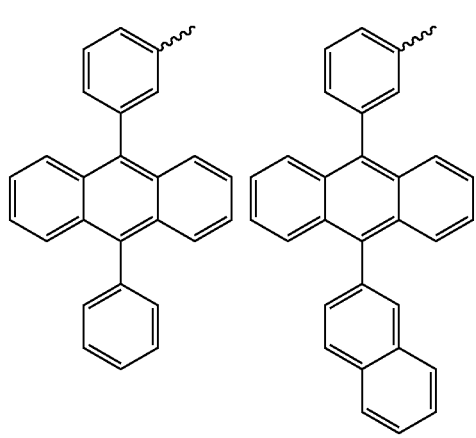
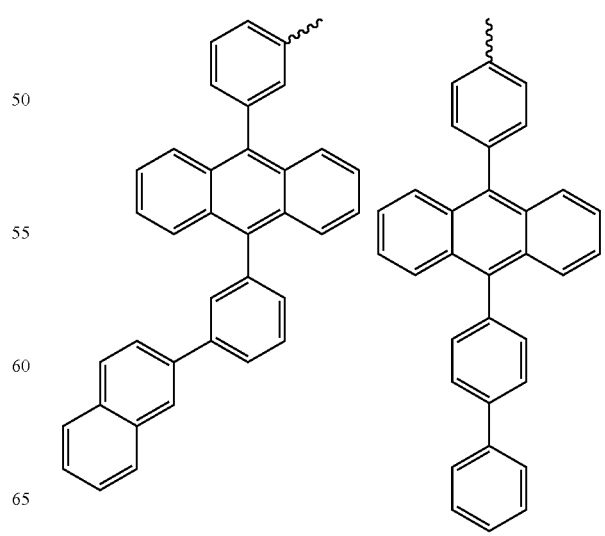

17
-continued
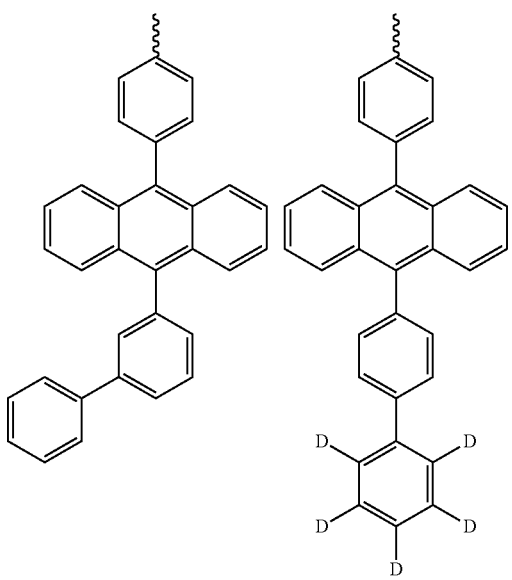
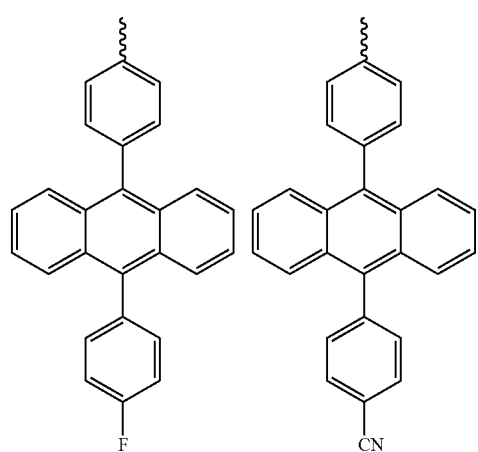
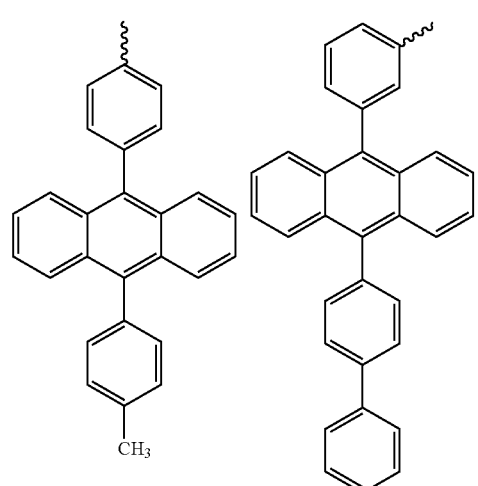
18
-continued
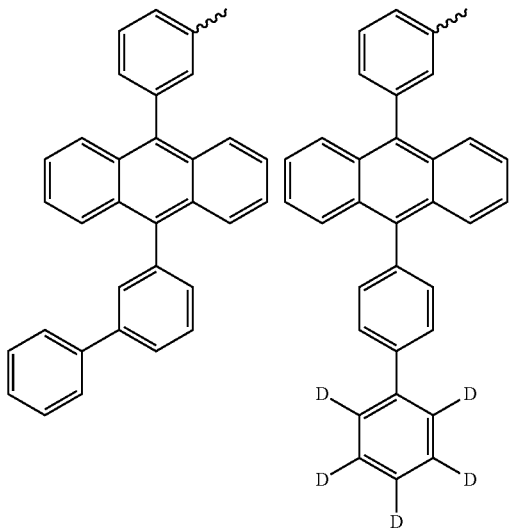
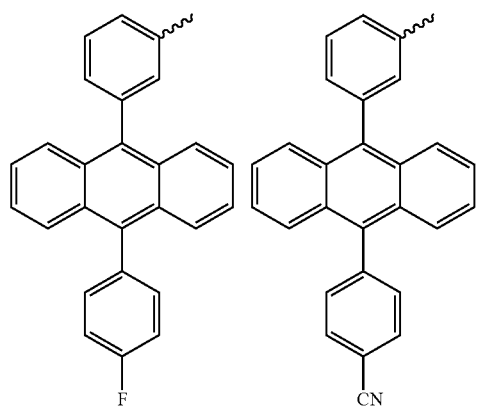
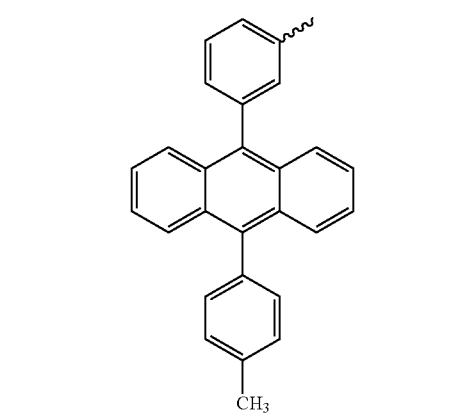
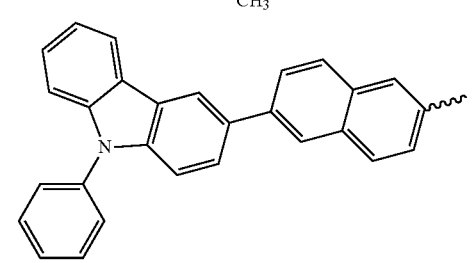

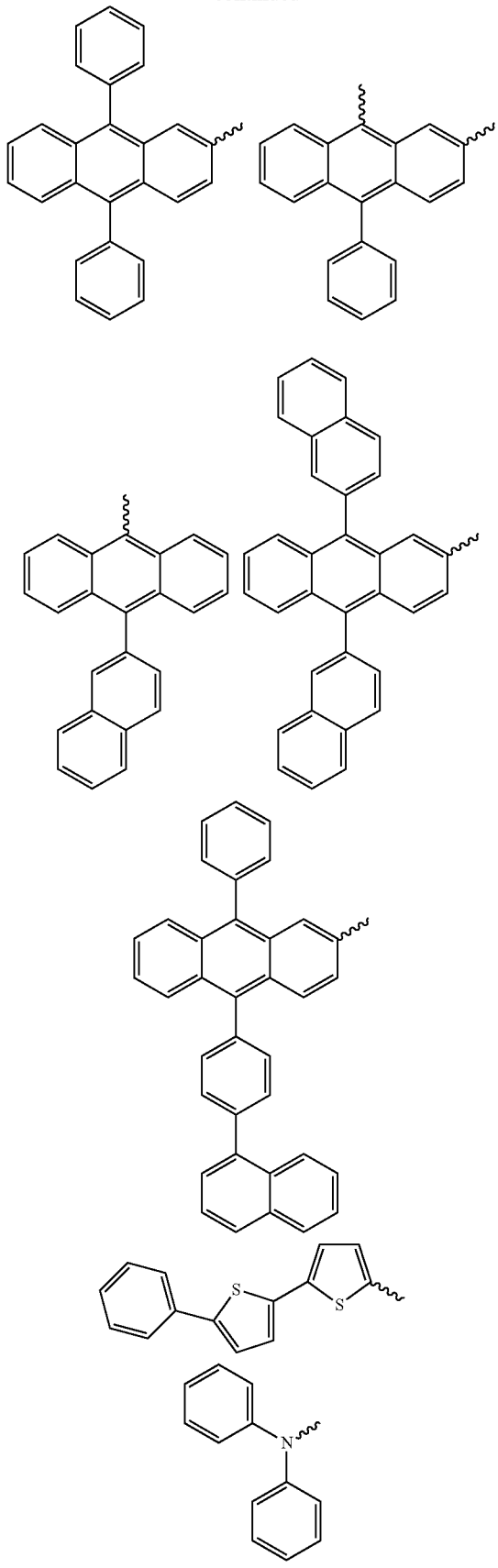

In Formula 1, R3 to R7 may be all hydrogen or four of R3 to R7 and X may be hydrogen.

In the case of when R3 to R7 are all hydrogen, it is preferable that X is selected from the group consisting of substituted or unsubstituted $C_6$~$C_{40}$ aryl group; substituted or unsubstituted $C_3$~$C_{40}$ heteroaryl group that comprises O, N or S as a heteroatom; and substituted or unsubstituted $C_3$~$C_{40}$ heteroarylamine group that comprises O, N or S as a heteroatom.

In addition, in the case of when R3 to R7 are all hydrogen, it is more preferable that X is selected from the group consisting of $C_6$~$C_{20}$ aryl group; $C_6$~$C_{20}$ aryl group that is substituted by $C_6$~$C_{40}$ aryl group, or $C_3$~$C_{40}$ heteroaryl group that comprises O, N or S as a heteroatom; and $C_3$~$C_{20}$ heteroaryl group that is substituted by $C_6$~$C_{20}$ aryl group and comprises O, N or S as a heteroatom.

It is preferable that detailed examples of X are selected from the group consisting of substituent groups represented by the following Structural Formulas, but they are not limited thereto.

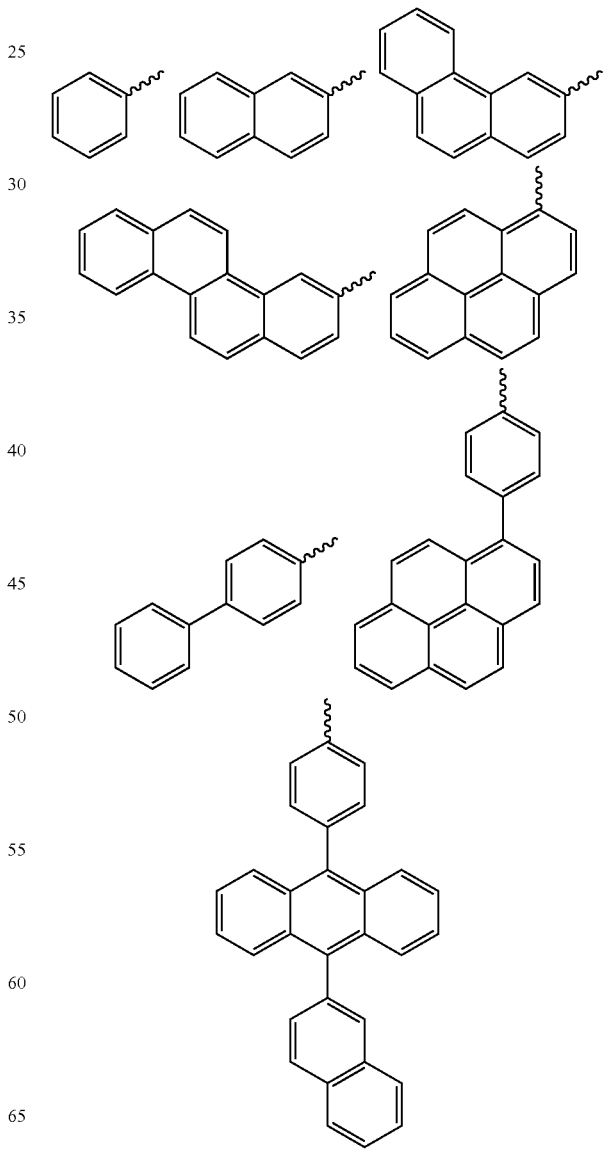

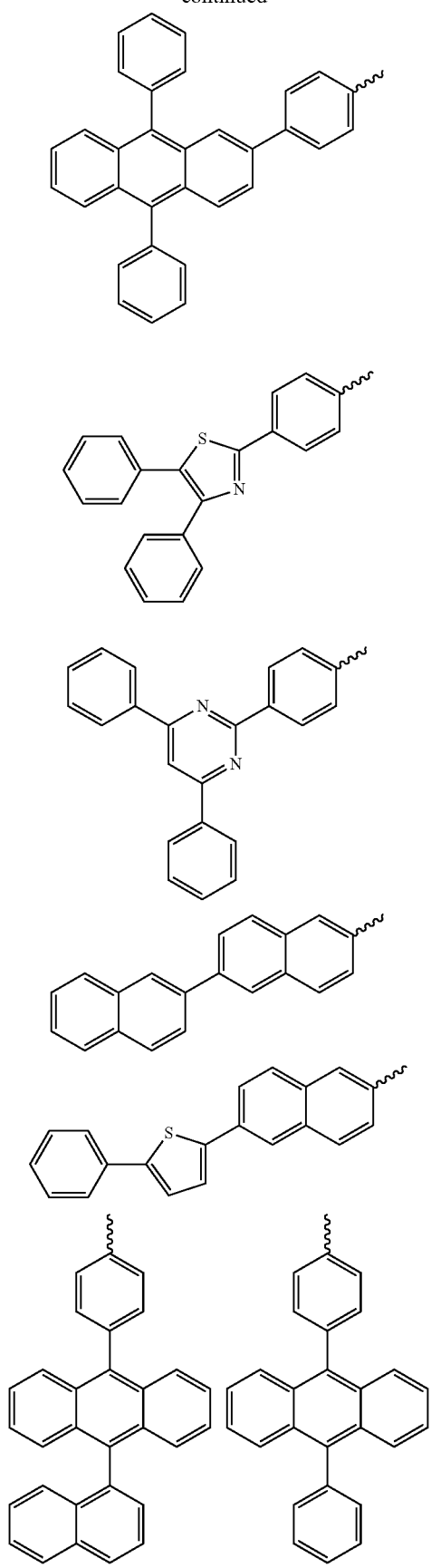
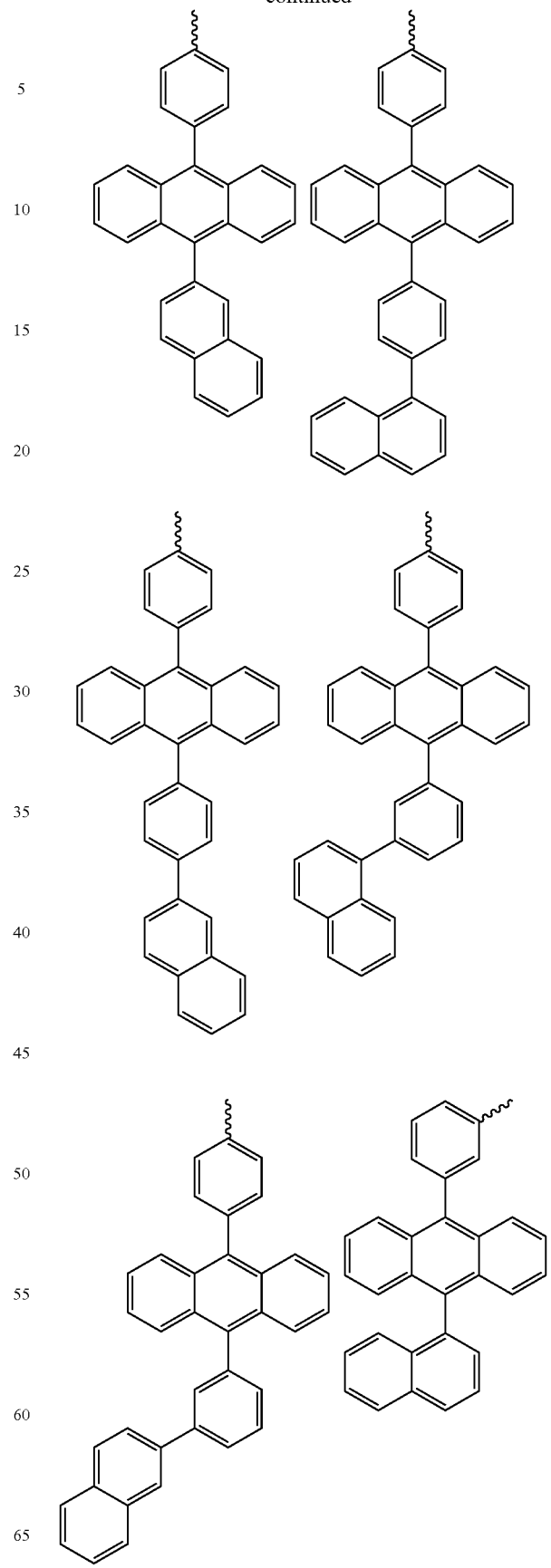

23
-continued
24
-continued
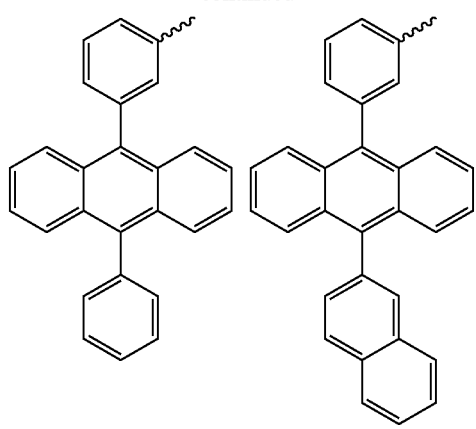
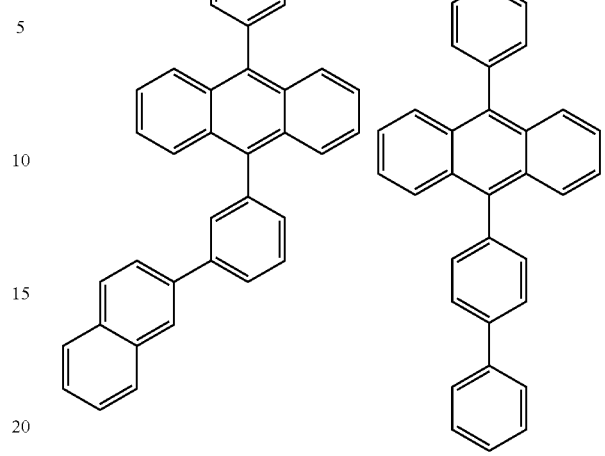
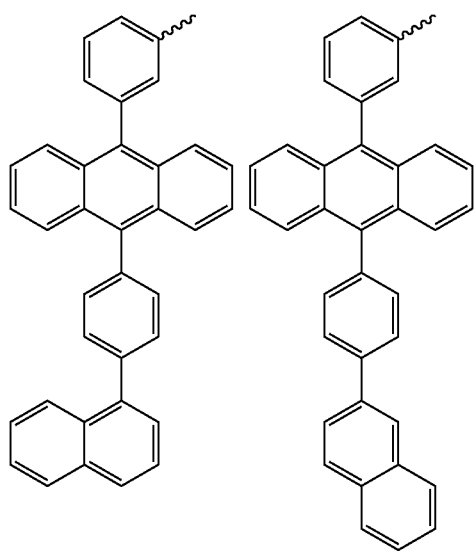
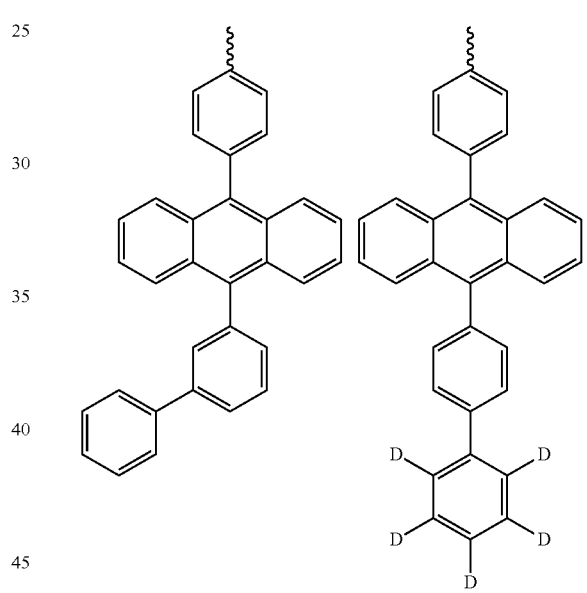
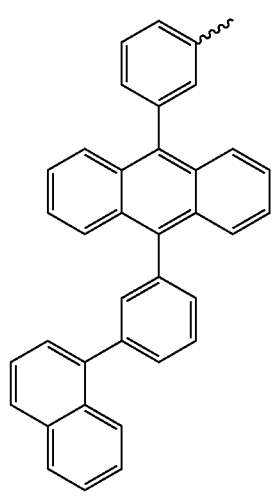
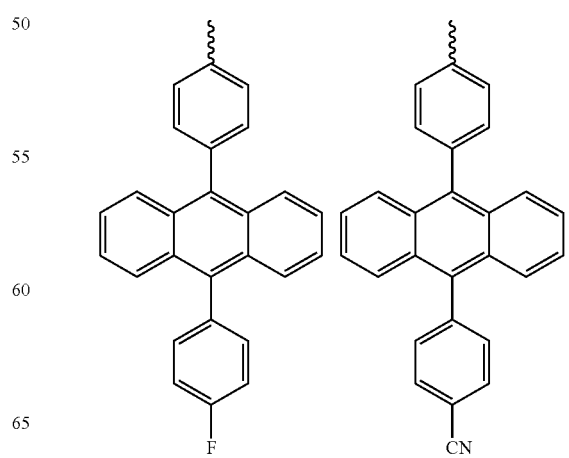

25
-continued
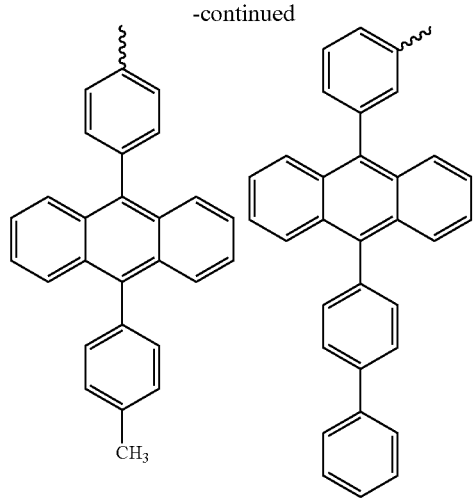
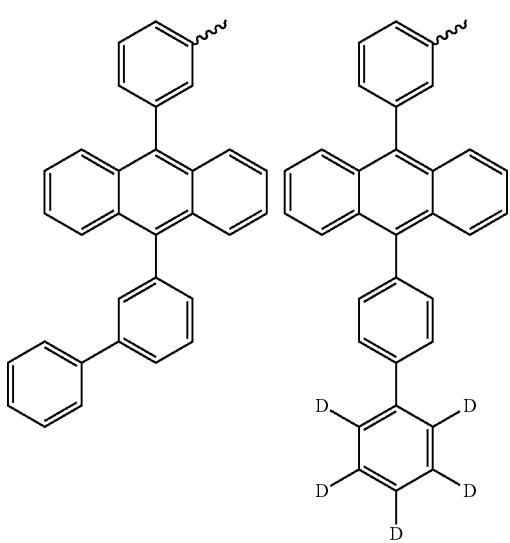
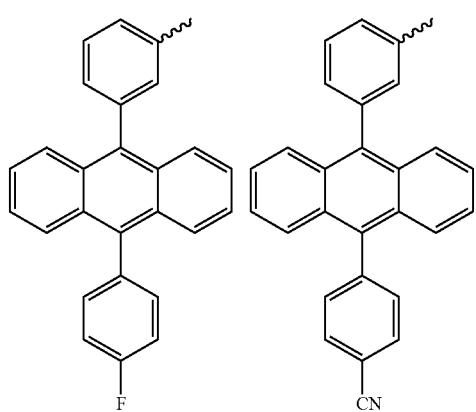
26
-continued
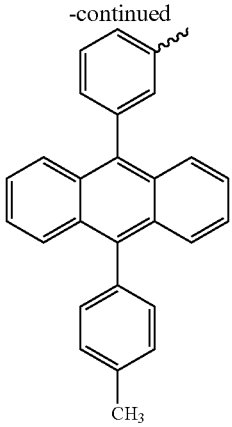
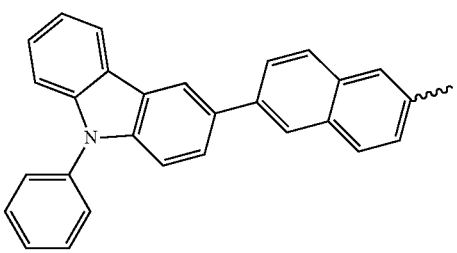
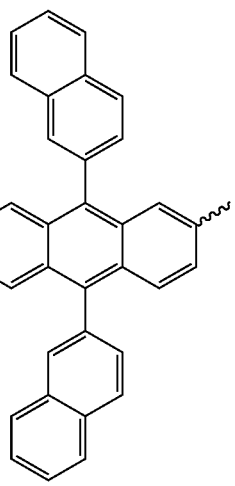

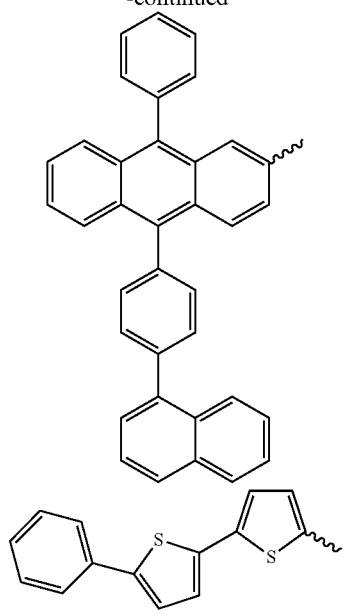

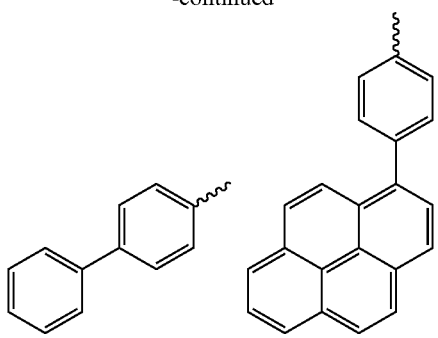

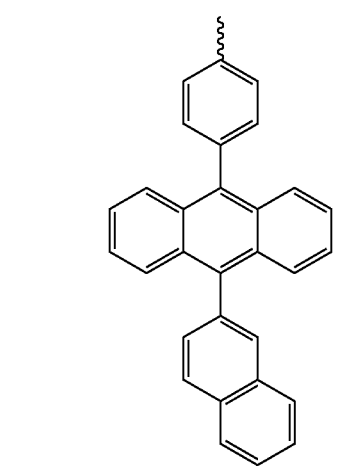

In the case of when four of R3 to R7 and X are hydrogen, it is preferable that the substituent group except for hydrogen among R3 to R7 is selected from the group consisting of substituted or unsubstituted $C_6$~$C_{40}$ aryl group; substituted or unsubstituted $C_3$~$C_{40}$ heteroaryl group that comprises O, N or S as a heteroatom; substituted or unsubstituted $C_5$~$C_{40}$ arylamine group; and substituted or unsubstituted $C_3$~$C_{40}$ heteroarylamine group that comprises O, N or S as a heteroatom.

In addition, in the case of when four of R3 to R7 and X are hydrogen, it is more preferable that the substituent group except for hydrogen among R3 to R7 is selected from the group consisting of $C_6$~$C_{20}$ aryl group; $C_6$~$C_{20}$ aryl group that is substituted by $C_6$~$C_{40}$ aryl group, $C_3$~$C_{40}$ heteroaryl group that comprises O, N or S as a heteroatom or $C_5$~$C_{40}$ arylamine group; $C_3$~$C_{20}$ heteroaryl group that is substituted by $C_6$~$C_{20}$ aryl group and comprises O, N or S as a heteroatom; and $C_6$~$C_{20}$ arylamine group.

In the case of when four of R3 to R7 and X are hydrogen, it is preferable that the substituent group except for hydrogen among R3 to R7 is selected from the group consisting of the substituent groups represented by the following Structural Formulas, but they are not limited thereto.

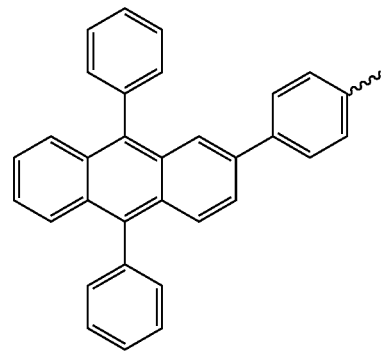

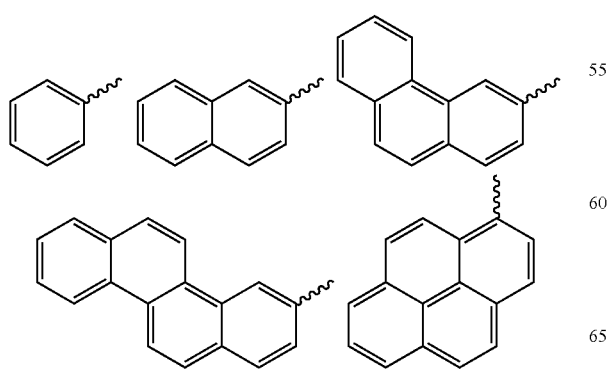

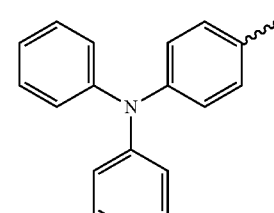

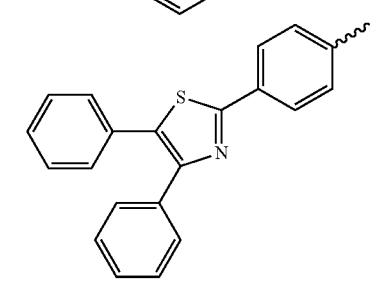

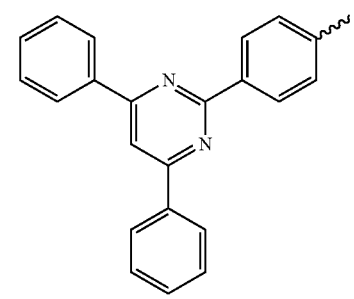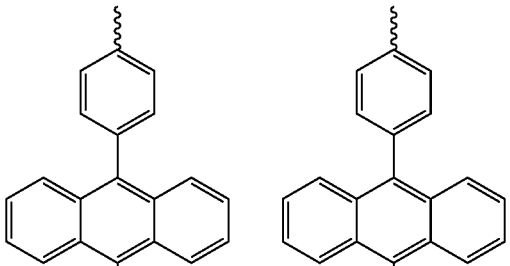

31
-continued
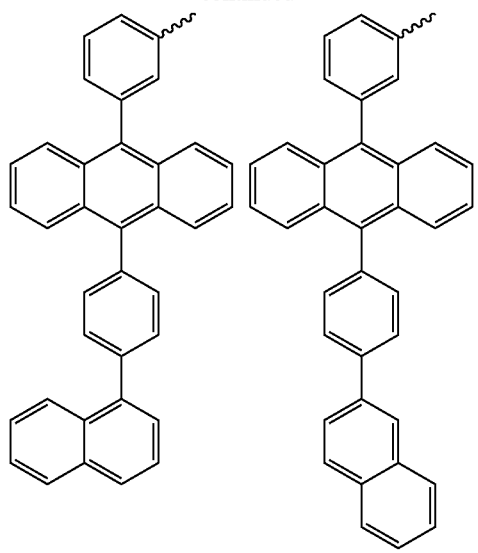
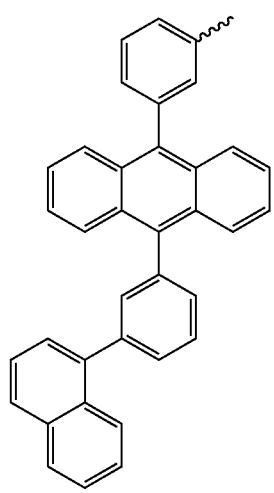
32
-continued
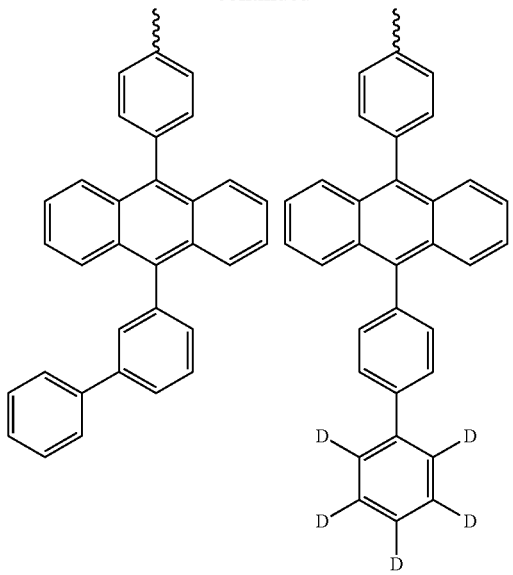
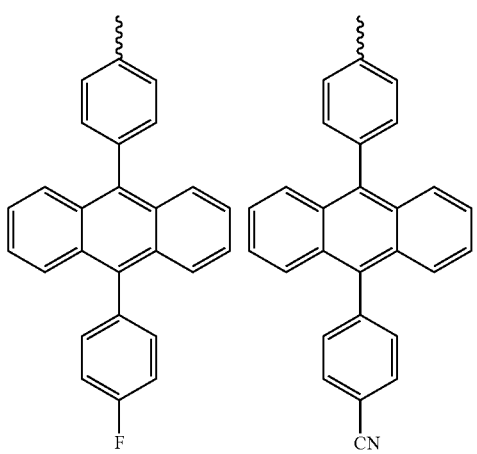
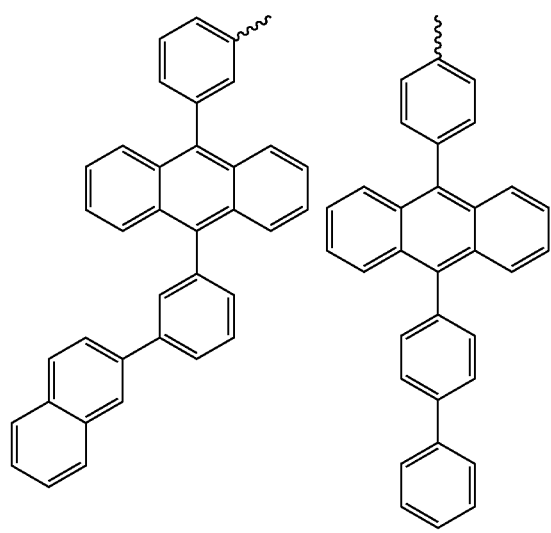
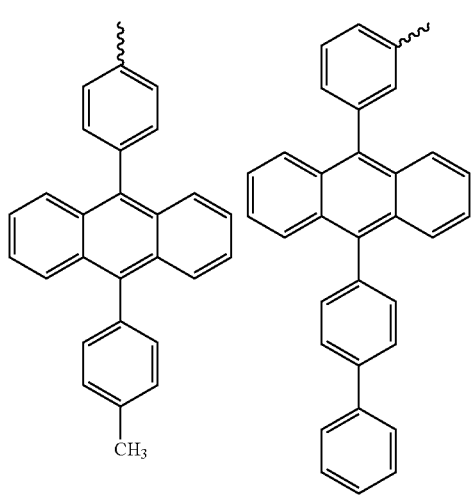

33
-continued
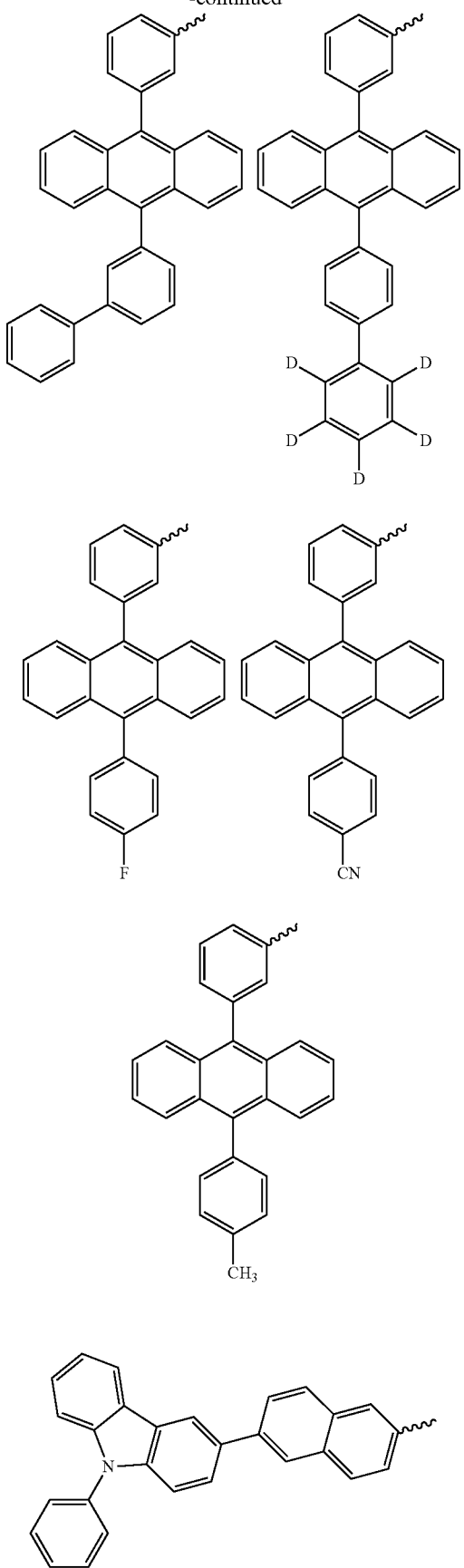
34
-continued
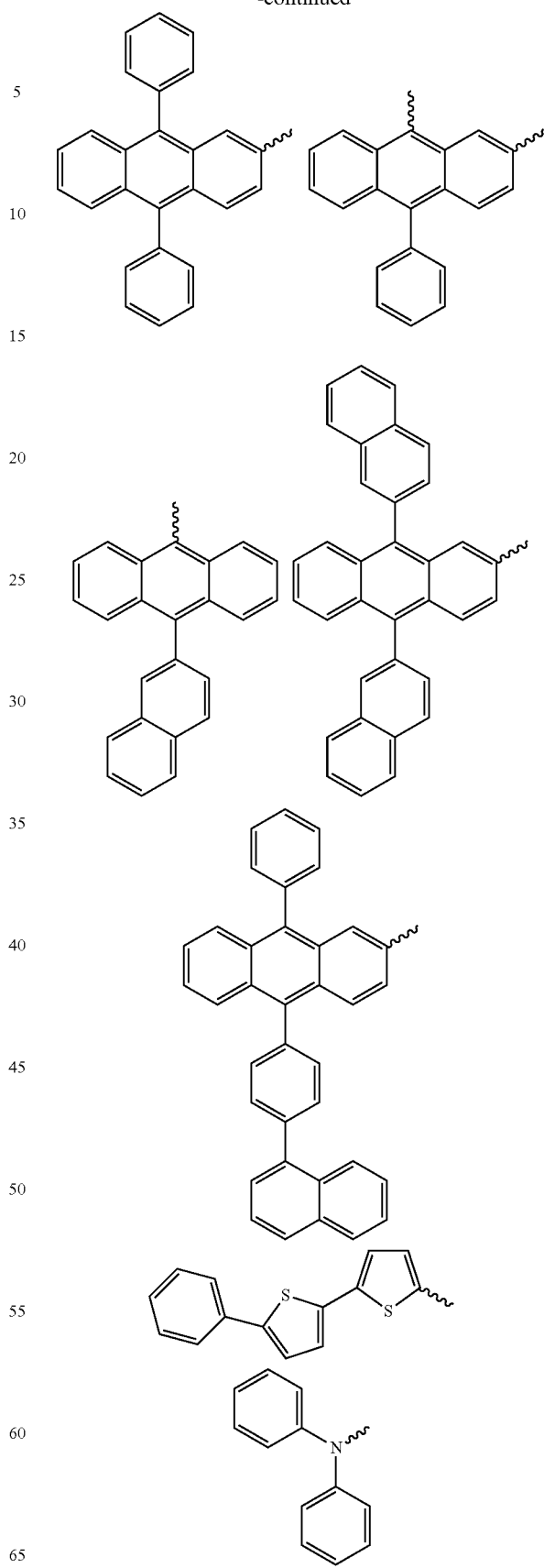

In particular, in the compound according to the present invention, R1 is selected from the group consisting of $C_6$~$C_{20}$ aryl group; $C_6$~$C_{20}$ aryl group that is substituted by $C_6$~$C_{40}$ aryl group or $C_3$~$C_{40}$ heteroaryl group that comprises O, N or S as a heteroatom; and $C_3$~$C_{20}$ heteroaryl group that is substituted by $C_6$~$C_{20}$ aryl group and comprises O, N or S as a heteroatom; and R2 is selected from the group consisting of $C_6$~$C_{20}$ aryl group; $C_6$~$C_{20}$ aryl group that is substituted by $C_6$~$C_{40}$ aryl group, $C_3$~$C_{40}$ heteroaryl group that comprises O, N or S as a heteroatom or $C_5$~$C_{40}$ arylamine group; $C_3$~$C_{20}$ heteroaryl group that is substituted by $C_6$~$C_{20}$ aryl group and comprises O, N or S as a heteroatom; and $C_6$~$C_{20}$ arylamine group; and it is preferable that X and R7 that are symmetrical to R1 and R2 with the center of the chrysene core are hydrogen, and at least one of R3 to R6 is selected from the group consisting of $C_6$~$C_{20}$ aryl group; $C_6$~$C_{20}$ aryl group that is substituted by $C_6$~$C_{40}$ aryl group, $C_3$~$C_{40}$ heteroaryl group that comprises O, N or S as a heteroatom or $C_5$~$C_{40}$ arylamine group; $C_3$~$C_{20}$ heteroaryl group that is substituted by $C_6$~$C_{20}$ aryl group and comprises O, N or S as a heteroatom; and $C_6$~$C_{20}$ arylamine group.

More preferably, R1 is selected from the group consisting of $C_6$~$C_{20}$ aryl group; $C_6$~$C_{20}$ aryl group that is substituted by $C_6$~$C_{40}$ aryl group or $C_3$~$C_{40}$ heteroaryl group that comprises O, N or S as a heteroatom; and $C_3$~$C_{20}$ heteroaryl group that is substituted by $C_6$~$C_{20}$ aryl group and comprises O, N or S as a heteroatom; R2 is selected from the group consisting of $C_6$~$C_{20}$ aryl group; $C_6$~$C_{20}$ aryl group that is substituted by $C_6$~$C_{40}$ aryl group, $C_3$~$C_{40}$ heteroaryl group that comprises O, N or S as a heteroatom or $C_5$~$C_{40}$ arylamine group; $C_3$~$C_{20}$ heteroaryl group that is substituted by $C_6$~$C_{20}$ aryl group and comprises O, N or S as a heteroatom; and $C_6$~$C_{20}$ arylamine group;

R5 is selected from the group consisting of $C_6$~$C_{20}$ aryl group; $C_6$~$C_{20}$ aryl group that is substituted by $C_6$~$C_{40}$ aryl group, $C_3$~$C_{40}$ heteroaryl group that comprises O, N or S as a heteroatom or $C_5$~$C_{40}$ arylamine group; $C_3$~$C_{20}$ heteroaryl group that is substituted by $C_6$~$C_{20}$ aryl group and comprises O, N or S as a heteroatom; and $C_6$~$C_{20}$ arylamine group, and R3, R4, R6, R7 and X are hydrogen, but they are not limited thereto.

As described above, the compound that is represented by Formula 1 according to the present invention may be a compound that has at least three functional groups with the center of chrysene core by comprising specific functional group on at least one of R1 and R2, R3 to R7, and X.

In particular, in the compound according to the present invention, in the case of when specific functional group is comprised in R1, R2, and R5 of Formula 1, the organic electronic device that comprises the compound may show improved properties such as efficiency, driving voltage, and stability.

In the compound that is represented by Formula 1 according to the present invention, detailed examples of each substituent group are described in the following Tables 1 to 6, but they are not limited thereto.

TABLE 1

| Formula | R1 | R2 | R5 | R3, R4, R6, X, R7 |
|---|---|---|---|---|
| 1-1 | phenyl | phenyl | phenyl | H |
| 1-2 | phenyl | phenyl | 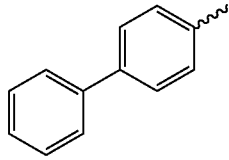 | H |
| 1-3 | phenyl | phenyl | 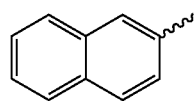 | H |
| 1-4 | phenyl | phenyl | 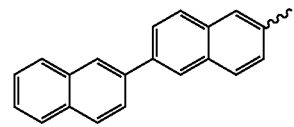 | H |
| 1-5 | phenyl | phenyl | 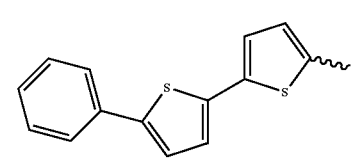 | H |

TABLE 1-continued
| Formula | R1 | R2 | R5 | R3, R4, R6, X, R7 |
|---|---|---|---|---|
| 1-6 | phenyl | phenyl | 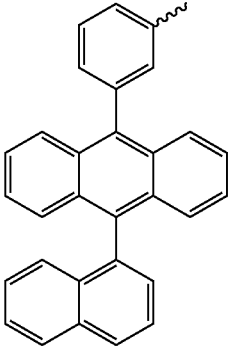 | H |
| 1-7 | phenyl | phenyl | 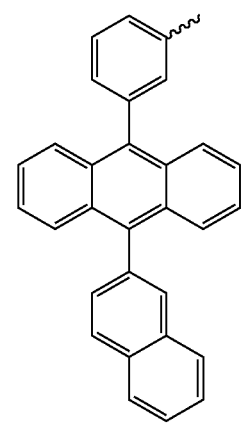 | H |
| 1-8 | phenyl | phenyl | 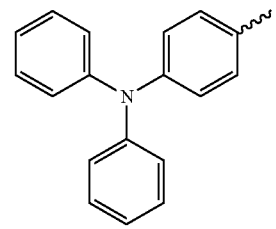 | H |
| 1-9 | phenyl | phenyl | 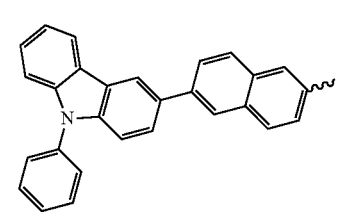 | H |
| 1-10 | phenyl | phenyl | 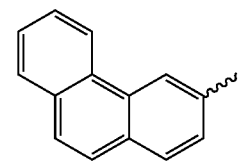 | H |
| 1-11 | phenyl | phenyl | 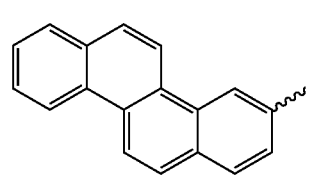 | H |

TABLE 1-continued
| Formula | R1 | R2 | R5 | R3, R4, R6, X, R7 |
|---|---|---|---|---|
| 1-12 | phenyl | phenyl | 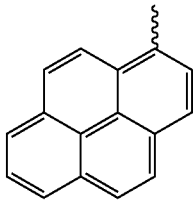 | H |
| 1-13 | phenyl | phenyl | 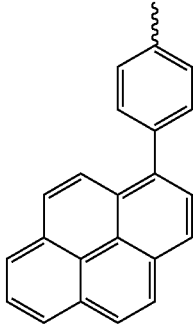 | H |
| 1-14 | phenyl | phenyl | 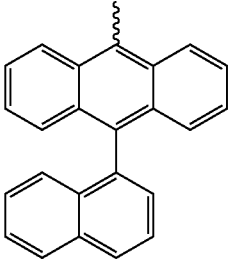 | H |
| 1-15 | phenyl | phenyl | 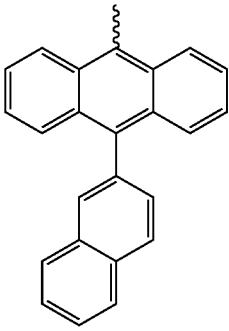 | H |

TABLE 1-continued
| Formula | R1 | R2 | R5 | R3, R4, R6, X, R7 |
|---|---|---|---|---|
| 1-16 | phenyl | phenyl | 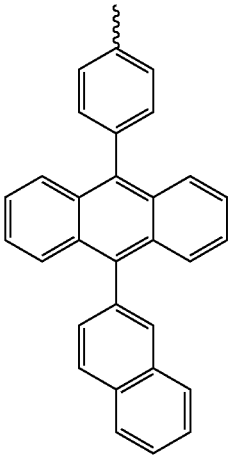 | H |
| 1-17 | phenyl | phenyl | 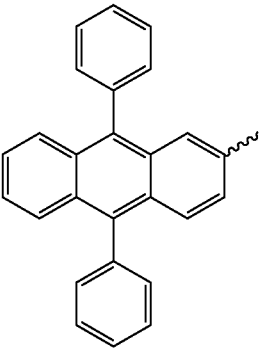 | H |
| 1-18 | phenyl | phenyl | 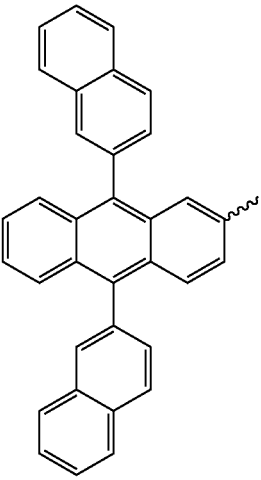 | H |

TABLE 1-continued
| Formula | R1 | R2 | R5 | R3, R4, R6, X, R7 |
|---|---|---|---|---|
| 1-19 | phenyl | phenyl | 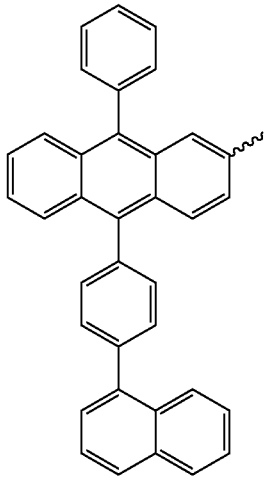 | H |
| 1-20 | phenyl | phenyl | 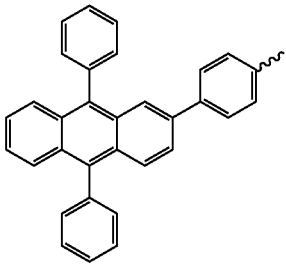 | H |
| 1-21 | phenyl | phenyl | 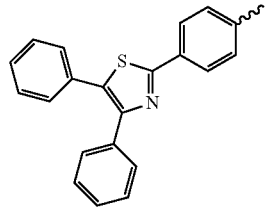 | H |
| 1-22 | phenyl | phenyl | 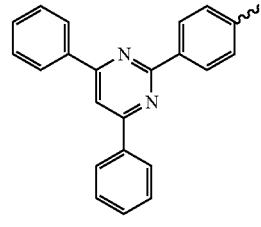 | H |
| 1-23 | phenyl | 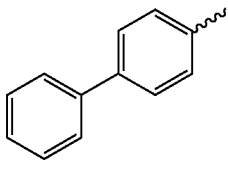 | phenyl | H |
| 1-24 | phenyl | 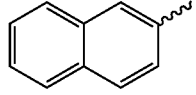 | phenyl | H |

TABLE 1-continued
| Formula | R1 | R2 | R5 | R3, R4, R6, X, R7 |
|---|---|---|---|---|
| 1-25 | phenyl | 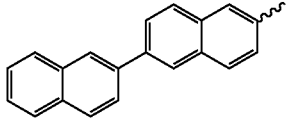 | phenyl | H |
| 1-26 | phenyl | 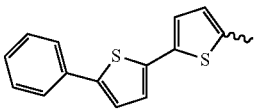 | phenyl | H |
| 1-27 | phenyl | 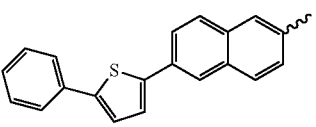 | phenyl | H |
| 1-28 | phenyl | 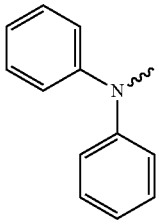 | phenyl | H |
| 1-29 | phenyl | 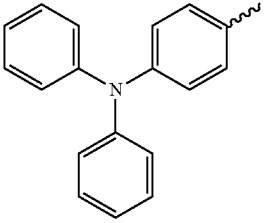 | phenyl | H |
| 1-30 | phenyl | 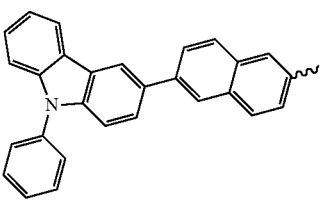 | phenyl | H |
| 1-31 | phenyl | 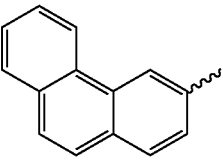 | phenyl | H |
| 1-32 | phenyl | 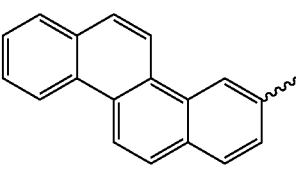 | phenyl | H |

TABLE 1-continued
| Formula | R1 | R2 | R5 | R3, R4, R6, X, R7 |
|---|---|---|---|---|
| 1-33 | phenyl | 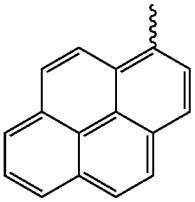 | phenyl | H |
| 1-34 | phenyl | 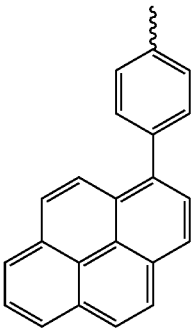 | phenyl | H |
| 1-35 | phenyl | 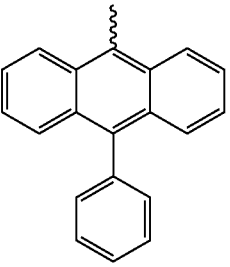 | phenyl | H |
| 1-36 | phenyl | 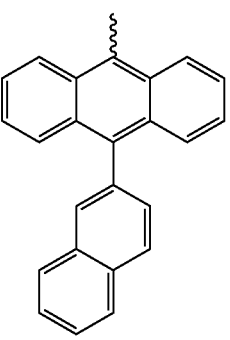 | phenyl | H |

TABLE 1-continued
| Formula | R1 | R2 | R5 | R3, R4, R6, X, R7 |
|---|---|---|---|---|
| 1-37 | phenyl | 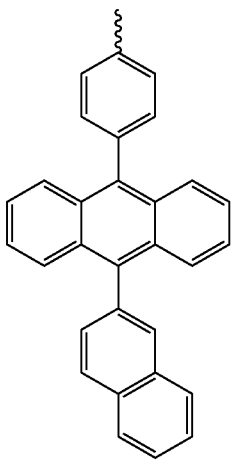 | phenyl | H |
| 1-38 | phenyl | 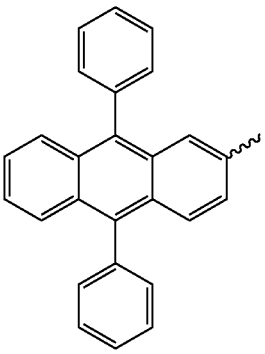 | phenyl | H |
| 1-39 | phenyl | 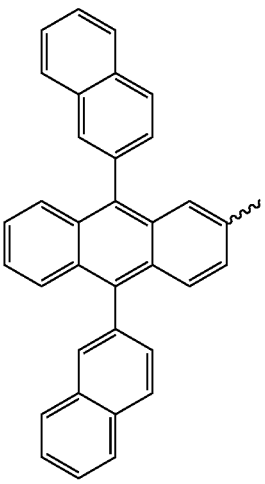 | phenyl | H |

TABLE 1-continued
| Formula | R1 | R2 | R5 | R3, R4, R6, X, R7 |
|---|---|---|---|---|
| 1-40 | phenyl | 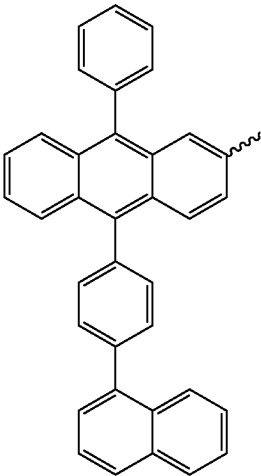 | phenyl | H |
| 1-41 | phenyl | 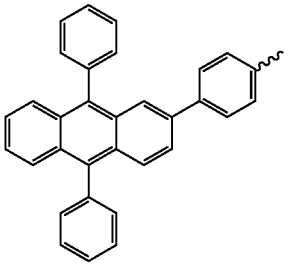 | phenyl | H |
| 1-42 | phenyl | 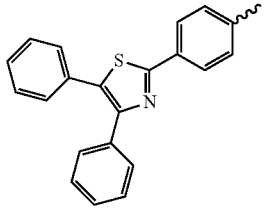 | phenyl | H |
| 1-43 | phenyl | 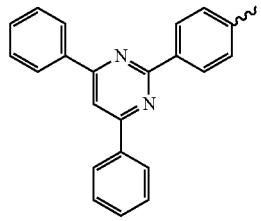 | phenyl | H |
| 1-44 | 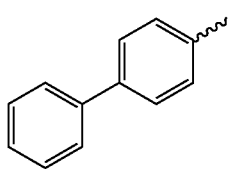 | phenyl | 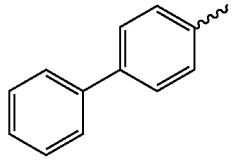 | H |
| 1-45 | 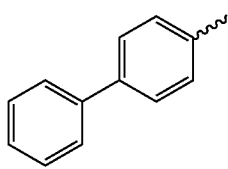 | phenyl | 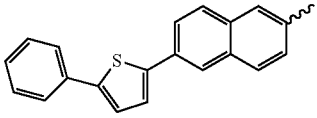 | H |

TABLE 1-continued
| Formula | R1 | R2 | R5 | R3, R4, R6, X, R7 |
|---|---|---|---|---|
| 1-46 | 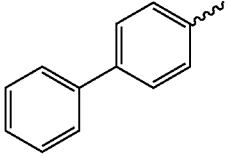 | phenyl | 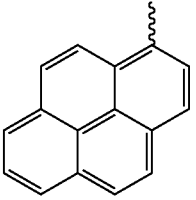 | H |
| 1-47 | 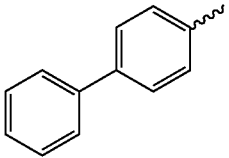 | phenyl | 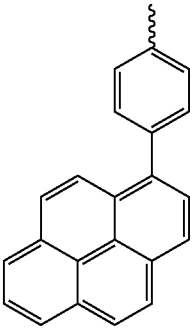 | H |
| 1-48 | 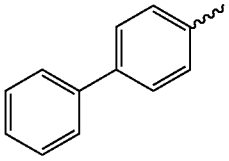 | phenyl | 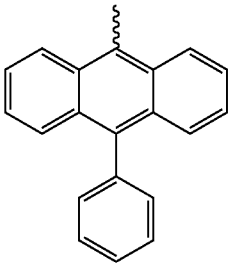 | H |
| 1-49 | 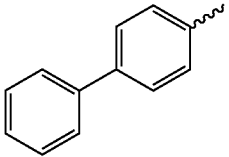 | phenyl | 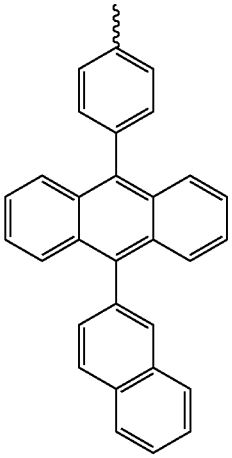 | H |

TABLE 1-continued
| Formula | R1 | R2 | R5 | R3, R4, R6, X, R7 |
|---|---|---|---|---|
| 1-50 | 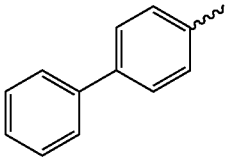 | phenyl | 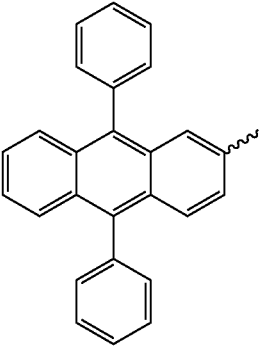 | H |
| 1-51 | 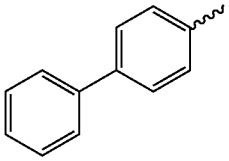 | phenyl | 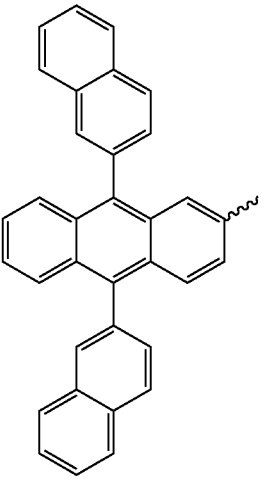 | H |
| 1-52 | 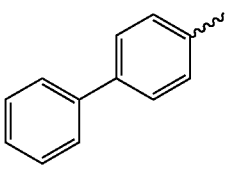 | phenyl | 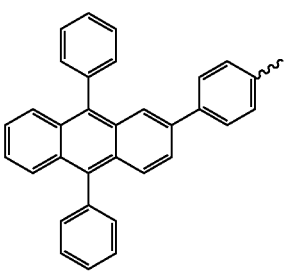 | H |
| 1-53 | 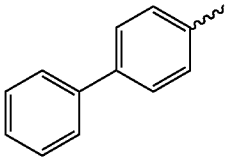 | phenyl | 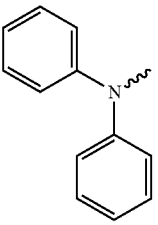 | H |
| 1-54 | 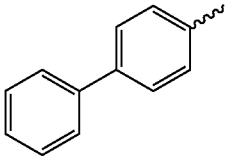 | phenyl | 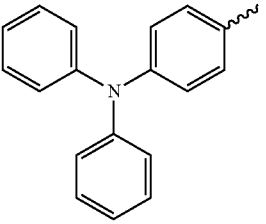 | H |

TABLE 1-continued
| Formula | R1 | R2 | R5 | R3, R4, R6, X, R7 |
|---|---|---|---|---|
| 1-55 | 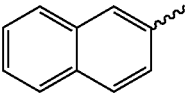 | phenyl | 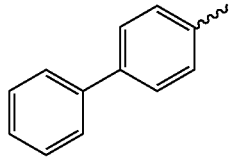 | H |
| 1-56 | 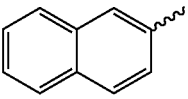 | phenyl | 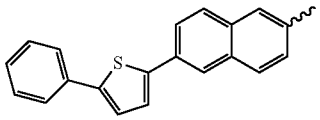 | H |
| 1-57 | 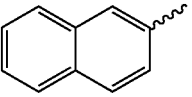 | phenyl | 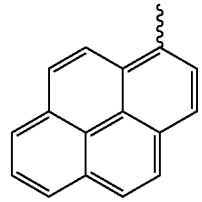 | H |
| 1-58 | 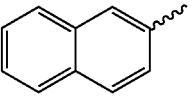 | phenyl | 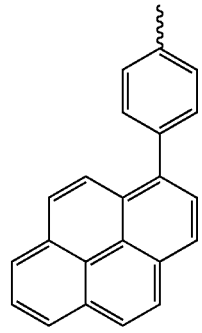 | H |
| 1-59 | 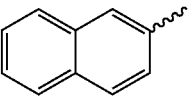 | phenyl | 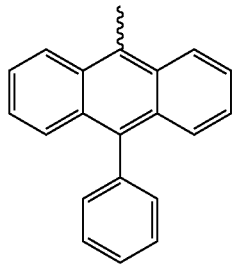 | H |

TABLE 1-continued
| Formula | R1 | R2 | R5 | R3, R4, R6, X, R7 |
|---|---|---|---|---|
| 1-60 | 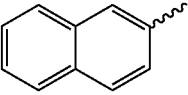 | phenyl | 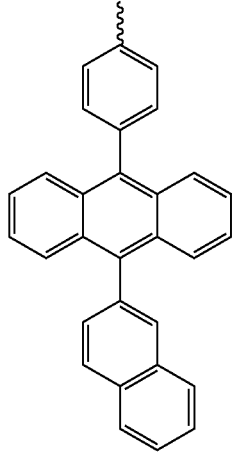 | H |
| 1-61 | 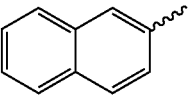 | phenyl | 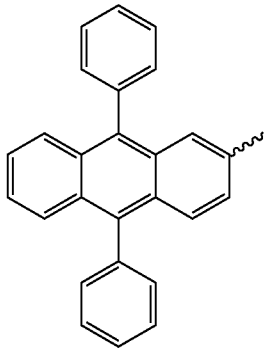 | H |
| 1-62 | 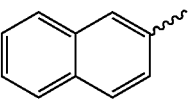 | phenyl | 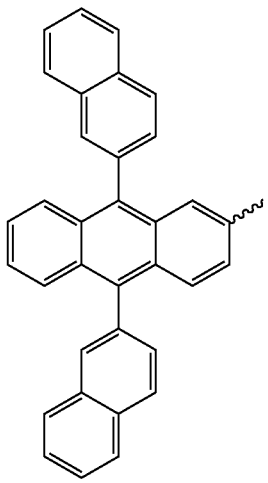 | H |
| 1-63 | 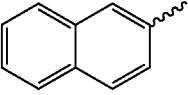 | phenyl | 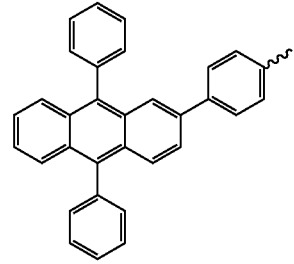 | H |

TABLE 1-continued

| Formula | R1 | R2 | R5 | R3, R4, R6, X, R7 |
|---|---|---|---|---|
| 1-64 | naphthyl | phenyl | N,N-diphenylamino | H |
| 1-65 | naphthyl | phenyl | 4-(N,N-diphenylamino)phenyl | H |
| 1-66 | 5-phenylthiophen-2-yl-thiophene | phenyl | biphenyl | H |
| 1-67 | 5-phenylthiophen-2-yl-thiophene | phenyl | 6-(5-phenylthiophen-2-yl)naphthyl | H |
| 1-68 | 5-phenylthiophen-2-yl-thiophene | phenyl | pyrenyl | H |
| 1-69 | 5-phenylthiophen-2-yl-thiophene | phenyl | 4-(pyren-1-yl)phenyl | H |

TABLE 1-continued
| Formula | R1 | R2 | R5 | R3, R4, R6, X, R7 |
|---|---|---|---|---|
| 1-70 | 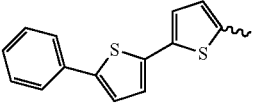 | phenyl | 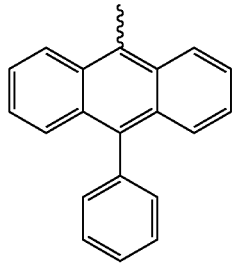 | H |
| 1-71 | 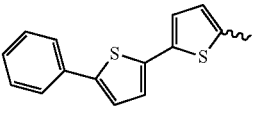 | phenyl | 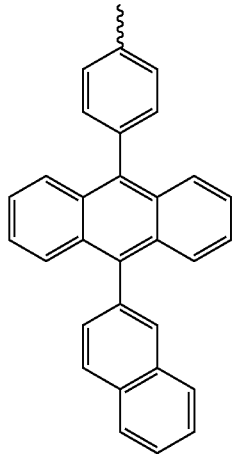 | H |
| 1-72 | 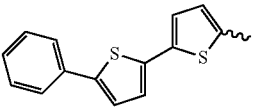 | phenyl | 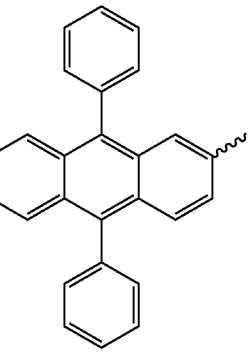 | H |
| 1-73 | 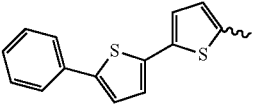 | phenyl | 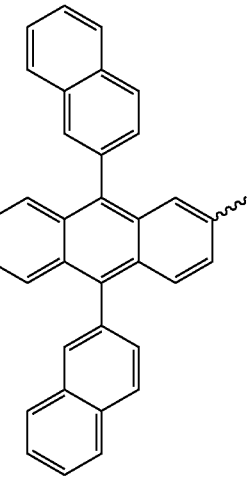 | H |

TABLE 1-continued
| Formula | R1 | R2 | R5 | R3, R4, R6, X, R7 |
|---|---|---|---|---|
| 1-74 | 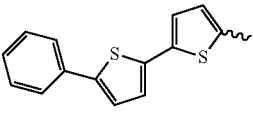 | phenyl | 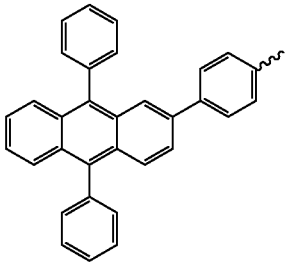 | H |
| 1-75 | 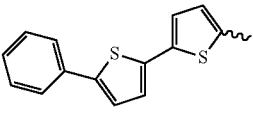 | phenyl | 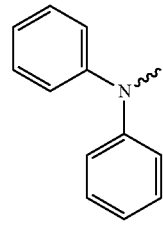 | H |
| 1-76 | 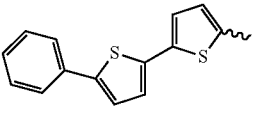 | phenyl | 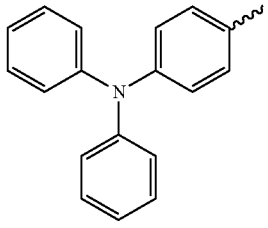 | H |
| 1-77 | 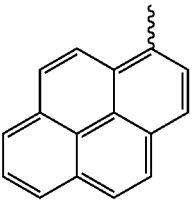 | phenyl | 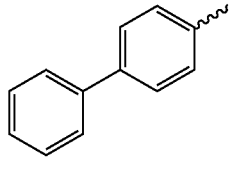 | H |
| 1-78 | 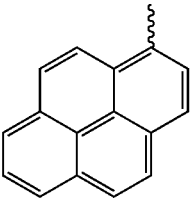 | phenyl | 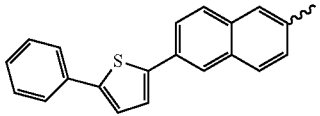 | H |
| 1-79 | 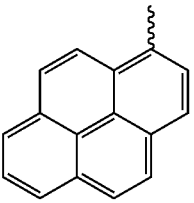 | phenyl | 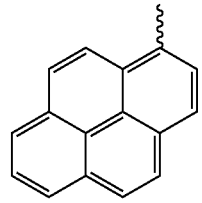 | H |

TABLE 1-continued
| Formula | R1 | R2 | R5 | R3, R4, R6, X, R7 |
|---|---|---|---|---|
| 1-80 | 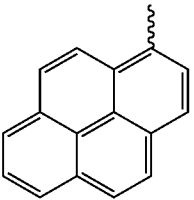 | phenyl | 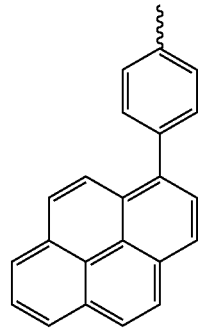 | H |
| 1-81 | 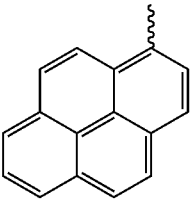 | phenyl | 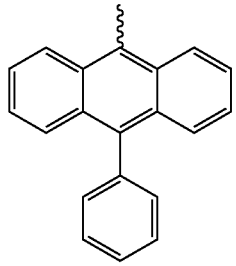 | H |
| 1-82 | 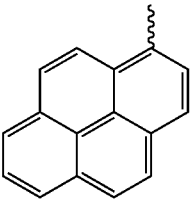 | phenyl | 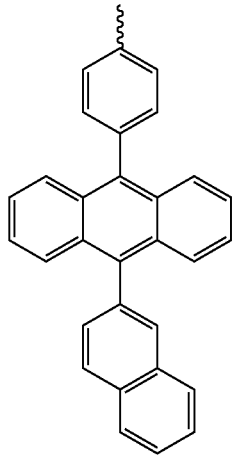 | H |
| 1-83 | 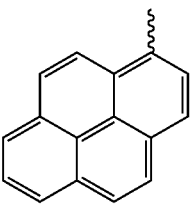 | phenyl | 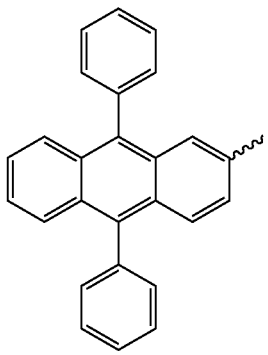 | H |

TABLE 1-continued
| Formula | R1 | R2 | R5 | R3, R4, R6, X, R7 |
|---|---|---|---|---|
| 1-84 | 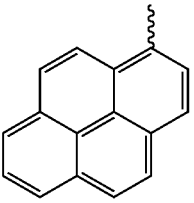 | phenyl | 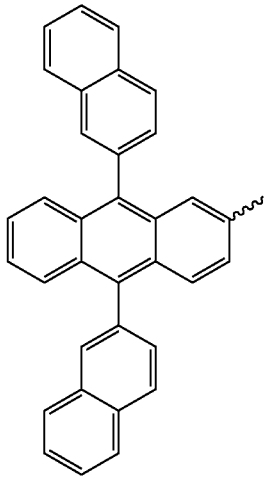 | H |
| 1-85 | 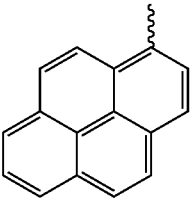 | phenyl | 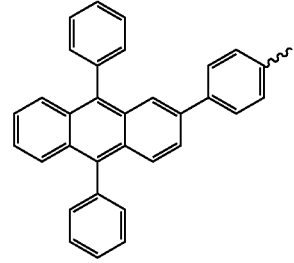 | H |
| 1-86 | 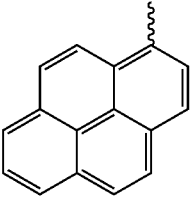 | phenyl | 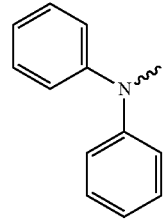 | H |
| 1-87 | 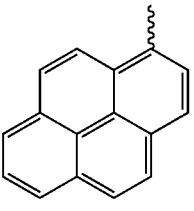 | phenyl | 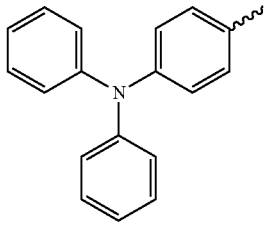 | H |
| 1-88 | 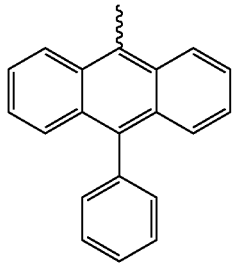 | phenyl | 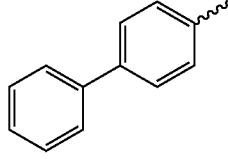 | H |

TABLE 1-continued

| Formula | R1 | R2 | R5 | R3, R4, R6, X, R7 |
|---|---|---|---|---|
| 1-89 | 10-phenylanthracen-9-yl | phenyl | 5-phenylthiophen-2-yl-naphthalen-6-yl | H |
| 1-90 | 10-phenylanthracen-9-yl | phenyl | pyren-1-yl | H |
| 1-91 | 10-phenylanthracen-9-yl | phenyl | 4-(pyren-1-yl)phenyl | H |
| 1-92 | 10-phenylanthracen-9-yl | phenyl | 10-phenylanthracen-9-yl | H |

TABLE 1-continued
| Formula | R1 | R2 | R5 | R3, R4, R6, X, R7 |
|---|---|---|---|---|
| 1-93 | 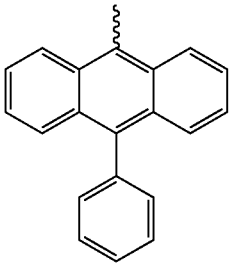 | phenyl | 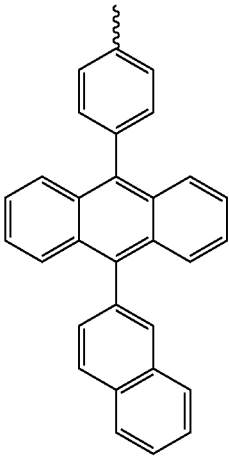 | H |
| 1-94 | 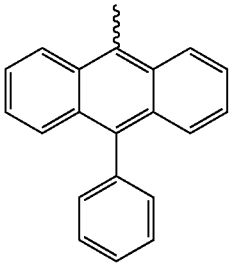 | phenyl | 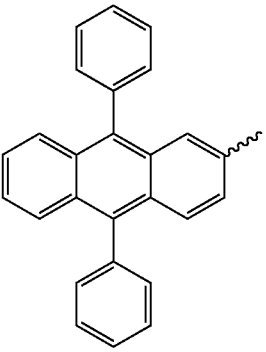 | H |
| 1-95 | 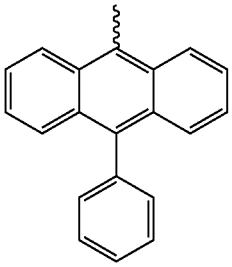 | phenyl | 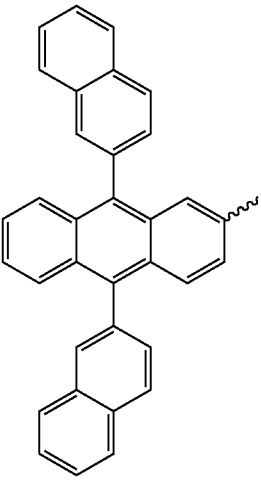 | H |
| 1-96 | 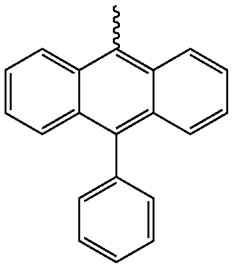 | phenyl | 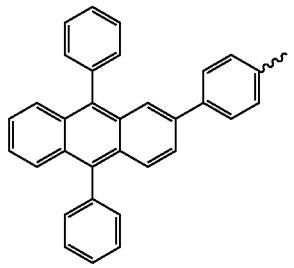 | H |

TABLE 1-continued

| Formula | R1 | R2 | R5 | R3, R4, R6, X, R7 |
|---|---|---|---|---|
| 1-97 | 10-phenylanthracen-9-yl | phenyl | diphenylamino | H |
| 1-98 | 10-phenylanthracen-9-yl | phenyl | 4-(diphenylamino)phenyl | H |
| 1-99 | 2-(9,10-diphenylanthracen-2-yl)phenyl | phenyl | biphenyl-4-yl | H |
| 1-100 | 2-(9,10-diphenylanthracen-2-yl)phenyl | phenyl | 6-(5-phenylthiophen-2-yl)naphthalen-2-yl | H |
| 1-101 | 2-(9,10-diphenylanthracen-2-yl)phenyl | phenyl | pyren-1-yl | H |

TABLE 1-continued
| Formula | R1 | R2 | R5 | R3, R4, R6, X, R7 |
|---|---|---|---|---|
| 1-102 | 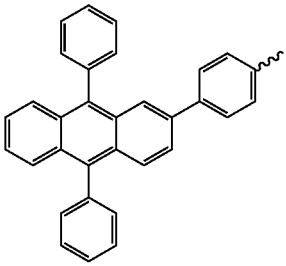 | phenyl | 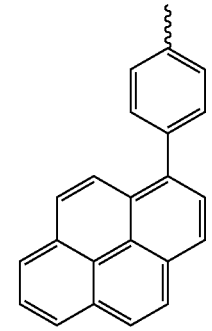 | H |
| 1-103 | 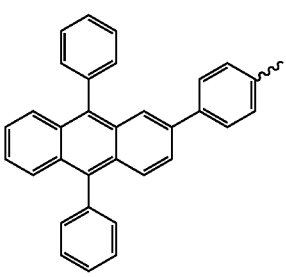 | phenyl | 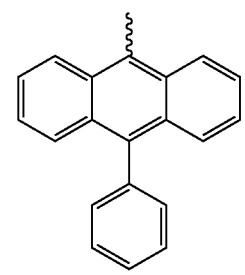 | H |
| 1-104 | 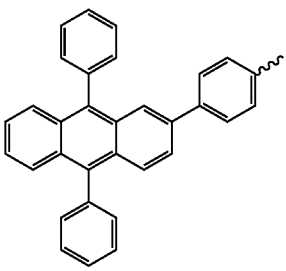 | phenyl | 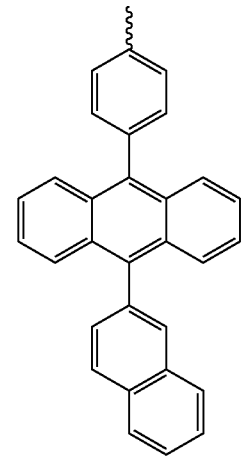 | H |
| 1-105 | 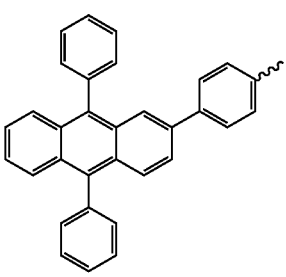 | phenyl | 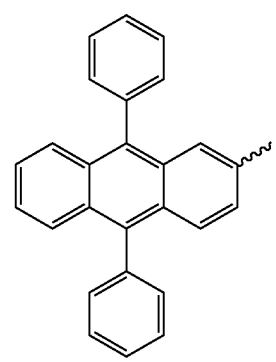 | H |

TABLE 1-continued

| Formula | R1 | R2 | R5 | R3, R4, R6, X, R7 |
|---|---|---|---|---|
| 1-106 | (9,10-diphenylanthracen-2-yl)phenyl | phenyl | 9,10-di(naphthalen-2-yl)anthracen-2-yl | H |
| 1-107 | (9,10-diphenylanthracen-2-yl)phenyl | phenyl | (9,10-diphenylanthracen-2-yl)phenyl | H |
| 1-108 | (9,10-diphenylanthracen-2-yl)phenyl | phenyl | diphenylamino | H |
| 1-109 | (9,10-diphenylanthracen-2-yl)phenyl | phenyl | 4-(diphenylamino)phenyl | H |

TABLE 2
| Formula | R1 | R2 | R3 | R4, R5, R6, X, R7 |
|---|---|---|---|---|
| 2-1 | phenyl | phenyl | phenyl | H |
| 2-2 | phenyl | phenyl | 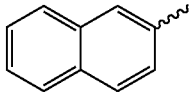 | H |
| 2-3 | phenyl | phenyl | 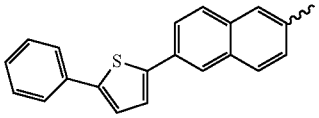 | H |
| 2-4 | phenyl | phenyl | 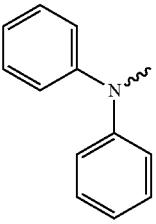 | H |
| 2-5 | phenyl | phenyl | 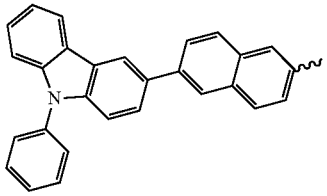 | H |
| 2-6 | phenyl | phenyl | 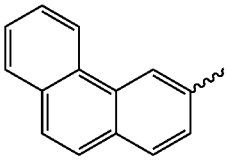 | H |
| 2-7 | phenyl | phenyl | 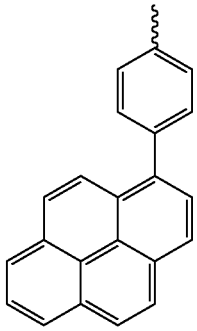 | H |
| 2-8 | phenyl | phenyl | 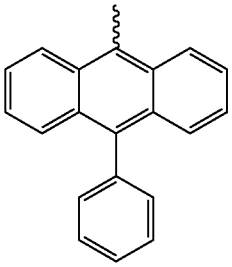 | H |

TABLE 2-continued
| Formula | R1 | R2 | R3 | R4, R5, R6, X, R7 |
|---|---|---|---|---|
| 2-9 | phenyl | phenyl | 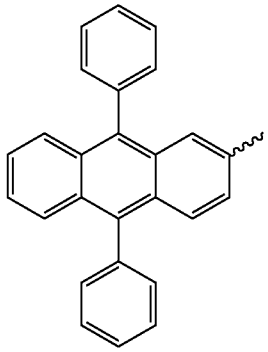 | H |
| 2-10 | phenyl | phenyl | 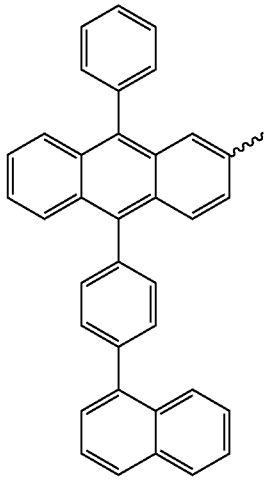 | H |
| 2-11 | phenyl | phenyl | 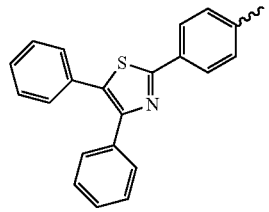 | H |
| 2-12 | phenyl | 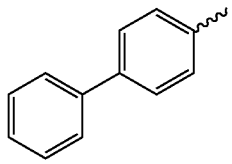 | phenyl | H |
| 2-13 | phenyl | 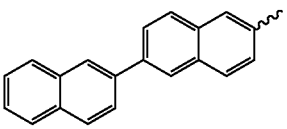 | phenyl | H |
| 2-14 | phenyl | 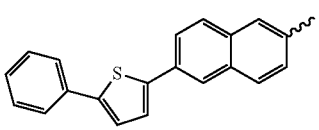 | phenyl | H |

TABLE 2-continued

| Formula | R1 | R2 | R3 | R4, R5, R6, X, R7 |
|---|---|---|---|---|
| 2-15 | phenyl | (4-(diphenylamino)phenyl) | phenyl | H |
| 2-16 | phenyl | (phenanthren-2-yl) | phenyl | H |
| 2-17 | phenyl | (pyren-1-yl) | phenyl | H |
| 2-18 | phenyl | (10-phenylanthracen-9-yl) | phenyl | H |
| 2-19 | phenyl | (4-(10-(naphthalen-2-yl)anthracen-9-yl)phenyl) | phenyl | H |

TABLE 2-continued
| Formula | R1 | R2 | R3 | R4, R5, R6, X, R7 |
|---|---|---|---|---|
| 2-20 | phenyl | 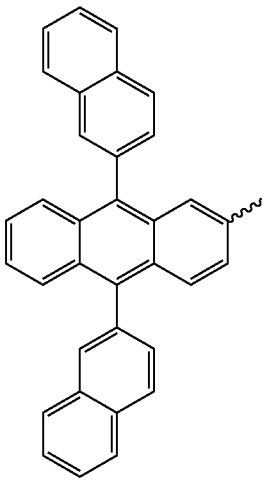 | phenyl | H |
| 2-21 | phenyl | 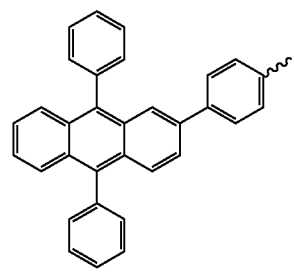 | phenyl | H |
| 2-22 | phenyl | 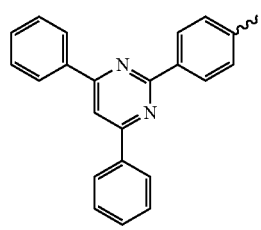 | phenyl | H |
| 2-23 | 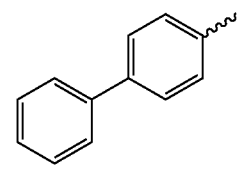 | phenyl | 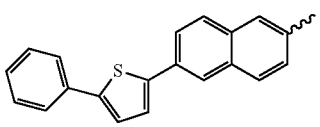 | H |
| 2-24 | 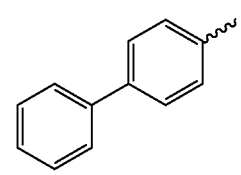 | phenyl | 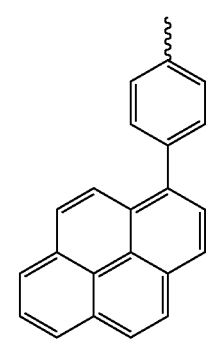 | H |

TABLE 2-continued
| Formula | R1 | R2 | R3 | R4, R5, R6, X, R7 |
|---|---|---|---|---|
| 2-25 | 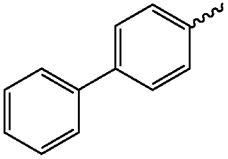 | phenyl | 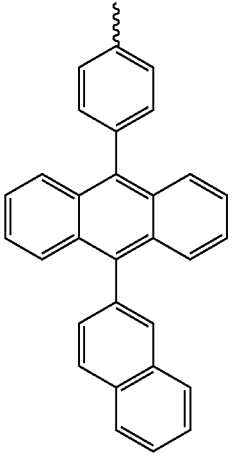 | H |
| 2-26 | 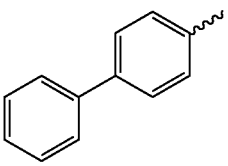 | phenyl | 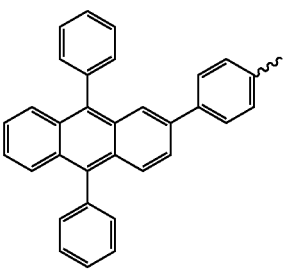 | H |
| 2-27 | 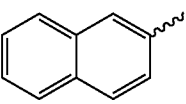 | phenyl | 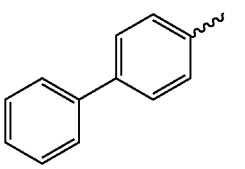 | H |
| 2-28 | 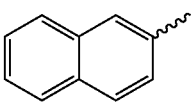 | phenyl | 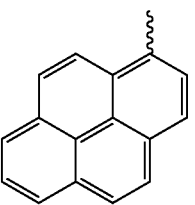 | H |
| 2-29 | 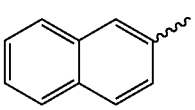 | phenyl | 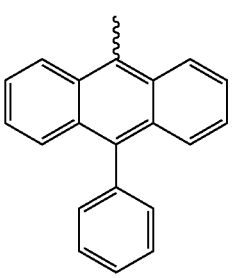 | H |

TABLE 2-continued
| Formula | R1 | R2 | R3 | R4, R5, R6, X, R7 |
|---|---|---|---|---|
| 2-30 | 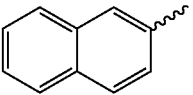 | phenyl | 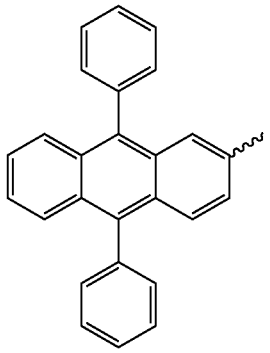 | H |
| 2-31 | 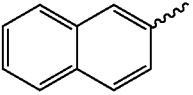 | phenyl | 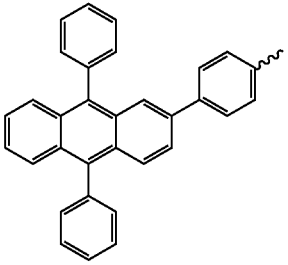 | H |
| 2-32 | 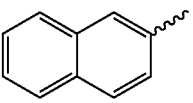 | phenyl | 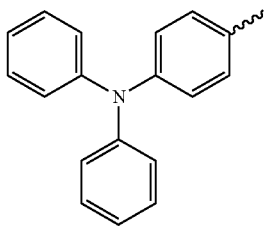 | H |
| 2-33 | 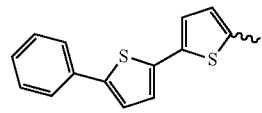 | phenyl | 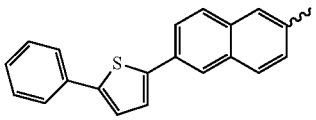 | H |
| 2-34 | 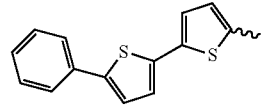 | phenyl | 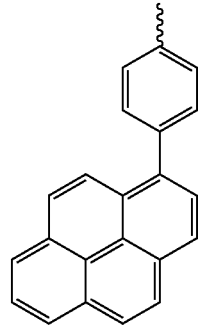 | H |

TABLE 2-continued

| Formula | R1 | R2 | R3 | R4, R5, R6, X, R7 |
|---|---|---|---|---|
| 2-35 | (5-phenylthiophen-2-yl)thiophene | phenyl | 4-(10-(naphthalen-2-yl)anthracen-9-yl)phenyl | H |
| 2-36 | (5-phenylthiophen-2-yl)thiophene | phenyl | 9,10-di(naphthalen-2-yl)anthracen-2-yl | H |
| 2-37 | (5-phenylthiophen-2-yl)thiophene | phenyl | diphenylamino | H |
| 2-38 | pyrenyl | phenyl | 6-(5-phenylthiophen-2-yl)naphthalen-2-yl | H |

TABLE 2-continued
| Formula | R1 | R2 | R3 | R4, R5, R6, X, R7 |
|---|---|---|---|---|
| 2-39 | 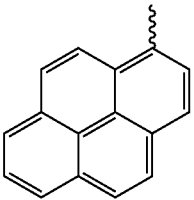 | phenyl | 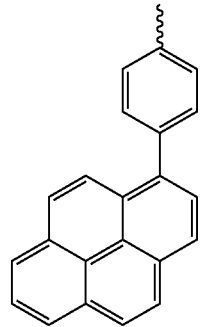 | H |
| 2-40 | 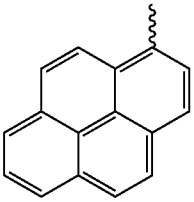 | phenyl | 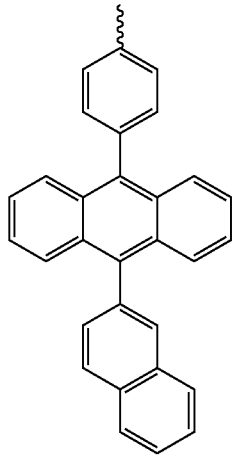 | H |
| 2-41 | 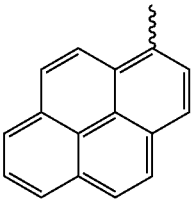 | phenyl | 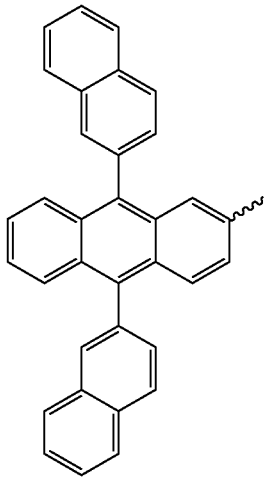 | H |
| 2-42 | 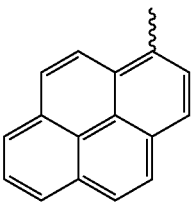 | phenyl | 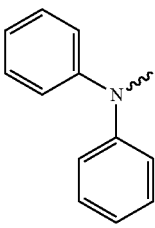 | H |

TABLE 2-continued

| Formula | R1 | R2 | R3 | R4, R5, R6, X, R7 |
|---|---|---|---|---|
| 2-43 | 9-phenylanthracen-10-yl | phenyl | biphenyl-4-yl | H |
| 2-44 | 9-phenylanthracen-10-yl | phenyl | pyren-1-yl | H |
| 2-45 | 9-phenylanthracen-10-yl | phenyl | 9-phenylanthracen-10-yl | H |
| 2-46 | 9-phenylanthracen-10-yl | phenyl | 9,10-diphenylanthracen-2-yl | H |
| 2-47 | 9-phenylanthracen-10-yl | phenyl | 4-(9,10-diphenylanthracen-2-yl)phenyl | H |

TABLE 2-continued

| Formula | R1 | R2 | R3 | R4, R5, R6, X, R7 |
|---|---|---|---|---|
| 2-48 | 10-phenylanthracen-9-yl | phenyl | 4-(diphenylamino)phenyl | H |
| 2-49 | 9,10-diphenylanthracen-2-yl (via phenyl) | phenyl | 5-phenylthiophen-2-yl-naphthalen-2-yl | H |
| 2-50 | 9,10-diphenylanthracen-2-yl (via phenyl) | phenyl | 4-(pyren-1-yl)phenyl | H |
| 2-51 | 9,10-diphenylanthracen-2-yl (via phenyl) | phenyl | 4-(10-(naphthalen-2-yl)anthracen-9-yl)phenyl | H |

TABLE 2-continued
| Formula | R1 | R2 | R3 | R4, R5, R6, X, R7 |
|---|---|---|---|---|
| 2-52 | 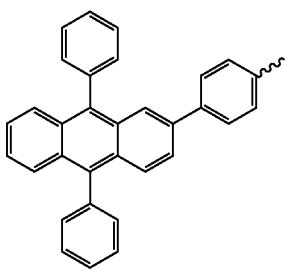 | phenyl | 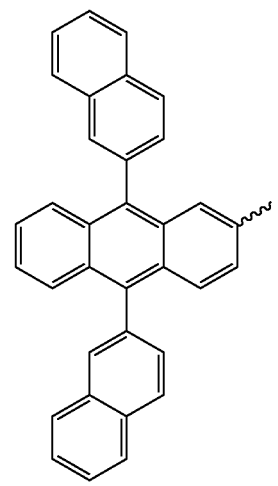 | H |
| 2-53 | 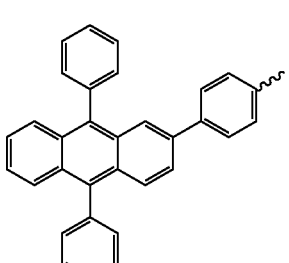 | phenyl | 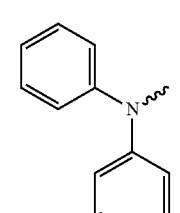 | H |
TABLE 3
| Formula | R1 | R2 | R6 | R3, R4, R5, X, R7 |
|---|---|---|---|---|
| 3-1 | phenyl | phenyl | phenyl | H |
| 3-2 | phenyl | phenyl | 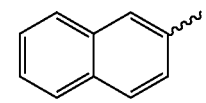 | H |
| 3-3 | phenyl | phenyl | 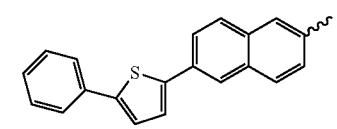 | H |
| 3-4 | phenyl | phenyl | 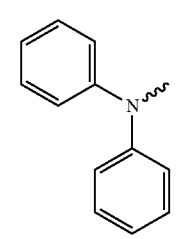 | H |

TABLE 3-continued

| Formula | R1 | R2 | R6 | R3, R4, R5, X, R7 |
|---|---|---|---|---|
| 3-5 | phenyl | phenyl | (9-phenylcarbazol-3-yl)-naphthalen-2-yl | H |
| 3-6 | phenyl | phenyl | phenanthren-2-yl | H |
| 3-7 | phenyl | phenyl | 1-(4-phenyl)pyrenyl | H |
| 3-8 | phenyl | phenyl | 10-phenylanthracen-9-yl | H |
| 3-9 | phenyl | phenyl | 9,10-diphenylanthracen-2-yl | H |

TABLE 3-continued
| Formula | R1 | R2 | R6 | R3, R4, R5, X, R7 |
|---|---|---|---|---|
| 3-10 | phenyl | phenyl | 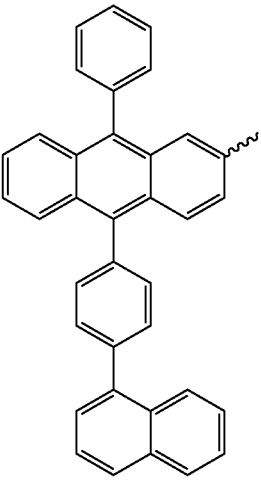 | H |
| 3-11 | phenyl | phenyl | 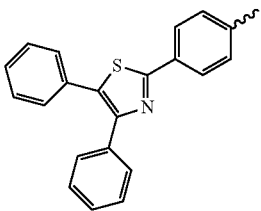 | H |
| 3-12 | phenyl | 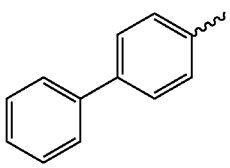 | phenyl | H |
| 3-13 | phenyl | 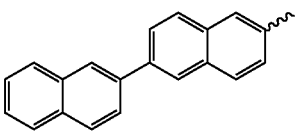 | phenyl | H |
| 3-14 | phenyl | 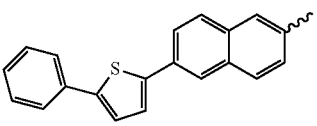 | phenyl | H |
| 3-15 | phenyl | 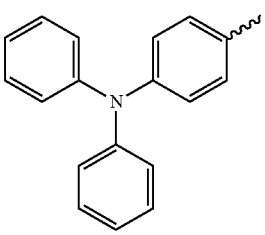 | phenyl | H |
| 3-16 | phenyl | 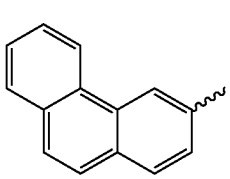 | phenyl | H |

TABLE 3-continued
| Formula | R1 | R2 | R6 | R3, R4, R5, X, R7 |
|---|---|---|---|---|
| 3-17 | phenyl | 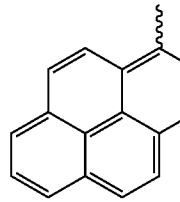 | phenyl | H |
| 3-18 | phenyl | 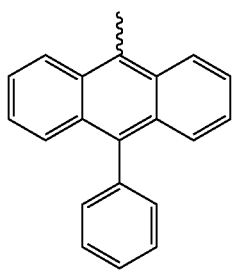 | phenyl | H |
| 3-19 | phenyl | 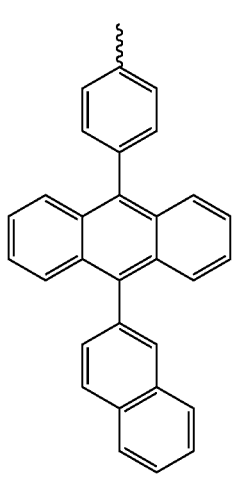 | phenyl | H |
| 3-20 | phenyl | 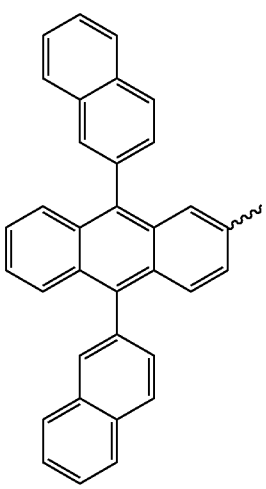 | phenyl | H |

TABLE 3-continued
| Formula | R1 | R2 | R6 | R3, R4, R5, X, R7 |
|---|---|---|---|---|
| 3-21 | phenyl | 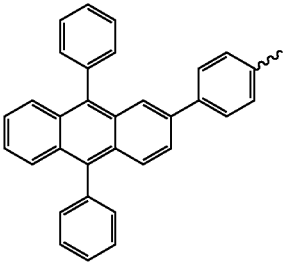 | phenyl | H |
| 3-22 | phenyl | 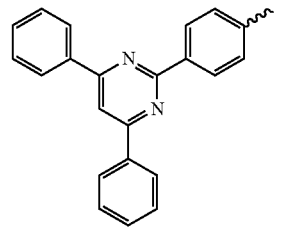 | phenyl | H |
| 3-23 | 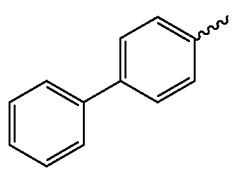 | phenyl | 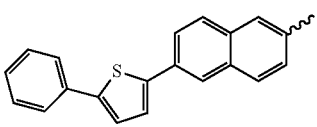 | H |
| 3-24 | 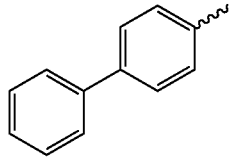 | phenyl | 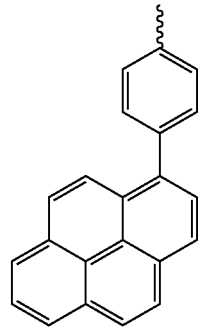 | H |
| 2-25 | 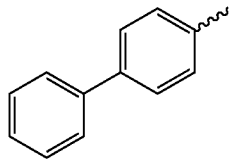 | phenyl | 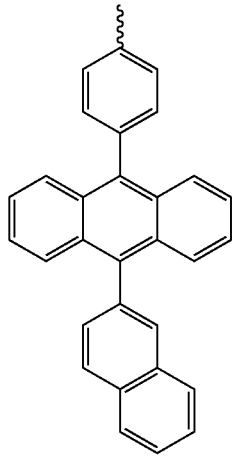 | H |

TABLE 3-continued

| Formula | R1 | R2 | R6 | R3, R4, R5, X, R7 |
|---|---|---|---|---|
| 3-26 | biphenyl | phenyl | 2,9,10-triphenylanthracenyl | H |
| 3-27 | 2-naphthyl | phenyl | biphenyl | H |
| 3-28 | 2-naphthyl | phenyl | pyrenyl | H |
| 3-29 | 2-naphthyl | phenyl | 10-phenylanthracenyl | H |
| 3-30 | 2-naphthyl | phenyl | 9,10-diphenylanthracenyl | H |
| 3-31 | 2-naphthyl | phenyl | 2,9,10-triphenylanthracenyl | H |

TABLE 3-continued
| Formula | R1 | R2 | R6 | R3, R4, R5, X, R7 |
|---|---|---|---|---|
| 3-32 | 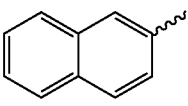 | phenyl | 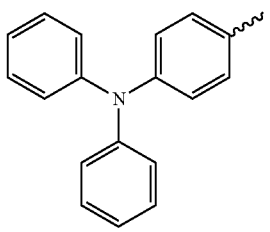 | H |
| 3-33 | 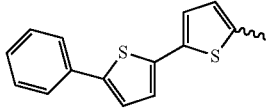 | phenyl | 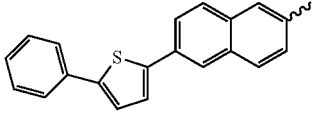 | H |
| 3-34 | 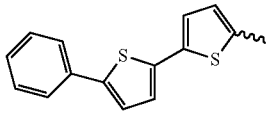 | phenyl | 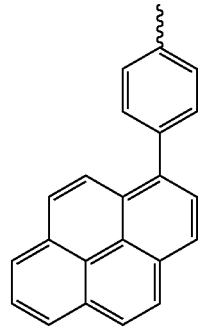 | H |
| 3-35 | 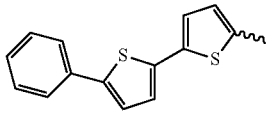 | phenyl | 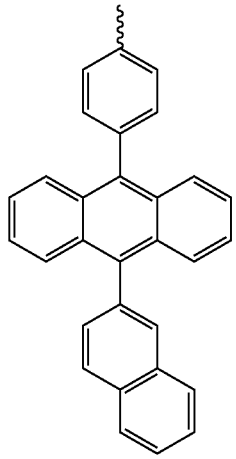 | H |

TABLE 3-continued
| Formula | R1 | R2 | R6 | R3, R4, R5, X, R7 |
|---|---|---|---|---|
| 3-36 | 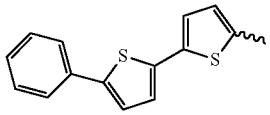 | phenyl | 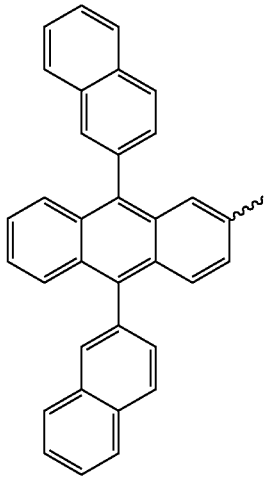 | H |
| 3-37 | 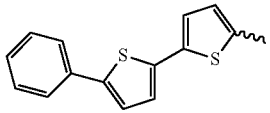 | phenyl | 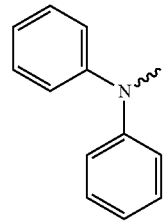 | H |
| 3-38 | 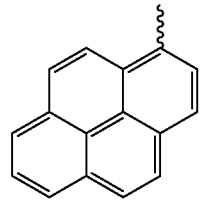 | phenyl | 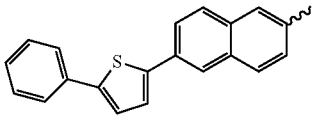 | H |
| 3-39 | 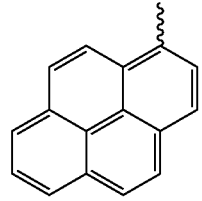 | phenyl | 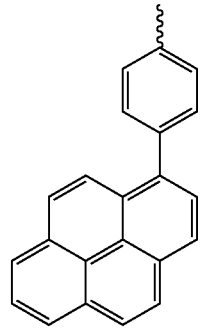 | H |

TABLE 3-continued
| Formula | R1 | R2 | R6 | R3, R4, R5, X, R7 |
|---|---|---|---|---|
| 3-40 | 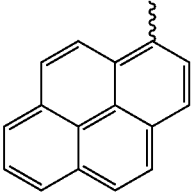 | phenyl | 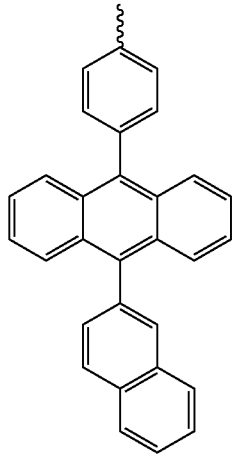 | H |
| 3-41 | 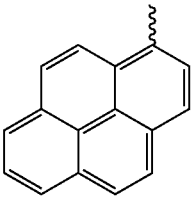 | phenyl | 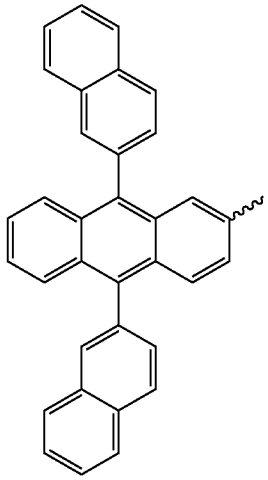 | H |
| 3-42 | 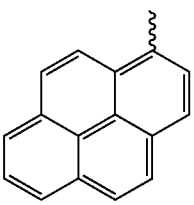 | phenyl | 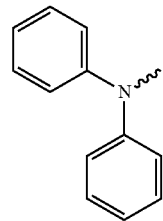 | H |
| 3-43 | 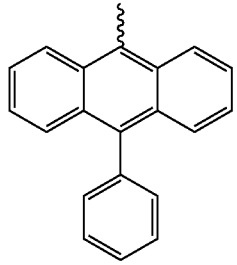 | phenyl | 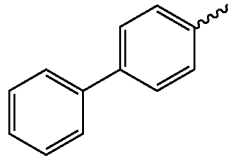 | H |

TABLE 3-continued
| Formula | R1 | R2 | R6 | R3, R4, R5, X, R7 |
|---|---|---|---|---|
| 3-44 | 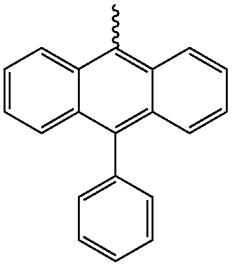 | phenyl | 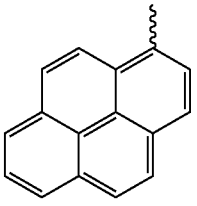 | H |
| 3-45 | 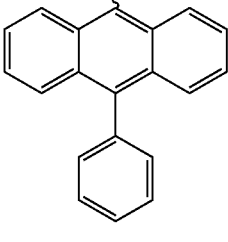 | phenyl | 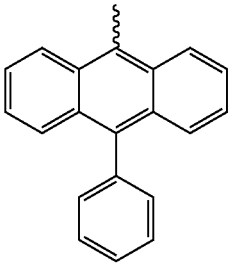 | H |
| 3-46 | 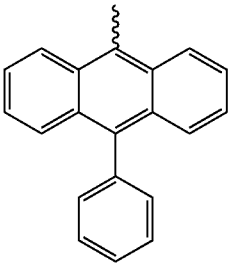 | phenyl | 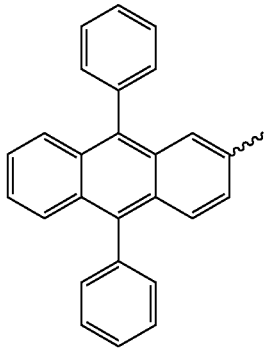 | H |
| 3-47 | 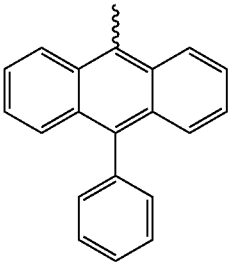 | phenyl | 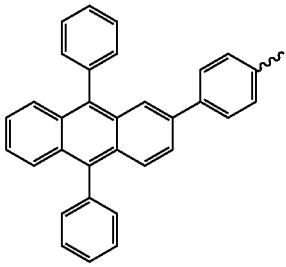 | H |
| 3-48 | 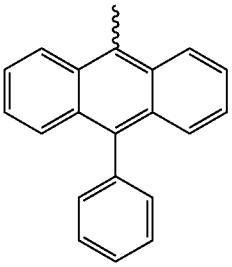 | phenyl | 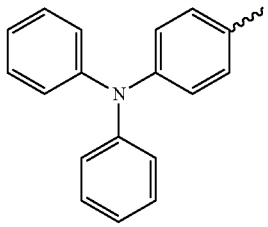 | H |

TABLE 3-continued
| Formula | R1 | R2 | R6 | R3, R4, R5, X, R7 |
|---|---|---|---|---|
| 3-49 | 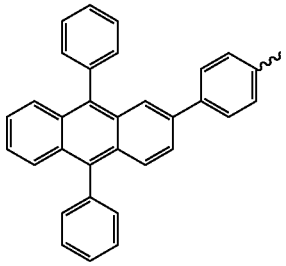 | phenyl | 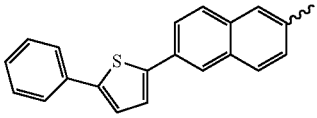 | H |
| 3-50 | 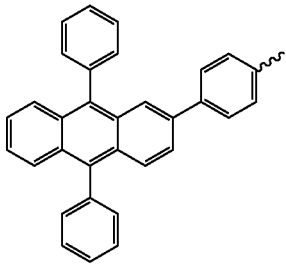 | phenyl | 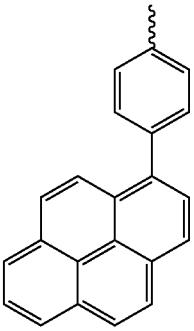 | H |
| 3-51 | 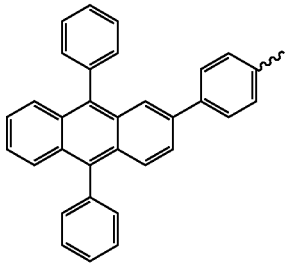 | phenyl | 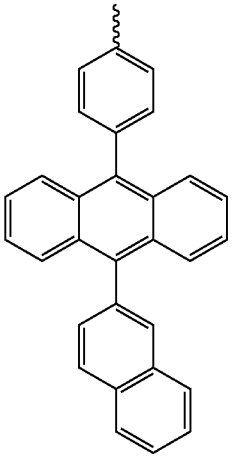 | H |
| 3-52 | 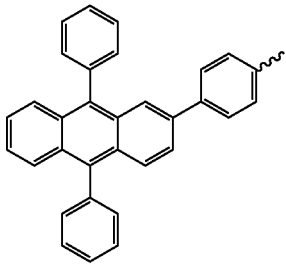 | phenyl | 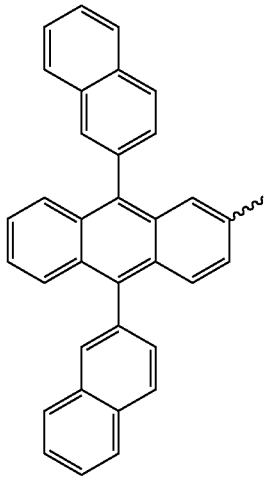 | H |

TABLE 3-continued

| Formula | R1 | R2 | R6 | R3, R4, R5, X, R7 |
|---|---|---|---|---|
| 3-53 | 9,10-diphenylanthracen-2-yl-phenyl | phenyl | N,N-diphenylamino | H |

TABLE 4

| Formula | R1 | R2 | R4 | R3, R5, R6, X, R7 |
|---|---|---|---|---|
| 4-1 | phenyl | phenyl | phenyl | H |
| 4-2 | phenyl | phenyl | naphthyl | H |
| 4-3 | phenyl | phenyl | 5-phenylthiophen-2-yl-naphthyl | H |
| 4-4 | phenyl | phenyl | N,N-diphenylamino | H |
| 4-5 | phenyl | phenyl | 9-phenylcarbazol-3-yl-naphthyl | H |
| 4-6 | phenyl | phenyl | phenanthrenyl | H |

TABLE 4-continued
| Formula | R1 | R2 | R4 | R3, R5, R6, X, R7 |
|---|---|---|---|---|
| 4-7 | phenyl | phenyl | 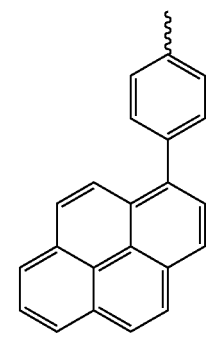 | H |
| 4-8 | phenyl | phenyl | 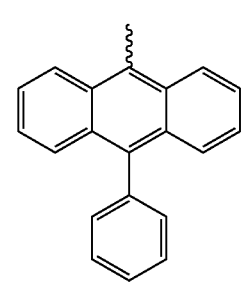 | H |
| 4-9 | phenyl | phenyl | 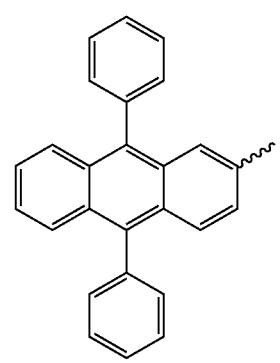 | H |
| 4-10 | phenyl | phenyl | 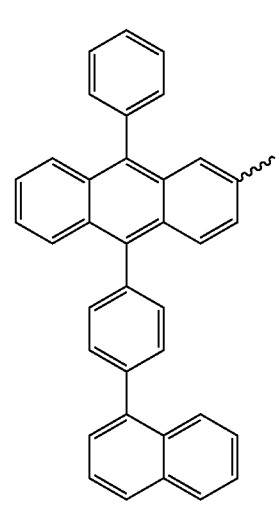 | H |

TABLE 4-continued
| Formula | R1 | R2 | R4 | R3, R5, R6, X, R7 |
|---|---|---|---|---|
| 4-11 | phenyl | phenyl | 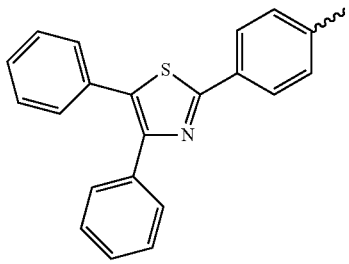 | H |
| 4-12 | phenyl | 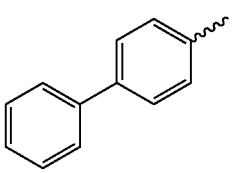 | phenyl | H |
| 4-13 | phenyl | 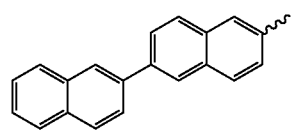 | phenyl | H |
| 4-14 | phenyl | 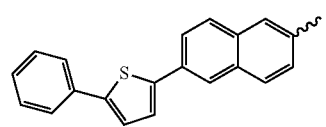 | phenyl | H |
| 4-15 | phenyl | 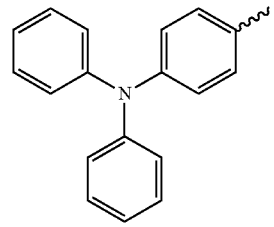 | phenyl | H |
| 4-16 | phenyl | 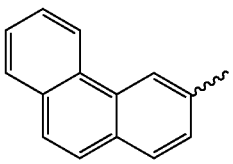 | phenyl | H |
| 4-17 | phenyl | 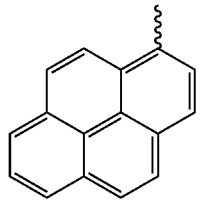 | phenyl | H |

TABLE 4-continued
| Formula | R1 | R2 | R4 | R3, R5, R6, X, R7 |
|---|---|---|---|---|
| 4-18 | phenyl | 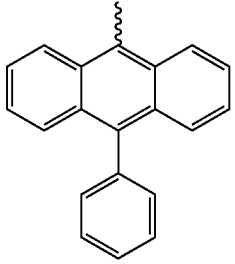 | phenyl | H |
| 4-19 | phenyl | 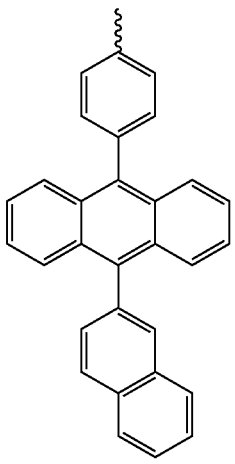 | phenyl | H |
| 4-20 | phenyl | 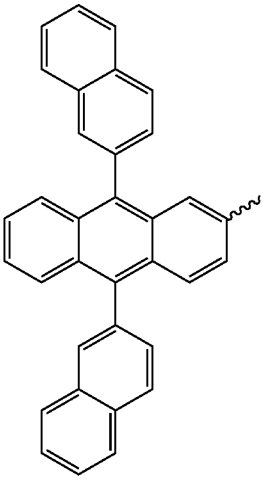 | phenyl | H |
| 4-21 | phenyl | 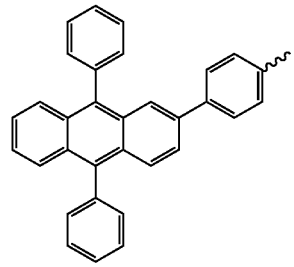 | phenyl | H |

TABLE 4-continued
| Formula | R1 | R2 | R4 | R3, R5, R6, X, R7 |
|---|---|---|---|---|
| 4-22 | phenyl | 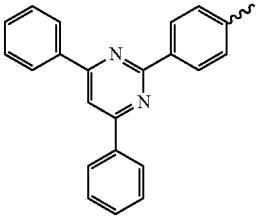 | phenyl | H |
| 4-23 | 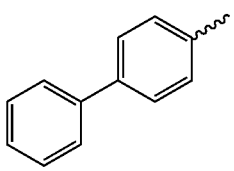 | phenyl | 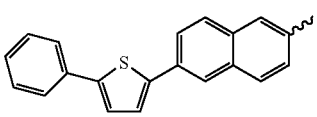 | H |
| 4-24 | 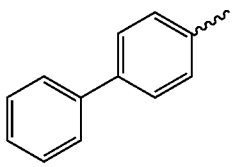 | phenyl | 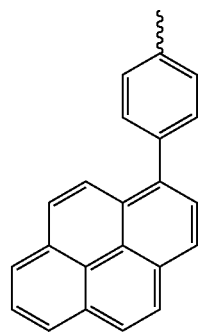 | H |
| 4-25 | 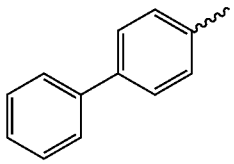 | phenyl | 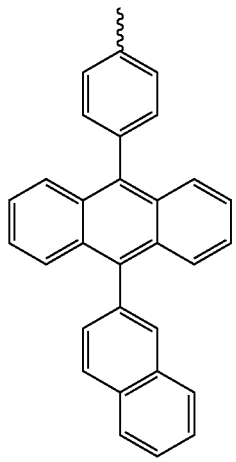 | H |
| 4-26 | 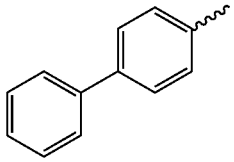 | phenyl | 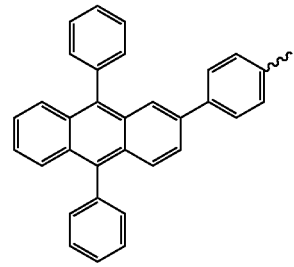 | H |

TABLE 4-continued
| Formula | R1 | R2 | R4 | R3, R5, R6, X, R7 |
|---|---|---|---|---|
| 4-27 | 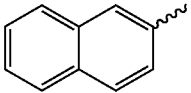 | phenyl | 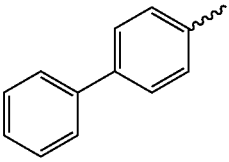 | H |
| 4-28 | 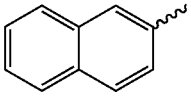 | phenyl | 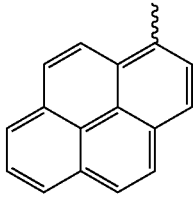 | H |
| 4-29 | 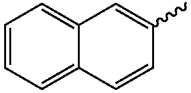 | phenyl | 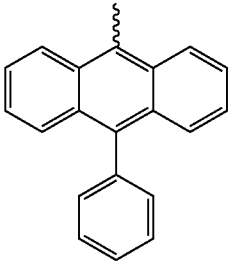 | H |
| 4-30 | 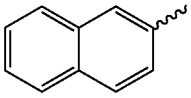 | phenyl | 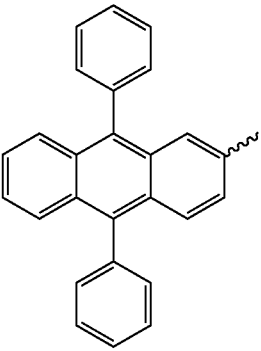 | H |
| 4-31 | 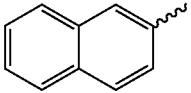 | phenyl | 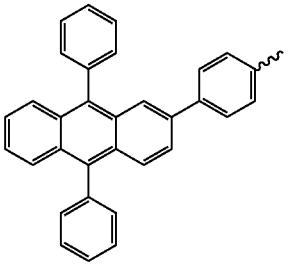 | H |
| 4-32 | 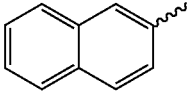 | phenyl | 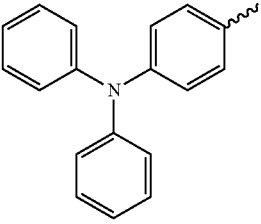 | H |

TABLE 4-continued
| Formula | R1 | R2 | R4 | R3, R5, R6, X, R7 |
|---|---|---|---|---|
| 4-33 | 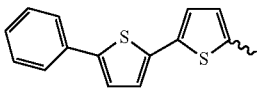 | phenyl | 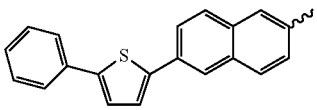 | H |
| 4-34 | 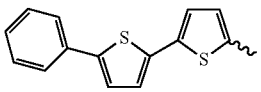 | phenyl | 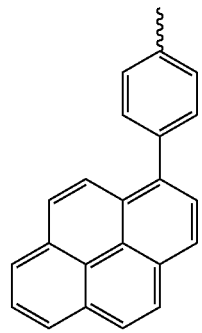 | H |
| 4-35 | 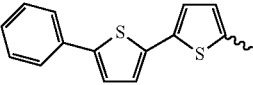 | phenyl | 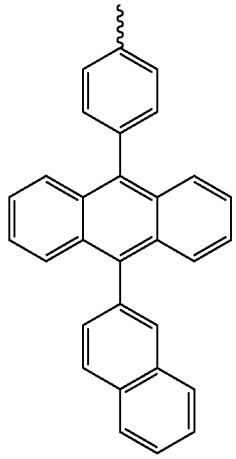 | H |
| 4-36 | 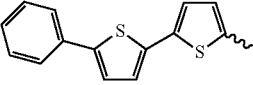 | phenyl | 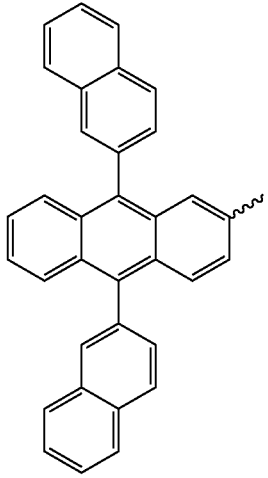 | H |

TABLE 4-continued

| Formula | R1 | R2 | R4 | R3, R5, R6, X, R7 |
|---|---|---|---|---|
| 4-37 | 5-phenylthiophen-2-yl-thiophene | phenyl | diphenylamino | H |
| 4-38 | pyren-1-yl | phenyl | 5-phenylthiophen-2-yl-naphthalene | H |
| 4-39 | pyren-1-yl | phenyl | 4-(pyren-1-yl)phenyl | H |
| 4-40 | pyren-1-yl | phenyl | 4-(10-(naphthalen-2-yl)anthracen-9-yl)phenyl | H |

TABLE 4-continued

| Formula | R1 | R2 | R4 | R3, R5, R6, X, R7 |
|---|---|---|---|---|
| 4-41 | pyrenyl | phenyl | 2,6-di(naphthalen-2-yl)anthracenyl | H |
| 4-42 | pyrenyl | phenyl | diphenylamino | H |
| 4-43 | 10-phenylanthracenyl | phenyl | biphenyl | H |
| 4-44 | 10-phenylanthracenyl | phenyl | pyrenyl | H |
| 4-45 | 10-phenylanthracenyl | phenyl | 10-phenylanthracenyl | H |

TABLE 4-continued
| Formula | R1 | R2 | R4 | R3, R5, R6, X, R7 |
|---|---|---|---|---|
| 4-46 | 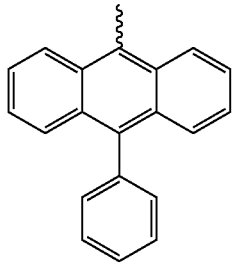 | phenyl | 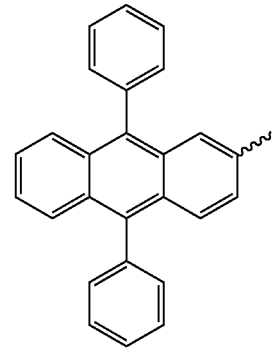 | H |
| 4-47 | 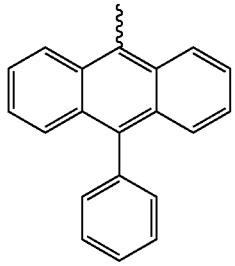 | phenyl | 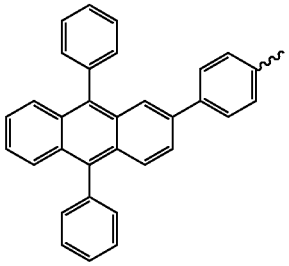 | H |
| 4-48 | 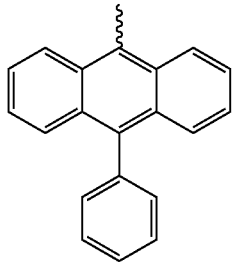 | phenyl | 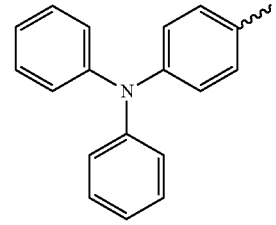 | H |
| 4-49 | 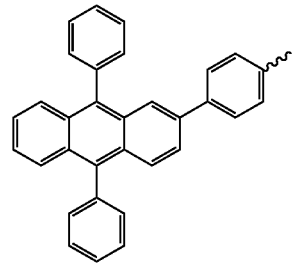 | phenyl | 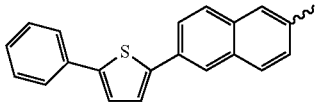 | H |
| 4-50 | 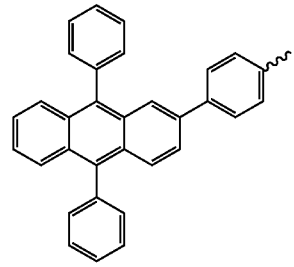 | phenyl | 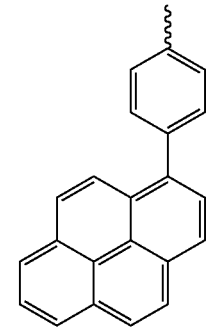 | H |

TABLE 4-continued

| Formula | R1 | R2 | R4 | R3, R5, R6, X, R7 |
|---|---|---|---|---|
| 4-51 | (9,10-diphenylanthracen-2-yl)phenyl | phenyl | 4-(10-(naphthalen-2-yl)anthracen-9-yl)phenyl | H |
| 4-52 | (9,10-diphenylanthracen-2-yl)phenyl | phenyl | 9,10-di(naphthalen-2-yl)anthracen-2-yl | H |
| 4-53 | (9,10-diphenylanthracen-2-yl)phenyl | phenyl | N,N-diphenylamino | H |

TABLE 5

| Formula | R1 | R2 | X | R3, R4, R5, R6, R7 |
|---|---|---|---|---|
| 5-1 | phenyl | phenyl | phenyl | H |
| 5-2 | phenyl | phenyl | naphthalen-2-yl | H |

TABLE 5-continued
| Formula | R1 | R2 | X | R3, R4, R5, R6, R7 |
|---|---|---|---|---|
| 5-3 | phenyl | phenyl | 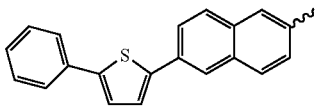 | H |
| 5-4 | phenyl | phenyl | 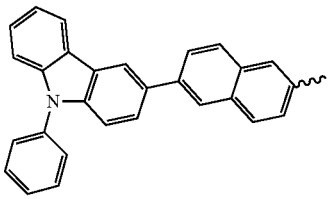 | H |
| 5-5 | phenyl | phenyl | 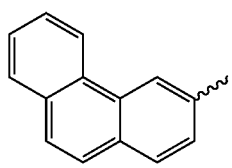 | H |
| 5-6 | phenyl | phenyl | 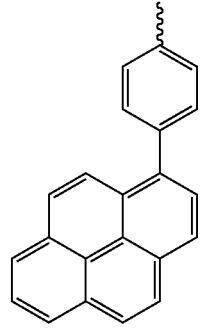 | H |
| 5-7 | phenyl | phenyl | 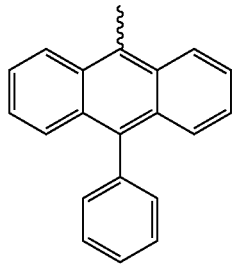 | H |
| 5-8 | phenyl | phenyl | 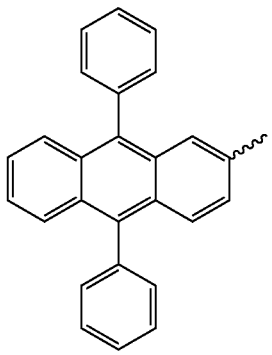 | H |

TABLE 5-continued
| Formula | R1 | R2 | X | R3, R4, R5, R6, R7 |
|---|---|---|---|---|
| 5-9 | phenyl | phenyl | 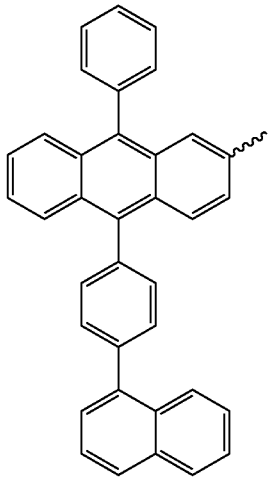 | H |
| 5-10 | phenyl | phenyl | 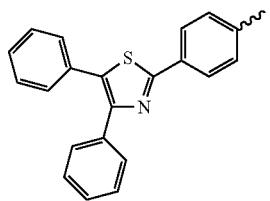 | H |
| 5-11 | phenyl | 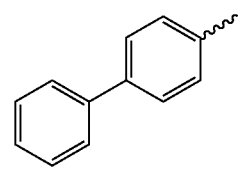 | phenyl | H |
| 5-12 | phenyl | 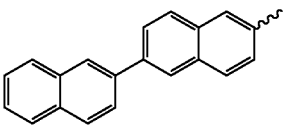 | phenyl | H |
| 5-13 | phenyl | 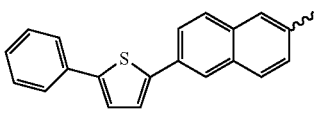 | phenyl | H |
| 5-14 | phenyl | 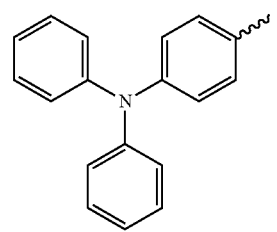 | phenyl | H |
| 5-15 | phenyl | 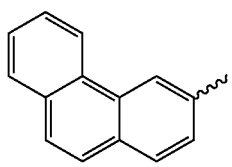 | phenyl | H |

TABLE 5-continued
| Formula | R1 | R2 | X | R3, R4, R5, R6, R7 |
|---|---|---|---|---|
| 5-16 | phenyl | 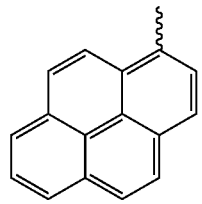 | phenyl | H |
| 5-17 | phenyl | 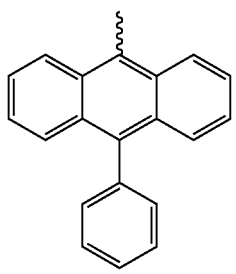 | phenyl | H |
| 5-18 | phenyl | 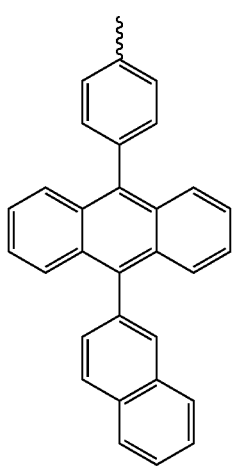 | phenyl | H |
| 5-19 | phenyl | 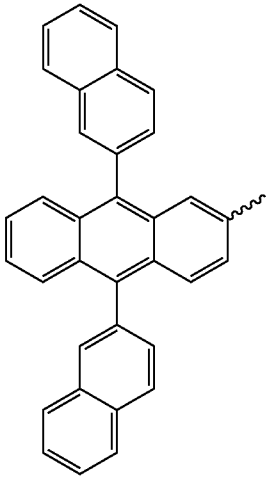 | phenyl | H |

TABLE 5-continued
| Formula | R1 | R2 | X | R3, R4, R5, R6, R7 |
|---|---|---|---|---|
| 5-20 | phenyl | 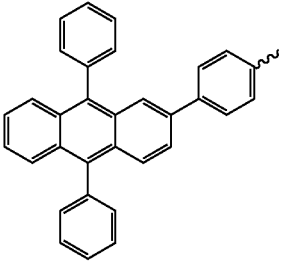 | phenyl | H |
| 5-21 | phenyl | 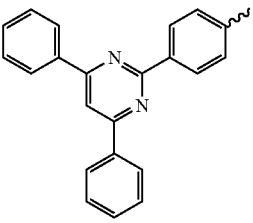 | phenyl | H |
| 5-22 | 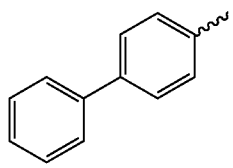 | phenyl | 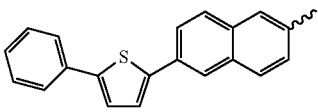 | H |
| 5-23 | 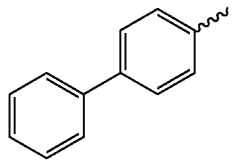 | phenyl | 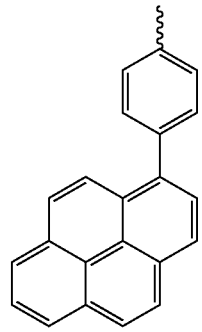 | H |
| 5-24 | 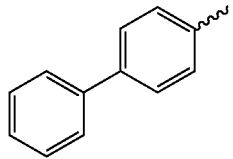 | phenyl | 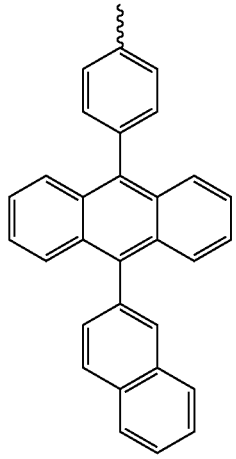 | H |

TABLE 5-continued

| Formula | R1 | R2 | X | R3, R4, R5, R6, R7 |
|---|---|---|---|---|
| 5-25 | biphenyl | phenyl | 9,10-diphenylanthracen-2-yl-phenyl | H |
| 5-26 | naphthyl | phenyl | biphenyl | H |
| 5-27 | naphthyl | phenyl | pyrenyl | H |
| 5-28 | naphthyl | phenyl | 10-phenylanthracen-9-yl | H |
| 5-29 | naphthyl | phenyl | 9,10-diphenylanthracen-2-yl | H |
| 5-30 | naphthyl | phenyl | 9,10-diphenylanthracen-2-yl-phenyl | H |

TABLE 5-continued
| Formula | R1 | R2 | X | R3, R4, R5, R6, R7 |
|---|---|---|---|---|
| 5-31 | 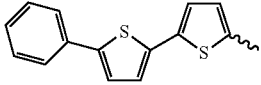 | phenyl | 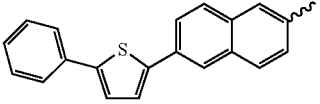 | H |
| 5-32 | 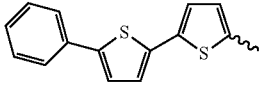 | phenyl | 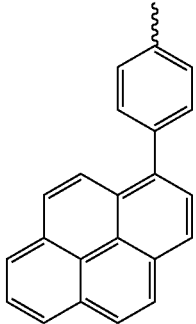 | H |
| 5-33 | 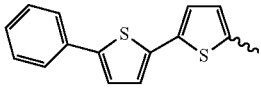 | phenyl | 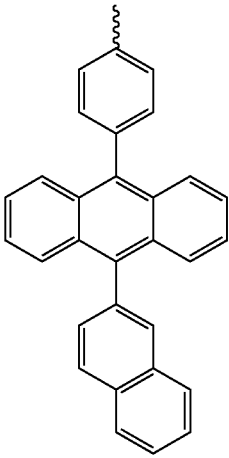 | H |
| 5-34 | 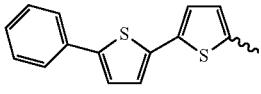 | phenyl | 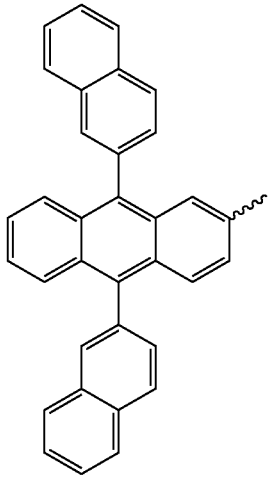 | H |

TABLE 5-continued
| Formula | R1 | R2 | X | R3, R4, R5, R6, R7 |
|---|---|---|---|---|
| 5-35 | 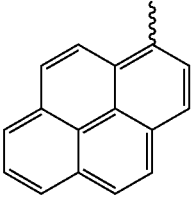 | phenyl | 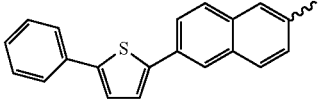 | H |
| 5-36 | 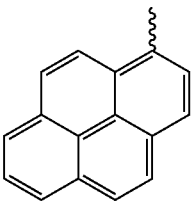 | phenyl | 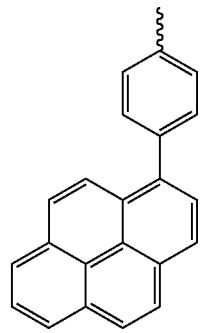 | H |
| 5-37 | 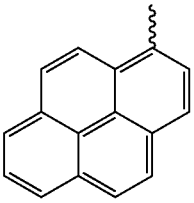 | phenyl | 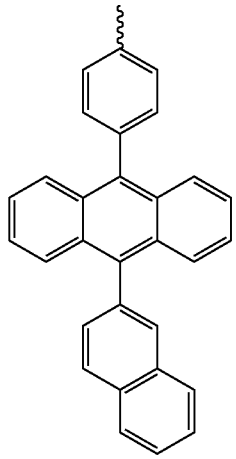 | H |
| 5-38 | 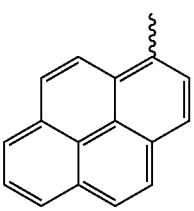 | phenyl | 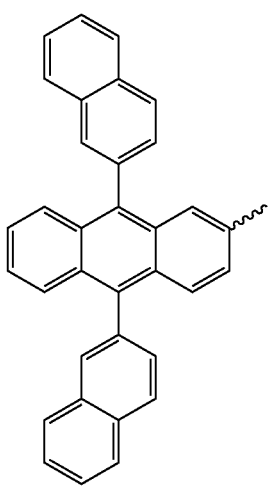 | H |

TABLE 5-continued
| Formula | R1 | R2 | X | R3, R4, R5, R6, R7 |
|---|---|---|---|---|
| 5-39 | 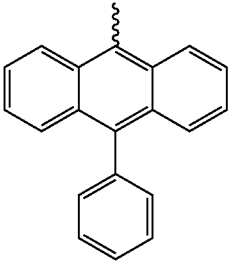 | phenyl | 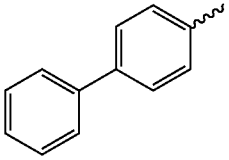 | H |
| 5-40 | 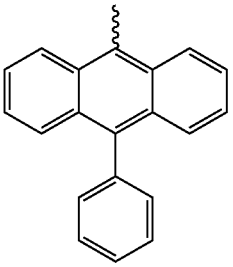 | phenyl | 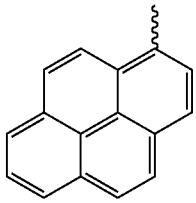 | H |
| 5-41 | 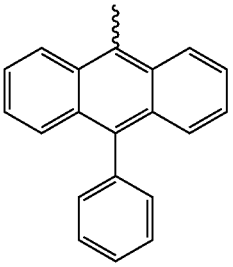 | phenyl | 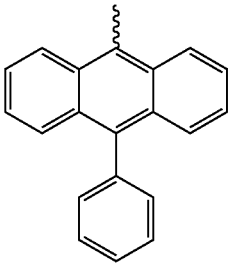 | H |
| 5-42 | 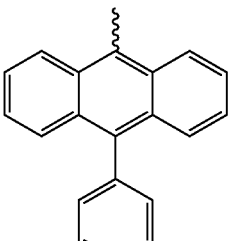 | phenyl | 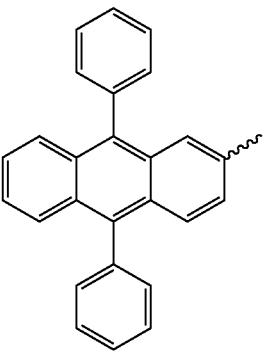 | H |
| 5-43 | 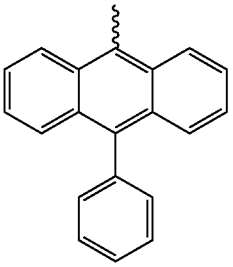 | phenyl | 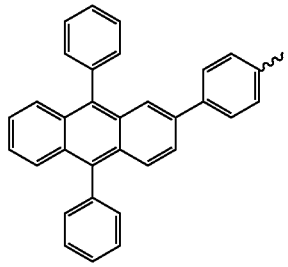 | H |

TABLE 5-continued
| Formula | R1 | R2 | X | R3, R4, R5, R6, R7 |
|---|---|---|---|---|
| 5-44 | 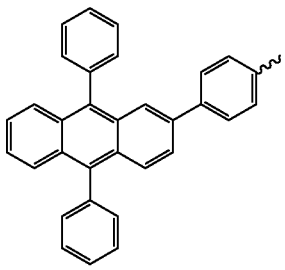 | phenyl | 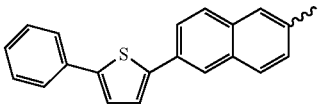 | H |
| 5-45 | 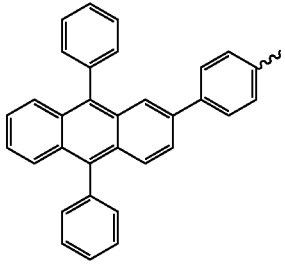 | phenyl | 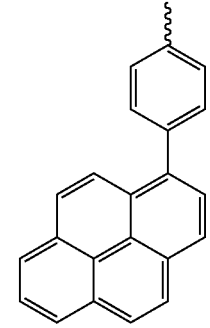 | H |
| 5-46 | 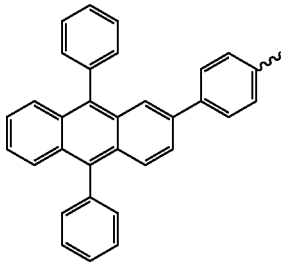 | phenyl | 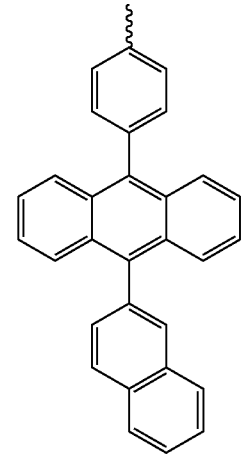 | H |
| 5-47 | 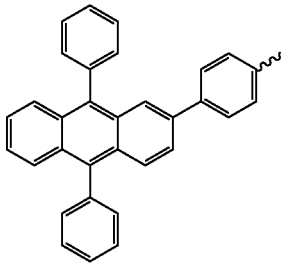 | phenyl | 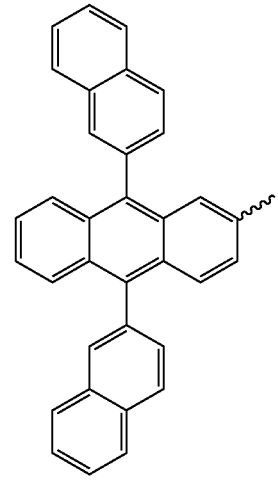 | H |

TABLE 6
| Formula | R1 | R2 | R7 | R3, R4, R5, R6, X |
|---|---|---|---|---|
| 6-1 | phenyl | phenyl | phenyl | H |
| 6-2 | phenyl | phenyl | 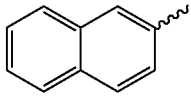 | H |
| 6-3 | phenyl | phenyl | 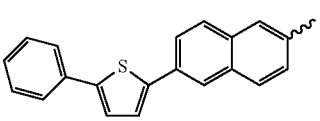 | H |
| 6-4 | phenyl | phenyl | 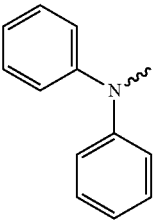 | H |
| 6-5 | phenyl | phenyl | 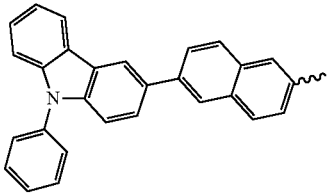 | H |
| 6-6 | phenyl | phenyl | 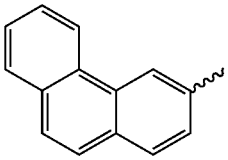 | H |
| 6-7 | phenyl | phenyl | 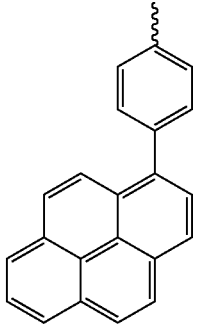 | H |
| 6-8 | phenyl | phenyl | 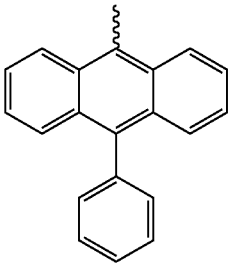 | H |

TABLE 6-continued

| Formula | R1 | R2 | R7 | R3, R4, R5, R6, X |
|---|---|---|---|---|
| 6-9 | phenyl | phenyl | 9,10-diphenylanthracen-2-yl | H |
| 6-10 | phenyl | phenyl | 4-(9,10-diphenylanthracen-2-yl)phenyl-linked naphthalen-1-yl | H |
| 6-11 | phenyl | phenyl | 4-(4,5-diphenylthiazol-2-yl)phenyl | H |
| 6-12 | phenyl | biphenyl-4-yl | phenyl | H |
| 6-13 | phenyl | [2,2'-binaphthalen]-6-yl | phenyl | H |
| 6-14 | phenyl | 6-(5-phenylthiophen-2-yl)naphthalen-2-yl | phenyl | H |

TABLE 6-continued

| Formula | R1 | R2 | R7 | R3, R4, R5, R6, X |
|---|---|---|---|---|
| 6-15 | phenyl | triphenylamine (4-yl) | phenyl | H |
| 6-16 | phenyl | phenanthren-2-yl | phenyl | H |
| 6-17 | phenyl | pyren-1-yl | phenyl | H |
| 6-18 | phenyl | 10-phenylanthracen-9-yl | phenyl | H |
| 6-19 | phenyl | 4-(10-(naphthalen-2-yl)anthracen-9-yl)phenyl | phenyl | H |

TABLE 6-continued
| Formula | R1 | R2 | R7 | R3, R4, R5, R6, X |
|---|---|---|---|---|
| 6-20 | phenyl | 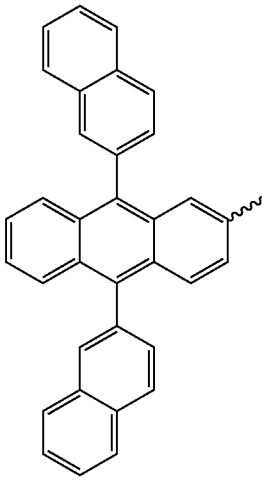 | phenyl | H |
| 6-21 | phenyl | 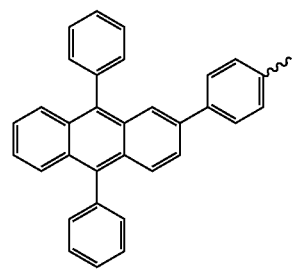 | phenyl | H |
| 6-22 | phenyl | 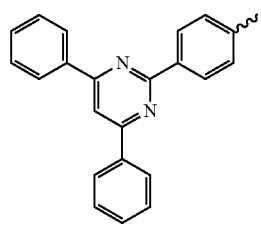 | phenyl | H |
| 6-23 | 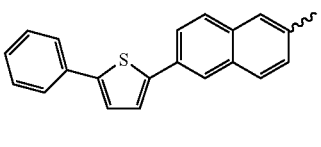 | phenyl | 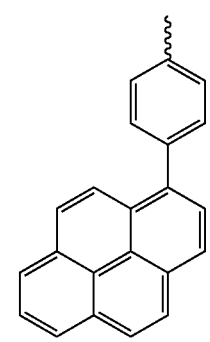 | H |
| 6-24 | 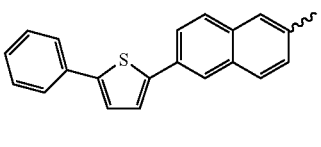 | phenyl | 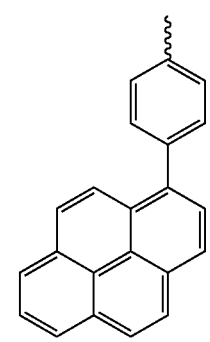 | H |

TABLE 6-continued

| Formula | R1 | R2 | R7 | R3, R4, R5, R6, X |
|---|---|---|---|---|
| 6-25 | 4-biphenyl | phenyl | 10-(naphthalen-2-yl)anthracen-9-yl (via phenyl linker) | H |
| 6-26 | 4-biphenyl | phenyl | 4-(9,10-diphenylanthracen-2-yl)phenyl | H |
| 6-27 | naphthalen-2-yl | phenyl | 4-biphenyl | H |
| 6-28 | naphthalen-2-yl | phenyl | pyren-1-yl | H |
| 6-29 | naphthalen-2-yl | phenyl | 10-phenylanthracen-9-yl | H |

TABLE 6-continued

| Formula | R1 | R2 | R7 | R3, R4, R5, R6, X |
|---|---|---|---|---|
| 6-30 | 2-naphthyl | phenyl | 9,10-diphenylanthracen-2-yl | H |
| 6-31 | 2-naphthyl | phenyl | 4-(9,10-diphenylanthracen-2-yl)phenyl | H |
| 6-32 | 2-naphthyl | phenyl | 4-(diphenylamino)phenyl | H |
| 6-33 | 5'-phenyl-2,2'-bithiophen-5-yl | phenyl | 6-(5-phenylthiophen-2-yl)naphthalen-2-yl | H |
| 6-34 | 5'-phenyl-2,2'-bithiophen-5-yl | phenyl | 4-(pyren-1-yl)phenyl | H |

TABLE 6-continued
| Formula | R1 | R2 | R7 | R3, R4, R5, R6, X |
|---|---|---|---|---|
| 6-35 | 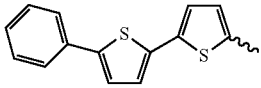 | phenyl | 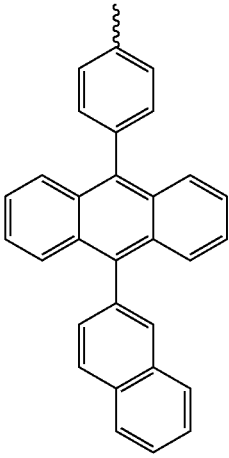 | H |
| 6-36 | 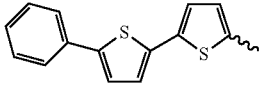 | phenyl | 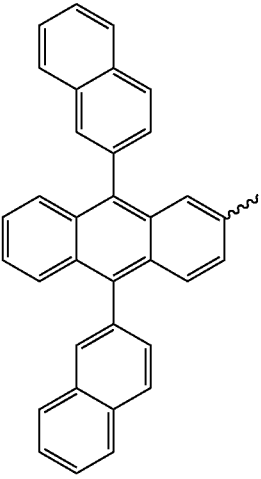 | H |
| 6-37 | 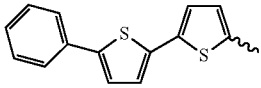 | phenyl | 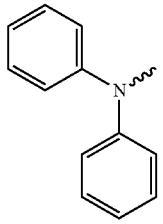 | H |
| 6-38 | 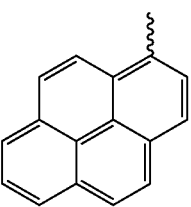 | phenyl | 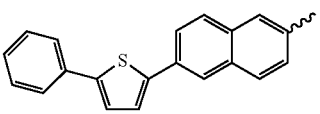 | H |

TABLE 6-continued

| Formula | R1 | R2 | R7 | R3, R4, R5, R6, X |
|---|---|---|---|---|
| 6-39 | pyrenyl | phenyl | 4-(pyren-1-yl)phenyl | H |
| 6-40 | pyrenyl | phenyl | 4-(10-(naphthalen-2-yl)anthracen-9-yl)phenyl | H |
| 6-41 | pyrenyl | phenyl | 9,10-di(naphthalen-2-yl)anthracen-2-yl | H |
| 6-42 | pyrenyl | phenyl | diphenylamino | H |

TABLE 6-continued
| Formula | R1 | R2 | R7 | R3, R4, R5, R6, X |
|---|---|---|---|---|
| 6-43 | 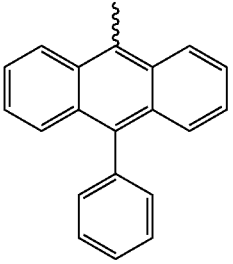 | phenyl | 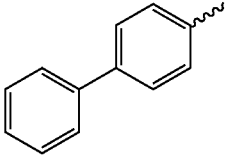 | H |
| 6-44 | 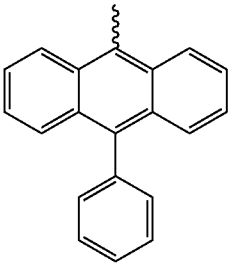 | phenyl | 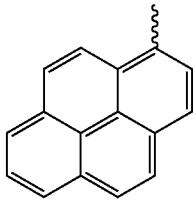 | H |
| 6-45 | 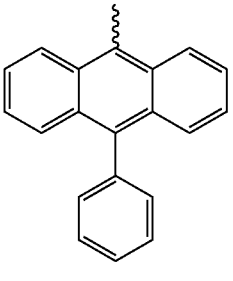 | phenyl | 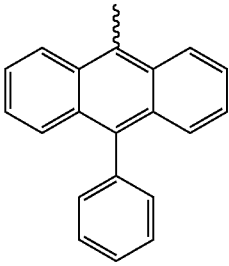 | H |
| 6-46 | 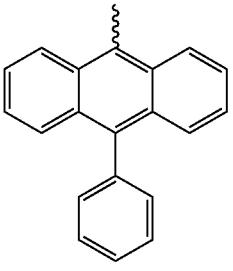 | phenyl | 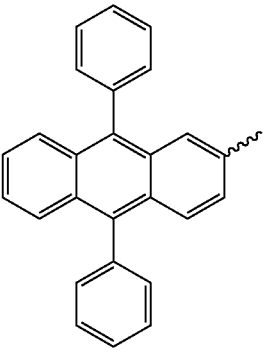 | H |
| 6-47 | 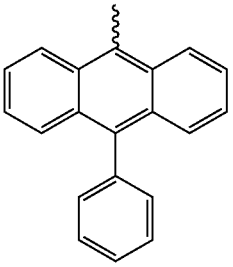 | phenyl | 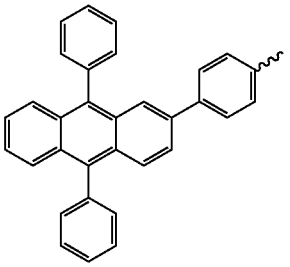 | H |

TABLE 6-continued

| Formula | R1 | R2 | R7 | R3, R4, R5, R6, X |
|---|---|---|---|---|
| 6-48 | 9-phenylanthracen-10-yl | phenyl | 4-(diphenylamino)phenyl | H |
| 6-49 | 2-(9,10-diphenylanthracen-2-yl)phenyl | phenyl | 6-(5-phenylthiophen-2-yl)naphthalen-2-yl | H |
| 6-50 | 2-(9,10-diphenylanthracen-2-yl)phenyl | phenyl | 4-(pyren-1-yl)phenyl | H |
| 6-51 | 2-(9,10-diphenylanthracen-2-yl)phenyl | phenyl | 4-(10-(naphthalen-2-yl)anthracen-9-yl)phenyl | H |

TABLE 6-continued

| Formula | R1 | R2 | R7 | R3, R4, R5, R6, X |
|---|---|---|---|---|
| 6-52 | 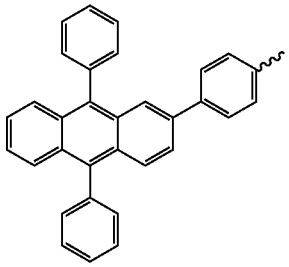 | phenyl | 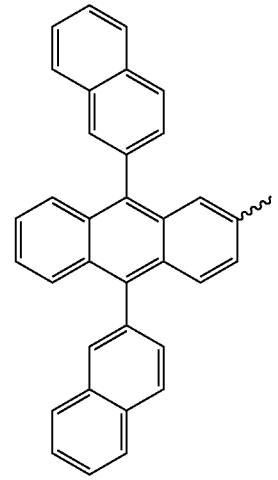 | H |
| 6-53 | 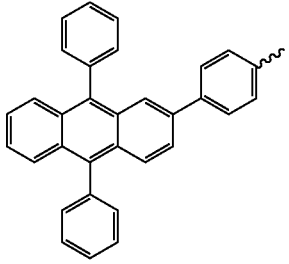 | phenyl | 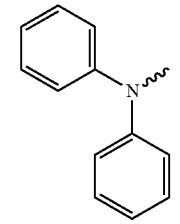 | H |

In addition, in Formula 1, X and R3 to R7 may be hydrogen.

The compound that is represented by Formula 1 may be manufactured according to the following method. First, the compound A is manufactured according to the method of Journal of Organic Chemistry 2005, 70, 3511-3517, and the manufacturing is described below.

[Reaction Equation 1]

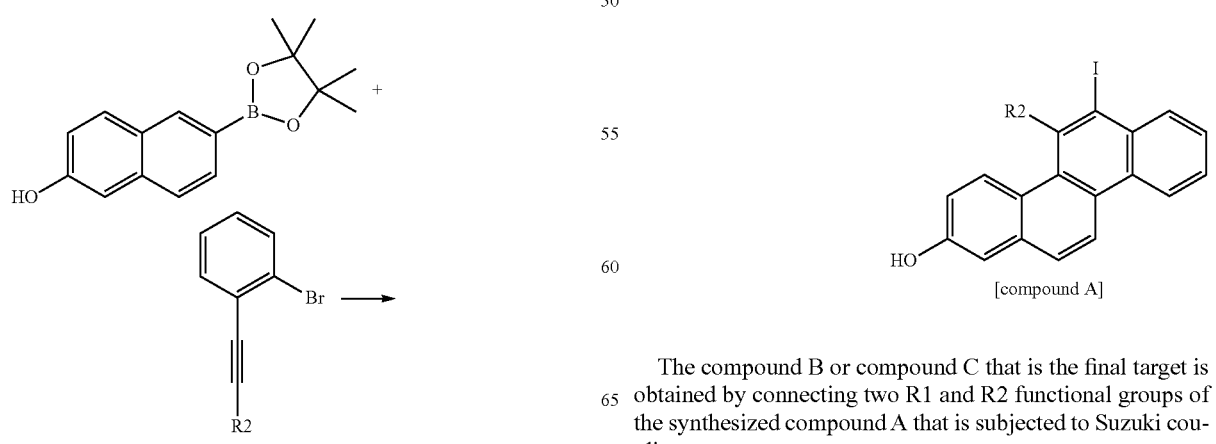

[compound A]

The compound B or compound C that is the final target is obtained by connecting two R1 and R2 functional groups of the synthesized compound A that is subjected to Suzuki coupling.

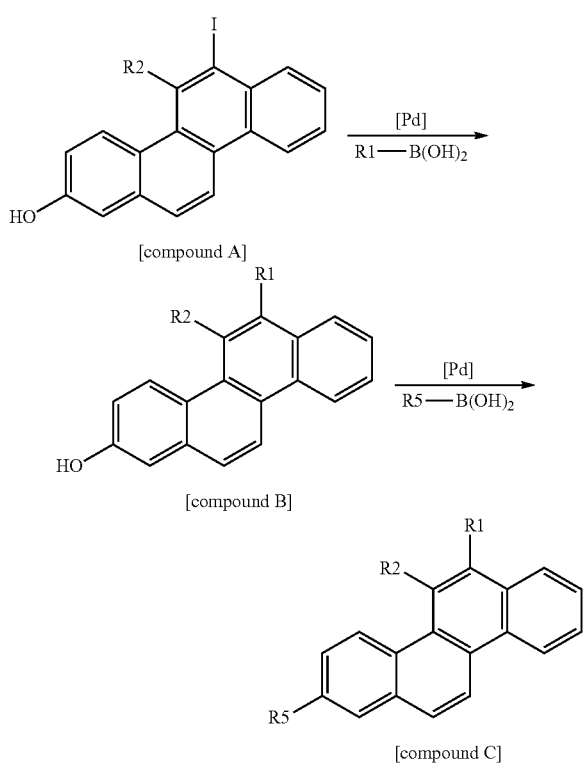

A second aspect of the present invention relates to an organic electronic device which comprises a first electrode, a second electrode, and one or more organic material layers that are disposed between the first electrode and the second electrode, wherein one or more layers of the organic material layers comprise the compound that is represented by Formula 1.

Herein, the organic material layer may comprise a hole injection layer and a hole transport layer, and the hole injection layer and the hole transport layer may comprise the compound that is represented by Formula 1.

In addition, the organic material layer comprises a light emitting layer, and the light emitting layer comprises the compound of Formula 1.

In addition, the organic material layer comprises an electron transport layer, and the electron transport layer comprises the compound of Formula 1.

At this time, it is preferable that the organic electronic device is selected from the group consisting of an organic light emitting device, an organic solar cell, an organic photoconductor (OPC), and an organic transistor.

The compound that is represented by Formula 1 may be formed to the organic material layer by using a vacuum deposition method and a solution coating method when the organic electronic device is manufactured. In connection with this, illustrative, but non-limiting, examples of the solution coating process comprise a spin coating process, a dip coating process, an inkjet printing process, a screen printing process, a spray process, and a roll coating process.

The organic electronic device of the present invention may be produced using known materials through a known process, modified only in that at least one layer of organic material layer(s) comprise the compound of the present invention, that is, the compound of Formula 1.

The organic material layer of the organic electronic device according to the present invention may have a single layer structure, or a multilayered structure in which two or more organic material layers are layered. For example, the organic electronic device according to the present invention may have a structure that comprises a hole injection layer, a hole transport layer, a light emitting layer, an electron transport layer, and an electron injection layer as an organic material layer. However, the structure of the organic electronic device is not limited to this, but may comprise a smaller number of organic material layers.

Furthermore, the organic electronic device of the present invention may be produced, for example, by sequentially layering a first electrode, organic material layer(s), and a second electrode on a substrate. In connection with this, a physical vapor deposition (PVD) method, such as a sputtering method or an e-beam evaporation method, may be used, but the method is not limited to these.

As the anode material, in general, it is preferable to use the material having the large work function so as to smoothly perform hole injection into the organic material layer. As examples of the anode material that is capable of being used in the present invention, there are metal or alloy thereof such as vanadium, chrome, copper, zinc, gold and the like; metal oxides such as zinc oxides, indium oxides, indium tin oxides (ITO), indium zinc oxides (IZO) and the like; a combination of metal and oxides such as ZnO:Al or $SnO_2$:Sb; conductive polymers such as poly(3-methyl compound), poly[3,4-(ethylene-1,2-dioxy) compound](PEDT), polypyrole and polyaniline, but it is not limited thereto.

As the cathode material, in general, it is preferable to use the material having the small work function so as to smoothly perform electron injection into the organic material layer. As detailed examples of the cathode material, there are metal such as magnesium, calcium, sodium, potassium, titanium, indium, yttrium, lithium, gadolinium, aluminum, silver, tin, and lead or an alloy thereof; a multilayered structure material such as LiF/Al or $LiO_2$/Al, but it is not limited thereto.

The hole injection material is a material that is capable of well receiving holes from the anode at a low voltage, and it is preferable that the HOMO (highest occupied molecular orbital) of the hole injection material is a value between the work function of the anode material and the HOMO of the organic material layer around them. As detailed examples of the hole injecting material, there are organic materials of metal porphyrin, oligothiophene and arylamine series, organic materials of hexanitrile hexaazatriphenylene and quinacridone series, organic materials of perylene series, and conductive polymers of anthraquinone, polyaniline, and polythiophene series, but they are not limited thereto.

The hole transport material is a material that receives the holes from the anode or the hole injection layer and transfer them to the light emitting layer, and it is preferable to use the material having the large mobility to the holes. As detailed examples thereof, there are arylamine-based organic material, a conductive polymer, and a block copolymer in which a conjugate portion and a conjugate portion are simultaneously comprised, but it is not limited thereto.

The light emitting material is a material that receives the holes and the electrons from the hole transport layer and the electron transport layer, combines them, such that light at a range of visible rays is emitted, and it is preferable to use the material having excellent photon efficiency to fluorescence or phosphorescence. As detailed examples thereof, there are a 8-hydroxy-quinoline aluminum complex ($Alq_3$); a carbazole-based compound; a dimerized styryl compound; BAlq; 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but it is not limited thereto.

The hole transport material is a material that receives the holes from the anode or the hole injection layer and transfer them to the light emitting layer, and it is preferable to use the material having the large mobility to the holes. As detailed examples thereof, there are a 8-hydroxyquinoline Al complex; a complex comprising $Alq_3$; an organic radical compound; a hydroxyflavone metal complex and the like, but it is not limited thereto.

The organic light emitting device according to the present invention may be a top emission type, a bottom emission type, or a both-sided emission type according to the used material.

The compound according to the present invention may be applied to an organic electronic device such as an organic solar cell, an organic photoconductor, an organic transistor and the like by the principle that is similar to the principle of the organic light emitting device.

MODE FOR INVENTION

The method for manufacturing the compound of Formula 1 and the manufacturing of an organic light emitting device using the same will be described in detail in Preparation Examples and Examples. However, the Preparation Examples and Examples are set forth to illustrate the present invention, but the scope of the present invention is not limited thereto.

PREPARATION EXAMPLE

In general, the compound of Formula 1 according to the present invention can be manufactured with multistage chemical reactions. That is, some intermediate compounds are first manufactured, and the compounds of Formula 1 are manufactured from the intermediate compounds. The exemplified intermediate compounds are the following compounds. In the compounds, "Br" may be substituted by any other reactive atom or functional group.

[compound S-1]

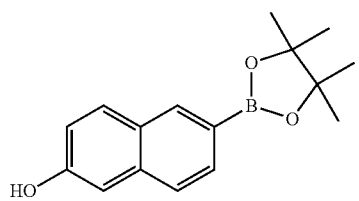

[compound S-2]

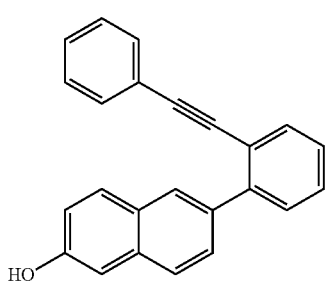

[compound A-1]

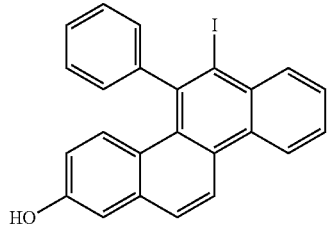

[compound B-1]

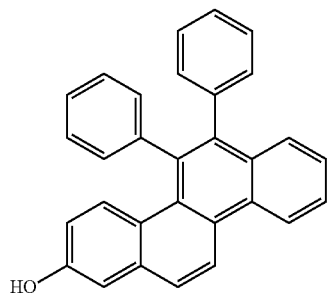

[compound S-3]

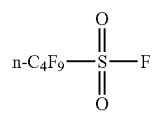

[compound C-1]

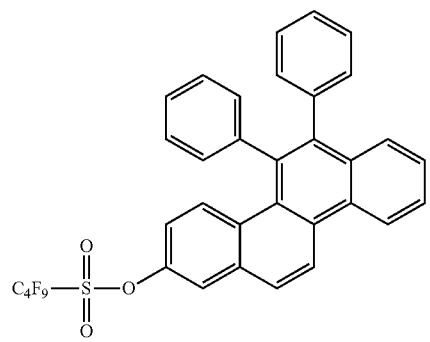

[compound B-2]

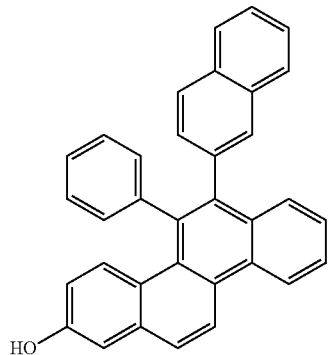

[compound C-2]

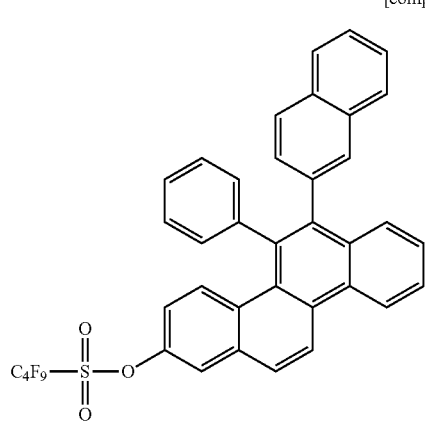

[compound S-4]

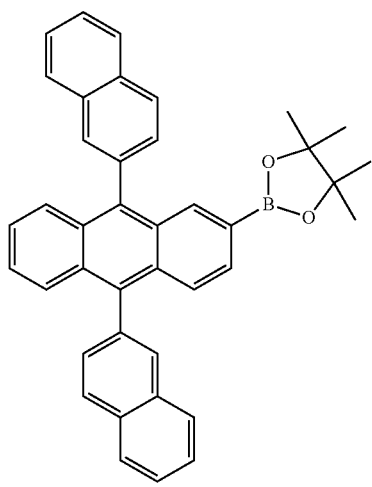

[compound S-5]

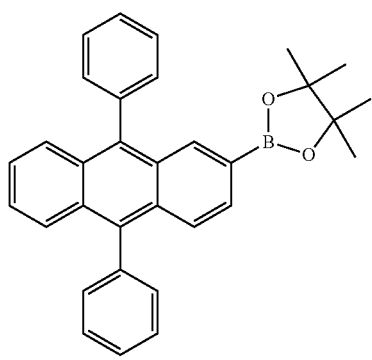

[compound S-6]

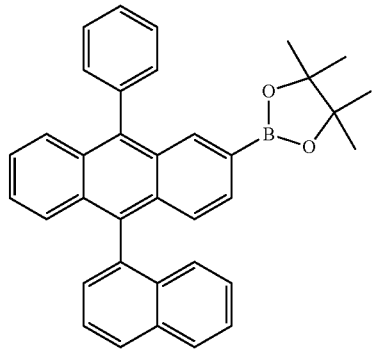

Molecular Weight = 506.46

[compound S-7]

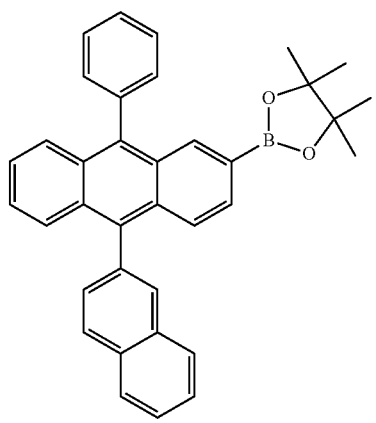

Molecular Weight = 506.46

[compound S-8]

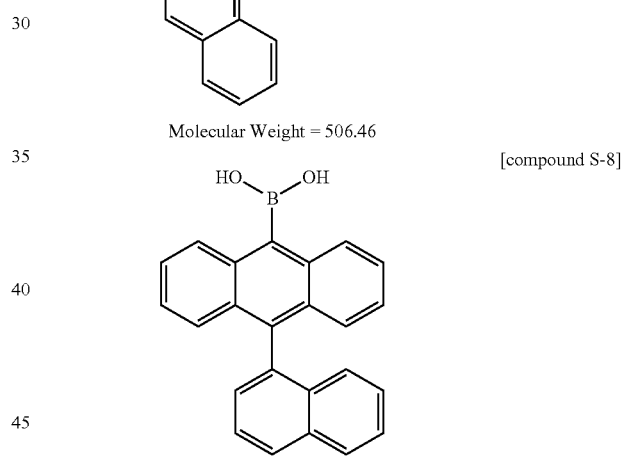

Molecular Weight = 348.21

Preparation Example 1

Preparation of the Compound S-2

1-bromo-2-(2-phenylethynyl)-benzene (10 g, 38.9 mmol), the compound S-1 (10.5 g, 38.9 mmol), and potassium phosphate ($K_3PO_4$, 24.7 g, 116.5 mmol) were suspended in the mixture of THF (200 mL) and water (200 mL). To the suspension solution, tetrakis(triphenylphosphine)palladium (898 mg, 1.83 mmol) was applied. The mixture was refluxed and agitated for about 24 hours, and the refluxed mixture was cooled to room temperature. The organic material layer was separated, washed with water, and the aqueous layer was extracted with chloroform. The organic extract was dried on magnesium sulfate and concentrated under the vacuum to synthesize the compound S-2 (10.5 g, yield 84%).

Preparation Example 2

Preparation of the Compound A-1

After the compound S-2 (10.7 g, 33.4 mmol) that was manufactured in Preparation Example 1 was dissolved in CHCl$_3$ (100 mL), ICl (33.4 mL, 1M sol, 33.4 mmol), slowly dropped, and agitated for 12 hours. The formed solid was filtered, washed with hexane, and dried to prepare the compound A-1 (7.02 g, yield 47%).

Preparation Example 3

Preparation of the Compound B-1

The compound A-1 (7.02 g, 15.7 mmol) that was manufactured in Preparation Example 2, phenyl boronic acid (2.30 g, 18.9 mmol), and potassium phosphate (K$_3$PO$_4$, 6.67 g, 31.4 mmol) were suspended in the mixture of THF (200 mL) and water (50 mL). To the suspension solution, tetrakis(triphenylphosphine)palladium (363 mg, 0.31 mmol) was applied. The mixture was refluxed and agitated for about 24 hours, and the refluxed mixture was cooled to room temperature. The organic material layer was separated, washed with water, and the aqueous layer was extracted with chloroform. The organic extract was dried on magnesium sulfate and concentrated under the vacuum to prepare the compound B-1. The B-1 was not purified and used in Preparation Example 4.

Preparation Example 4

Preparation of the Compound C-1

The compound B-1 (6.2 g, 15.6 mmol) that was manufactured in Preparation Example 3, S-3 (5.22 g, 17.3 mmol) and potassium carbonate (6.10 g, 46.9 mmol) were suspended in the mixture of THF (100 mL) and water (100 mL). The mixture was maintained for about 24 hours at 50° C. This mixture was cooled to room temperature. The separated organic layer was dried on magnesium sulfate and concentrated. Thereafter, it was recrystallized on chloroform and methyl alcohol to obtain the compound C-1 (4.85 g, 47%).

Preparation Example 5

Preparation of the Compound 1-18

The compound C-1 (4.85 g, 7.1 mmol) that was manufactured in Preparation Example 4, the compound S-4 (3.98 g, 7.1 mmol), and potassium phosphate (K$_3$PO$_4$, 3.0 g, 14.2 mmol) were suspended in the mixture of THF (100 mL) and water (100 mL). To the suspension solution, tetrakis(triphenylphosphine)palladium (165 mg, 0.143 mmol) was applied. The mixture was refluxed and agitated for about 24 hours, and the refluxed mixture was cooled to room temperature. The organic material layer was separated, washed with water, and the aqueous layer was extracted with chloroform. The organic extract was dried on magnesium sulfate and recrystallized on THF/ethyl acetate to obtain the compound 1-18 (4.18 g, 73%).

[M+H]+=809

Preparation Example 6

Preparation of the Compound B-2

The compound A-1 (6.00 g, 13.4 mmol) that was manufactured in Preparation Example 2, naphthalene 2-boronic acid (2.77 g, 16.1 mmol), and potassium phosphate (K$_3$PO$_4$, 5.68 g, 26.8 mmol) were suspended in the mixture of THF (100 mL) and water (50 mL). To the suspension solution, tetrakis (triphenylphosphine)palladium (309 mg, 0.27 mmol) was applied. The mixture was refluxed and agitated for about 24 hours, and the refluxed mixture was cooled to room temperature. The organic material layer was separated, washed with water, and the aqueous layer was extracted with chloroform. The organic extract was dried on magnesium sulfate and concentrated under the vacuum to prepare the compound B-2. The B-2 was not purified and used in Preparation Example 7.

Preparation Example 7

Preparation of the Compound C-2

The compound B-2 (5.98 g, 13.4 mmol) that was manufactured in Preparation Example 6, S-3 (4.45 g, 14.7 mmol) and potassium carbonate (3.49 g, 26.8 mmol) were suspended in the mixture of THF (100 mL) and water (100 mL). The mixture was maintained for about 24 hours at 50° C. This mixture was cooled to room temperature. The separated organic layer was dried on magnesium sulfate and concentrated. Thereafter, it was recrystallized on chloroform and methyl alcohol to obtain the compound C-2 (5.86 g, 40%).

Preparation Example 8

Preparation of the Compound 1-61

The compound C-2 (5.86 g, 8.0 mmol) that was manufactured in Preparation Example 7, the compound S-5 (3.65 g, 8.0 mmol), and potassium phosphate (K$_3$PO$_4$, 3.39 g, 16.0 mmol) were suspended in the mixture of THF (100 mL) and water (100 mL). To the suspension solution, tetrakis(triphenylphosphine)palladium (200 mg, 0.173 mmol) was applied. The mixture was refluxed and agitated for about 24 hours, and the refluxed mixture was cooled to room temperature. The organic material layer was separated, washed with water, and the aqueous layer was extracted with chloroform. The organic extract was dried on magnesium sulfate and recrystallized on THF/ethyl acetate to obtain the compound 1-61 (5.25 g, 86%).

[M+H]+=759

Preparation Example 9

Preparation of the Compound 1-6

The compound 1-6 (6.9 g, 91%) was manufactured by using the same method as Preparation Example 5, except that the compound S-6 (5.1 g, 10.0 mmol) was used instead of the compound S-4 in Preparation Example 5.

MS: [M+H]+=759

Preparation Example 10

Preparation of the Compound 1-7

The compound 1-7 (4.8 g, 73%) was manufactured by using the same method as Preparation Example 5, except that the compound S-7 (4.4 g, 8.7 mmol) was used instead of the compound S-4 in Preparation Example 5.

MS: [M+H]+=759

Preparation Example 11

Preparation of the Compound 1-14

The compound 1-14 (7.3 g, 89%) was manufactured by using the same method as Preparation Example 5, except that the compound S-8 (4.2 g, 12.0 mmol) was used instead of the compound S-4 in Preparation Example 5.

MS: [M+H]+=683

EXAMPLE

Examples 1-1

A glass substrate on which a thin film of ITO (indium tin oxide) was coated to a thickness of 1,500 Å was immersed in distilled water having a detergent dissolved therein to wash the substrate with ultrasonic waves. At this time, the detergent as used herein was a product commercially available from Fisher Co. and the distilled water was one which had been twice filtered by using a filter commercially available from Millipore Co. ITO was washed for 30 minutes, and then washing with ultrasonic waves was repeated twice for 10 minutes by using distilled water. After the completion of washing with distilled water, washing with ultrasonic waves was subsequently carried out by using solvents such as isopropyl alcohol, acetone and methanol, the resultant product was dried, and transported to the plasma washing machine. In addition, the substrate was washed by using the oxygen plasma for 5 min, and the substrate was transported to the vacuum deposition machine.

On the ITO transparent electrode thus prepared, hexanitrile hexaazatriphenylene was coated to thicknesses of 500 Å by thermal vacuum deposition to form a hole injecting layer. After NPB (400 Å) that was the hole transport material was deposited under the vacuum state thereon, the host compound 1-18 and the dopant D1 compound were deposited under the vacuum state in a thickness of 300 Å as a light emitting layer. The electron injection and transport layers were formed by depositing the following E1 compound on the light emitting layer under the vacuum in a thickness of 200 Å. On the electron injection and transport layer, lithium fluoride (LiF) in a thickness of 12 Å and aluminum in a thickness of 2,000 Å were subsequently deposited to form a cathode. In the above process, the deposition speed of the organic substance was maintained at 1 Å/sec, that of lithium fluoride was maintained at 0.2 Å/sec, and that of aluminum was maintained at 3 to 7 Å/sec. Properties of the manufactured organic light emitting device were evaluated, and the results are described in the following Table 7.

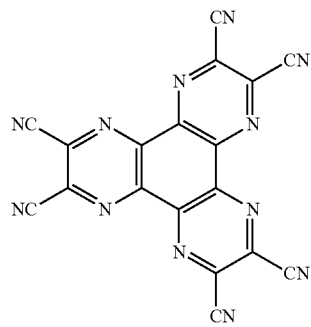

[hexanitrile hexaazatriphenylene]

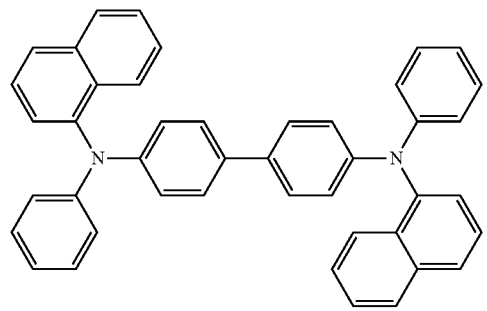

[NPB]

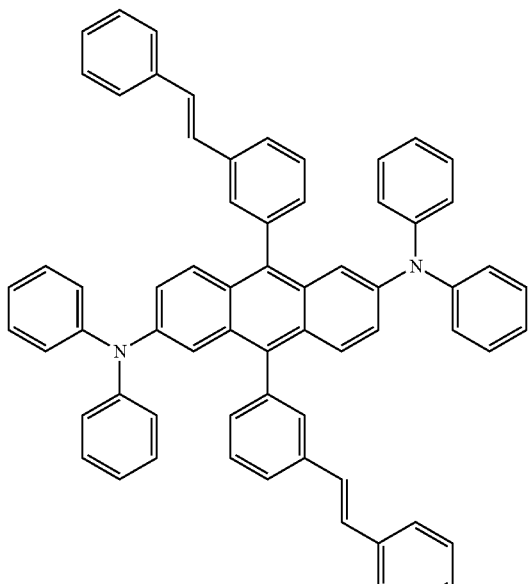

[D1]

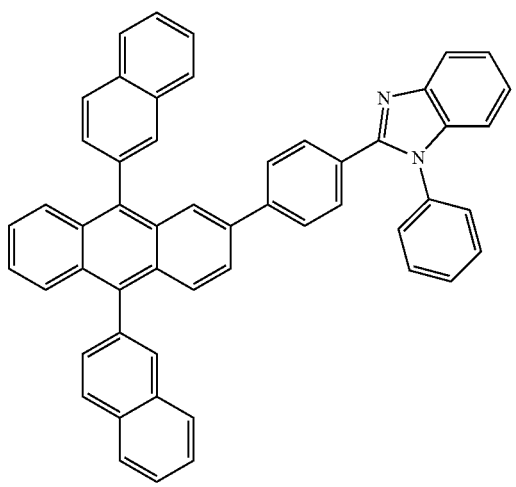

[E1]

Examples 1-2 to 1-5

The organic light emitting device was manufactured by using the same method as Example 1-1, except that the compounds 1-61, 1-6, 1-7 or 1-14 described in the following Table 7 were deposited instead of the compound 1-18. In the above process, the deposition speed of the organic substance was maintained at 1 Å/sec, that of lithium fluoride was maintained at 0.2 Å/sec, and that of aluminum was maintained at 3 to 7 Å/sec. Properties of the manufactured organic light emitting device were evaluated, and the results are described in the following Table 7.

Comparative Example 1-1

The organic light emitting device was manufactured by using the same method as Example 1-1, except that the following compound H1 was used instead of the compound 1-18, properties thereof were evaluated, and the results thereof are described in the following Table 7.

TABLE 7

[H1]

| Example 50 mA/cm² | Host material | Dopant material | Driving voltage (V) | Current efficiency (cd/A) | Color coordinate (x, y) |
|---|---|---|---|---|---|
| Example 1-1 | 1-18 | D1 | 7.40 | 22.42 | (0.303, 0.655) |
| Example 1-2 | 1-61 | D1 | 7.79 | 24.92 | (0.314, 0.650) |
| Example 1-3 | 1-6 | D1 | 7.86 | 26.74 | (0.314, 0.650) |
| Example 1-4 | 1-7 | D1 | 7.80 | 25.11 | (0.314, 0.650) |
| Example 1-5 | 1-14 | D1 | 8.05 | 23.06 | (0.314, 0.650) |
| Comparative Example 1-1 | H1 | D1 | 8.22 | 22.45 | (0.314, 0.652) |

From the results of Table 7, it can be seen that the organic electronic device comprising the compound according to the present invention has excellent properties in terms of efficiency, driving voltage, and stability.

Examples 2-1 to 2-3

The organic light emitting device was manufactured by using the same method as Example 1-1, except that the compounds 1-6, 1-7 or 1-14 described in the following Table 8 were used instead of the compound 1-18 as the host material and the following Formula D2 was used as the dopant in Example 1-1.

Comparative Example 2-1

The organic light emitting device was manufactured by using the same method as Example 1-1, except that the following Formula H2 was used instead of the compound 1-18 as the host material and the following Formula D2 was used as the dopant in Example 1-1.

TABLE 8

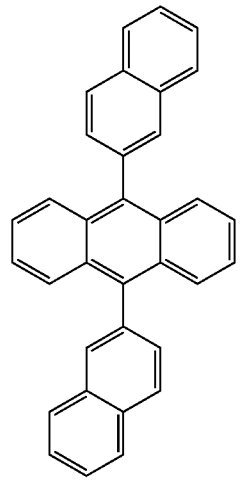 [SMILES: c1ccc2cc(-c3c4ccccc4c(-c4ccc5ccccc5c4)c4ccccc34)ccc2c1]

[H2]

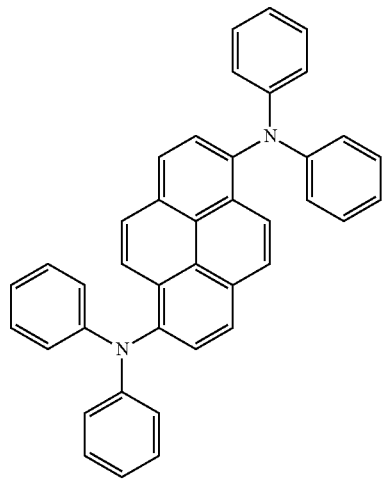 [SMILES: c1ccc(N(c2ccccc2)c2ccc3ccc4c(N(c5ccccc5)c5ccccc5)ccc5ccc2c3c54)cc1]

[D2]

| Example 50 mA/cm² | Host material | Dopant material | Driving voltage (V) | Current efficiency (cd/A) | Color coordinate (x, y) |
|---|---|---|---|---|---|
| Example 2-1 | 1-6 | D2 | 6.2 | 5.3 | (0.134, 0.177) |
| Example 2-2 | 1-7 | D2 | 6.1 | 5.6 | (0.134, 0.178) |
| Example 2-3 | 1-14 | D2 | 6.3 | 5.5 | (0.134, 0.179) |
| Comparative Example 2-1 | H2 | D2 | 6.9 | 5.2 | (0.134, 0.187) |

From the results of Table 8, it can be seen that the organic electronic device comprising the compound according to the present invention has excellent properties in terms of efficiency, driving voltage, and stability.

The invention claimed is:

1. A compound that is represented by the following Formula 1:

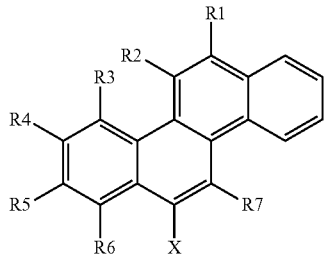

[Formula 1]

wherein
R1 is selected from the group consisting of substituted or unsubstituted $C_1$~$C_{40}$ alkyl group; substituted or unsubstituted $C_3$~$C_{40}$ cycloalkyl group; substituted or unsubstituted $C_2$~$C_{40}$ heterocycloalkyl group; substituted or unsubstituted $C_2$~$C_{40}$ alkenyl group; substituted or unsubstituted amino group; substituted or unsubstituted $C_6$~$C_{40}$ aryl group; substituted or unsubstituted $C_3$~$C_{40}$ heteroaryl group that comprises O or S as a heteroatom; and substituted or unsubstituted $C_3$~$C_{40}$ heteroarylamine group that comprises O or S as a heteroatom, R2 is selected from the group consisting of substituted or unsubstituted $C_1$~$C_{40}$ alkyl group; substituted or unsubstituted $C_3$~$C_{40}$ cycloalkyl group; substituted or unsubstituted $C_3$~$C_{40}$ heterocycloalkyl group; substituted or unsubstituted $C_2$~$C_{40}$ alkenyl group; substituted or unsubstituted $C_1$~$C_{40}$ alkoxy group; substituted or unsubstituted amino group; substituted or unsubstituted $C_6$~$C_{40}$ aryl group; substituted or unsubstituted $C_3$~$C_{40}$ heteroaryl group that comprises O or S as a heteroatom; substituted or unsubstituted $C_5$~$C_{40}$ arylamine group; and substituted or unsubstituted $C_3$~$C_{40}$ heteroarylamine group that comprises O or S as a heteroatom, R3 to R4 and R6 to R7 are each independently selected from the group consisting of hydrogen; substituted or unsubstituted $C_1$~$C_{40}$ alkyl group; substituted or unsubstituted $C_3$~$C_{40}$ cycloalkyl group; substituted or unsubstituted $C_2$~$C_{40}$ heterocycloalkyl group that comprises O, N, or S as a heteroatom; substituted or unsubstituted $C_2$~$C_{40}$ alkenyl group; substituted or unsubstituted $C_1$~$C_{40}$ alkoxy group; substituted or unsubstituted amino group; substituted or unsubstituted $C_6$~$C_{40}$ aryl group; substituted or unsubstituted $C_3$~$C_{40}$ heteroaryl group that comprises O, N, or S as a heteroatom; substituted or unsubstituted $C_5$~$C_{40}$ arylamine group; and substituted or unsubstituted $C_3$~$C_{40}$ heteroarylamine group that comprises O, N, or S as a heteroatom, and may form an aliphatic, aromatic, heteroaliphatic or heteroaromatic condensate ring or a spiro bond in conjunction with an adjacent group, R5 is selected from the group consisting of hydrogen; substituted or unsubstituted $C_1$~$C_{40}$ alkyl group; substituted or unsubstituted $C_3$~$C_{40}$ cycloalkyl group; substituted or unsubstituted $C_2$~$C_{40}$ heterocycloalkyl group that comprises O, N, or S as a heteroatom; substituted or unsubstituted $C_2$~$C_{40}$ alkenyl group; substituted or unsubstituted amino group; substituted or unsubstituted $C_6$~$C_{40}$ aryl group; substituted or unsubstituted $C_3$~$C_{40}$ heteroaryl group that comprises O, N, or S as a heteroatom; substituted or unsubstituted $C_5$~$C_{40}$ arylamine group; and substituted or unsubstituted $C_3$~$C_{40}$ heteroarylamine group that comprises O, N, or S as a heteroatom, and may form an aliphatic, aromatic, heteroaliphatic or heteroaromatic condensate ring or a spiro bond in conjunction with an adjacent group, X is selected from the group consisting of hydrogen; substituted or unsubstituted $C_1$~$C_{40}$ alkyl group; substituted or unsubstituted $C_3$~$C_{40}$ cycloalkyl group; substituted or unsubstituted $C_2$~$C_{40}$ heterocycloalkyl group that comprises O, N, or S as a heteroatom; substituted or unsubstituted $C_2$~$C_{40}$ alkenyl group; substituted or unsubstituted $C_3$~$C_{40}$ heteroaryl group that comprises O or S as a heteroatom; and substituted or unsubstituted $C_3$~$C_{40}$ heteroarylamine group that comprises O or S as a heteroatom, and may form an aliphatic, aromatic, heteroaliphatic or heteroaromatic condensate ring or a spiro bond in conjunction with an adjacent group, and all of R3 to R7, and X are not hydrogen.

2. The compound according to claim 1, wherein in R2 to R4 and R6 to R7, in the case of when alkyl group, cycloalkyl group, heterocycloalkyl group, alkenyl group, alkoxy group, amino group, aryl group, heteroaryl group, arylamine group and heteroarylamine group are substituted by the other functional group, they are substituted by one or more groups selected from the group consisting of halogen, deuterium, amino group, nitrile group, nitro group, $C_1$~$C_{40}$ alkyl group, $C_2$~$C_{40}$ alkenyl group, $C_1$~$C_{40}$ alkoxy group, $C_3$~$C_{40}$ cycloalkyl group, $C_2$~$C_{40}$ heterocycloalkyl group that comprises O, N, or S as a heteroatom, $C_6$~$C_{40}$ aryl group and $C_3$~$C_{40}$ heteroaryl group that comprises O, N, or S as a heteroatom, in R5, in the case of when alkyl group, cycloalkyl group, heterocycloalkyl group, alkenyl group, amino group, aryl group, heteroaryl group, arylamine group and heteroarylamine group are substituted by the other functional group, they are substituted by one or more groups selected from the group consisting of halogen, deuterium, amino group, nitrile group, nitro group, $C_1$~$C_{40}$ alkyl group, $C_2$~$C_{40}$ alkenyl group, $C_1$~$C_{40}$ alkoxy group, $C_3$~$C_{40}$ cycloalkyl group, $C_2$~$C_{40}$ heterocycloalkyl group that comprises O, N, or S as a heteroatom, $C_6$~$C_{40}$ aryl group and $C_3$~$C_{40}$ heteroaryl group that comprises O, N, or S as a heteroatom, and in R1 and X, in the case of when alkyl group, cycloalkyl group, heterocycloalkyl group, alkenyl group, amino group, aryl group, heteroaryl group and heteroarylamine group are substituted by another functional group, they are substituted by one or more groups that are selected from the group consisting of halogen, deuterium, nitrile group, nitro group, $C_1$~$C_{40}$ alkyl group, $C_2$~$C_{40}$ alkenyl group, $C_1$~$C_{40}$ alkoxy group, $C_3$~$C_{40}$ cycloalkyl group, $C_2$~$C_{40}$ heterocycloalkyl group that comprises O, N or S as a heteroatom, $C_6$~$C_{40}$ aryl group and $C_3$~$C_{40}$ heteroaryl group that comprises O or S as a heteroatom.

3. The compound according to claim 1, wherein R1 is selected from the group consisting of substituted or unsubstituted $C_6$~$C_{40}$ aryl group; substituted or unsubstituted $C_3$~$C_{40}$ heteroaryl group that comprises O or S as a heteroatom; and substituted or unsubstituted $C_3$~$C_{40}$ heteroarylamine group that comprises O or S as a heteroatom, R2 is selected from the group consisting of substituted or unsubstituted $C_6$~$C_{40}$ aryl group; substituted or unsubstituted $C_3$~$C_{40}$ heteroaryl group that comprises O, N or S as a heteroatom; substituted or unsubstituted $C_5$~$C_{40}$ arylamine group; and substituted or unsubstituted $C_3$~$C_{40}$ heteroarylamine group that comprises O, N or S as a heteroatom.

4. The compound according to claim 1, wherein R1 is selected from the group consisting of $C_6\sim C_{20}$ aryl group; $C_6\sim C_{20}$ aryl group that is substituted by $C_6\sim C_{40}$ aryl group or $C_3\sim C_{40}$ heteroaryl group that comprises O or S as a heteroatom; and $C_3\sim C_{20}$ heteroaryl group that is substituted by $C_6\sim C_{20}$ aryl group and comprises O or S as a heteroatom, and R2 is selected from the group consisting of $C_6\sim C_{20}$ aryl group; $C_6\sim C_{20}$ aryl group that is substituted by $C_6\sim C_{40}$ aryl group, $C_3\sim C_{40}$ heteroaryl group that comprises O, N or S as a heteroatom or $C_5\sim C_{40}$ arylamine group; $C_3\sim C_{20}$ heteroaryl group that is substituted by $C_6\sim C_{20}$ aryl group and comprises O, N or S as a heteroatom; and $C_6\sim C_{20}$ arylamine group.

5. The compound according to claim 1, wherein R1 is selected from the group consisting of the substituent groups that are represented by the following structural formulas:

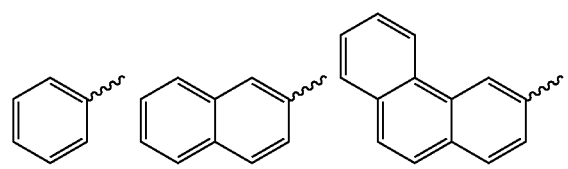

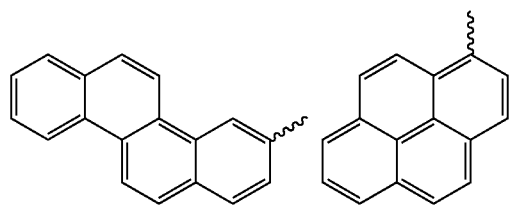

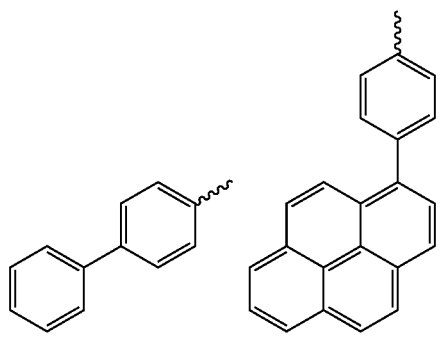

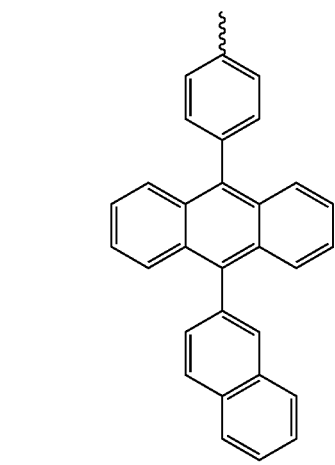

-continued

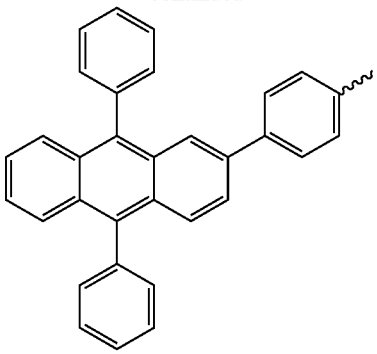

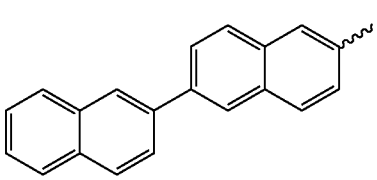

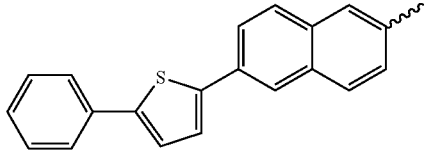

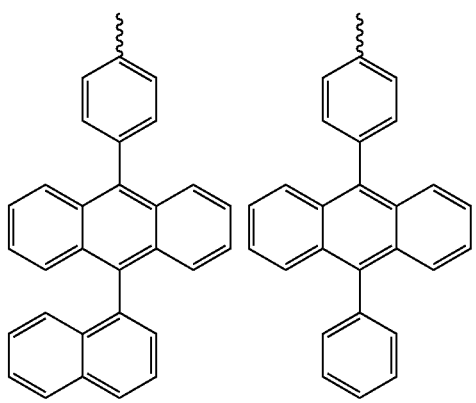

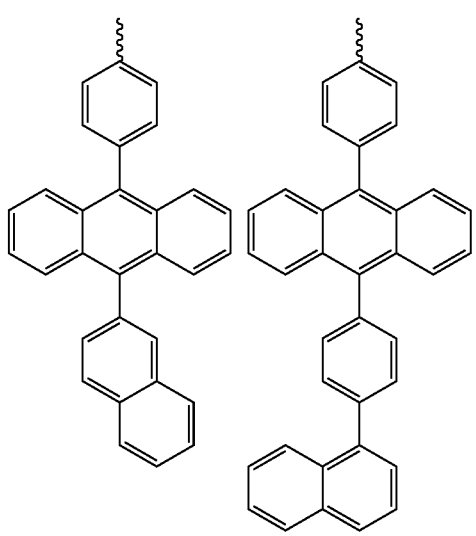

201
-continued
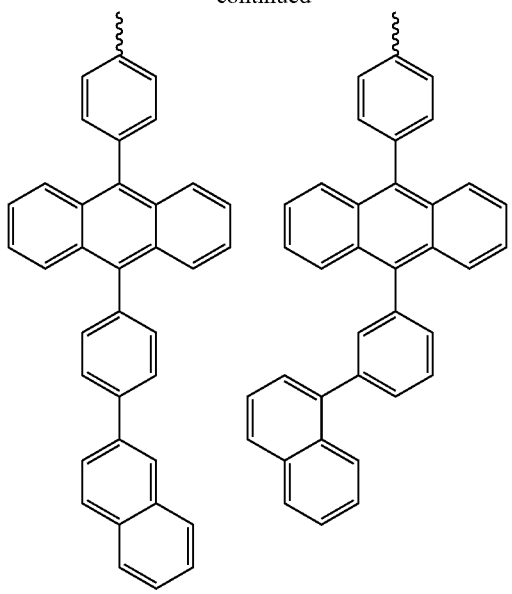
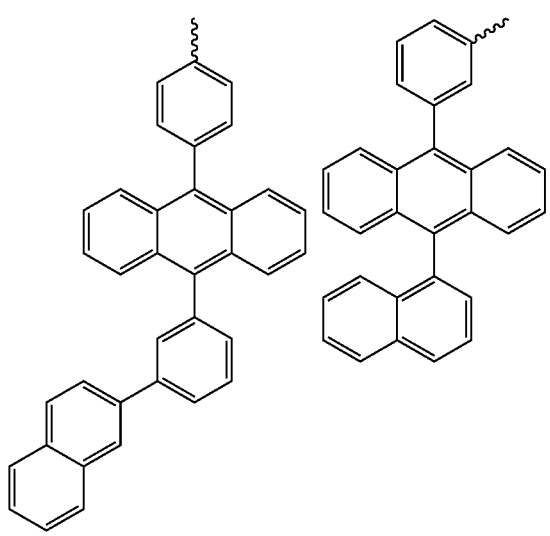
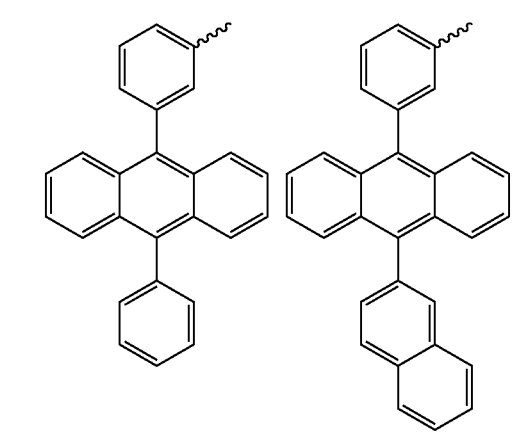
202
-continued
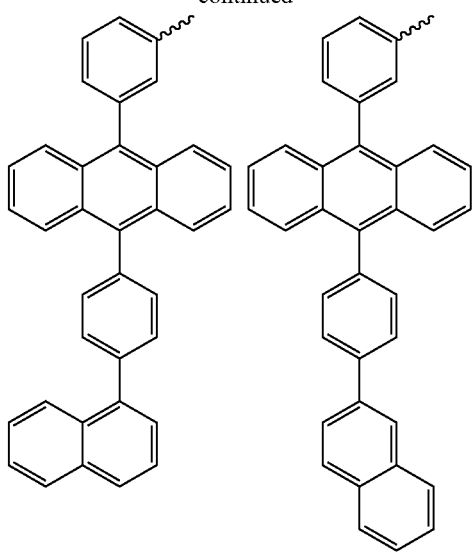
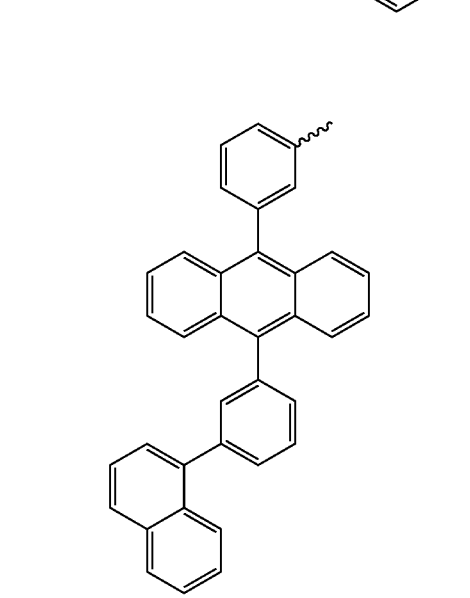
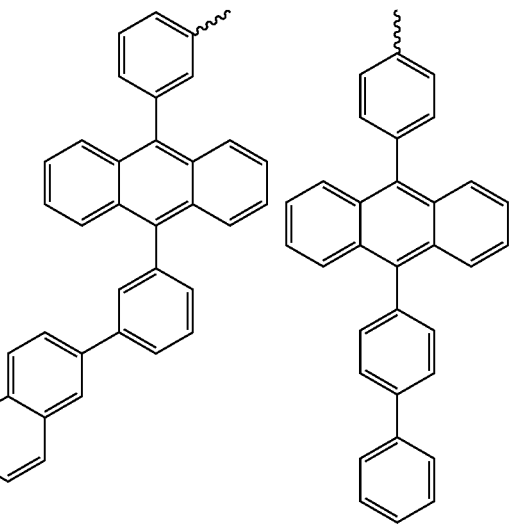

203
-continued
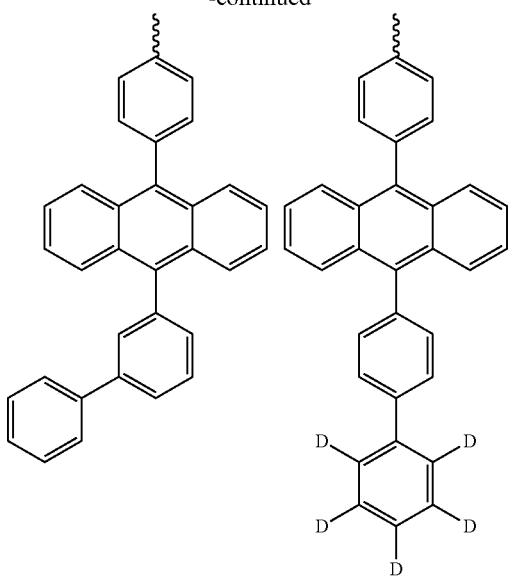
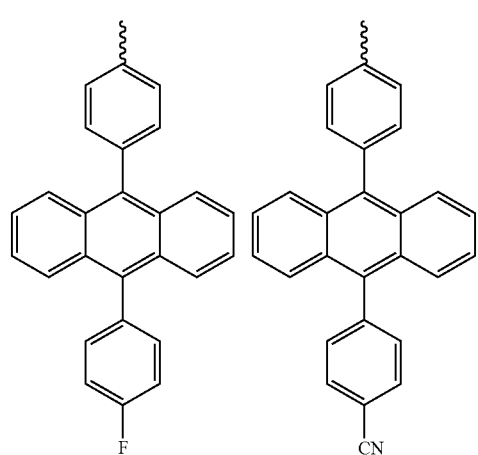
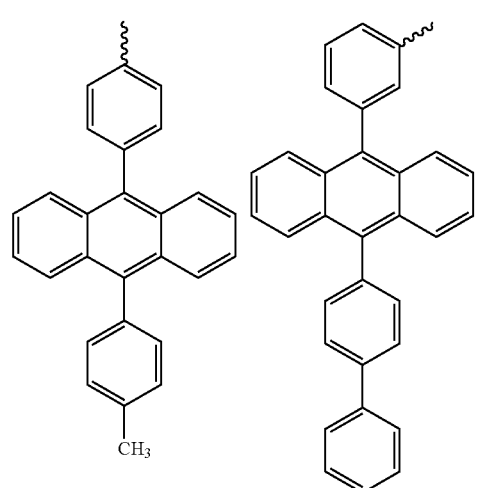
204
-continued
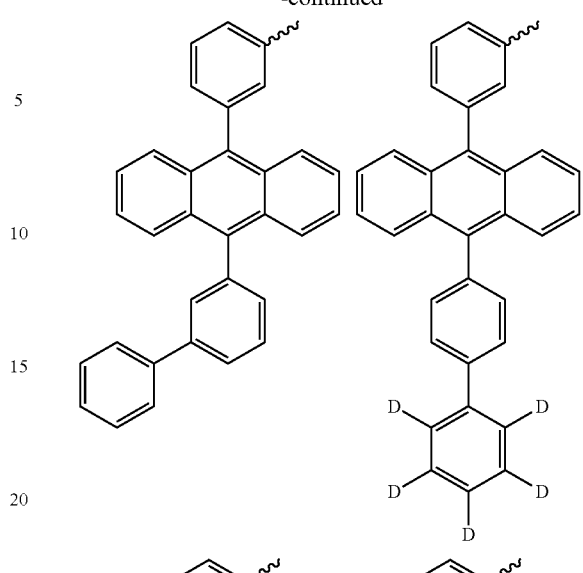
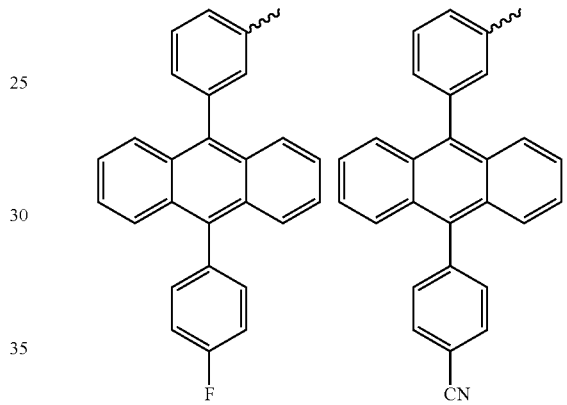
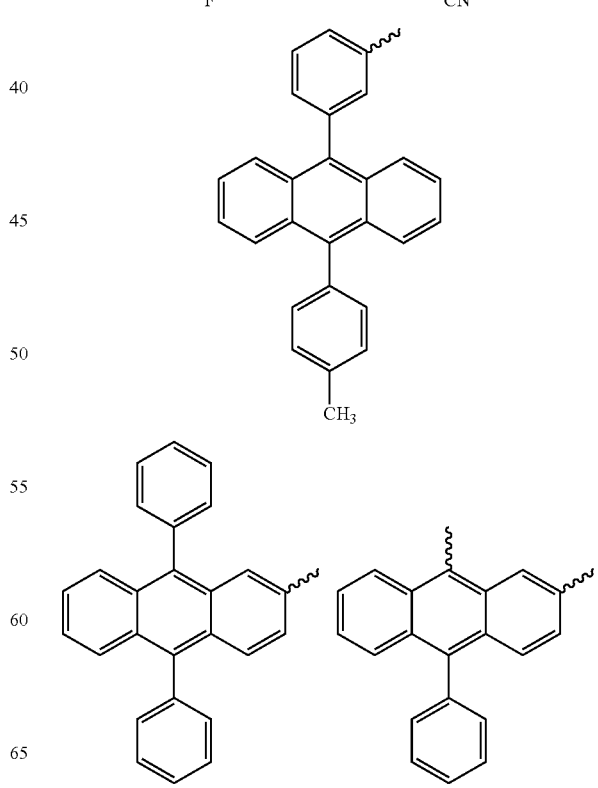

205
-continued
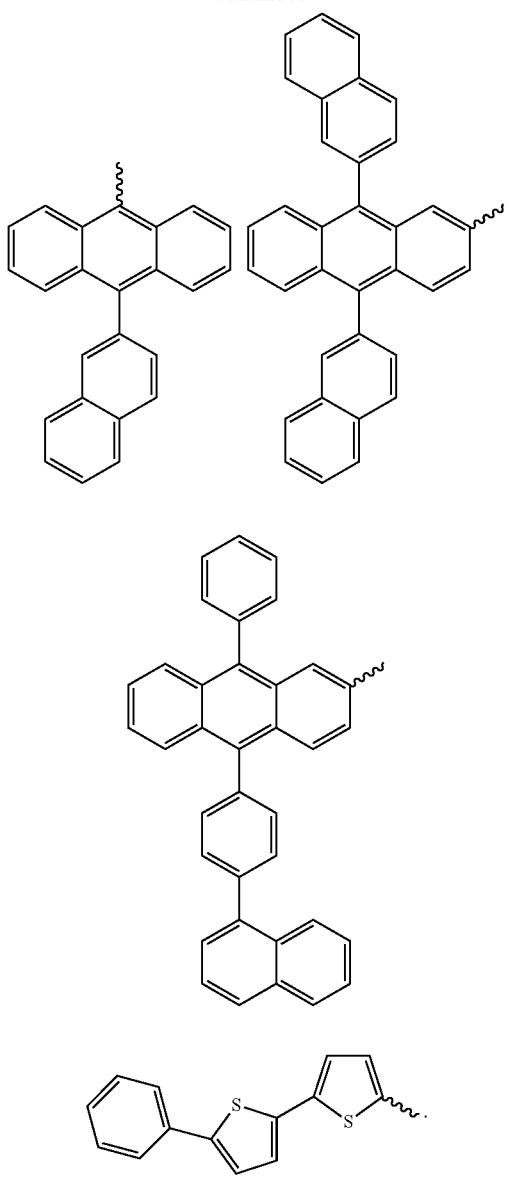
6. The compound according to claim 1, wherein R2 is selected from the group consisting of the substituent groups that are represented by the following structural formulas:
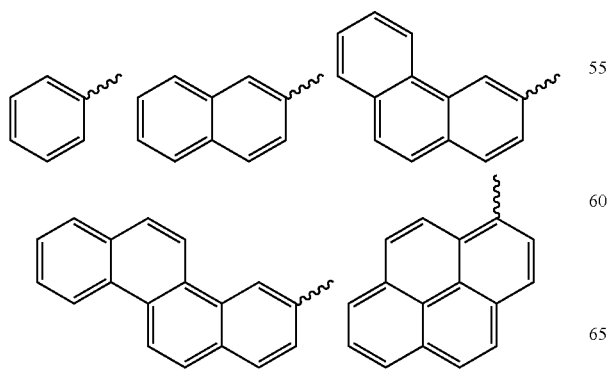
206
-continued
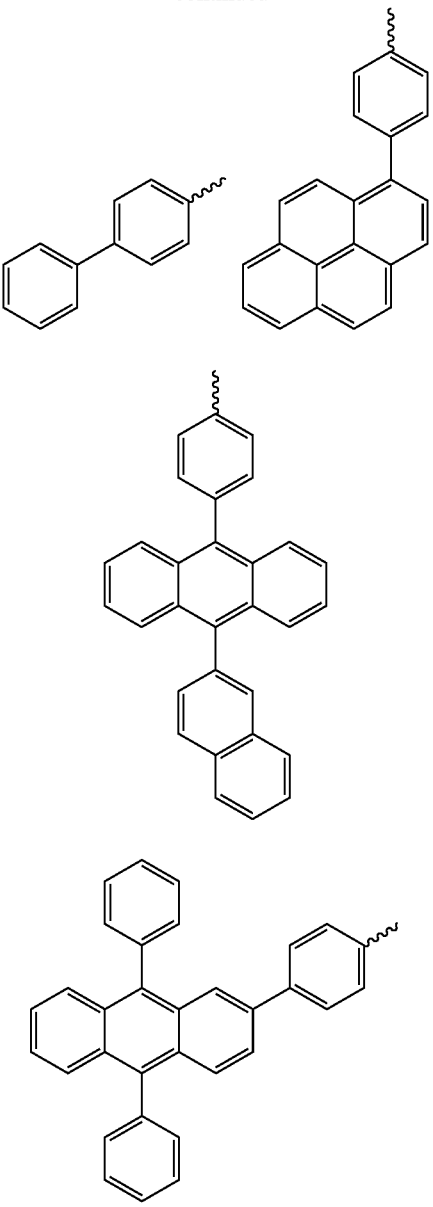
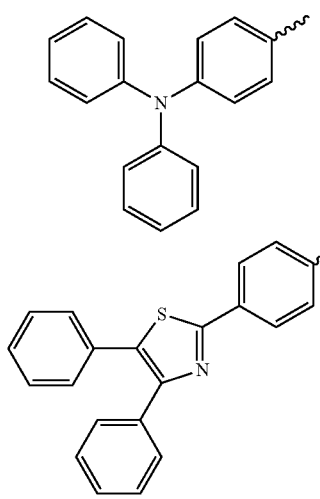

207
-continued
208
-continued
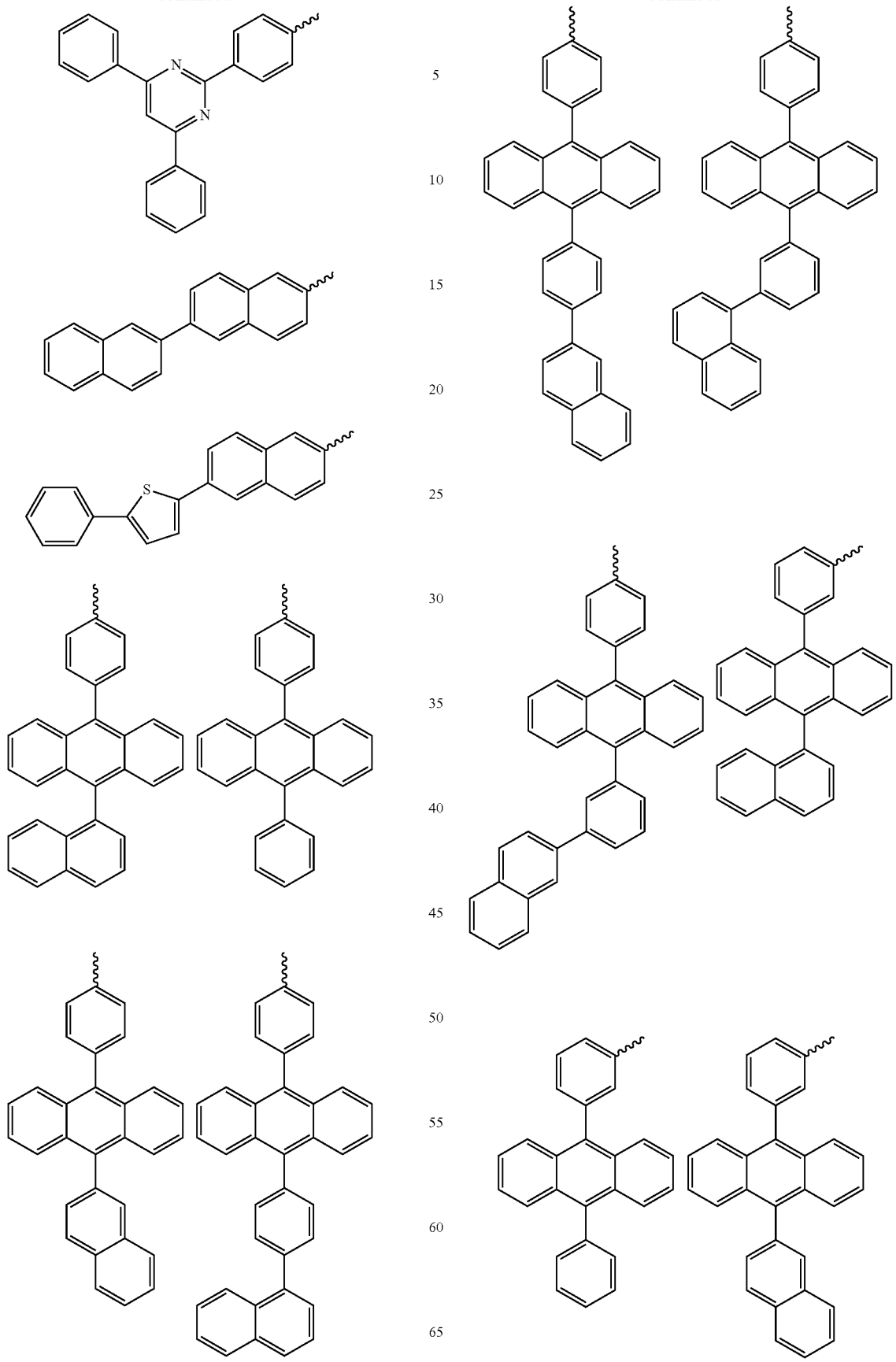

209
-continued
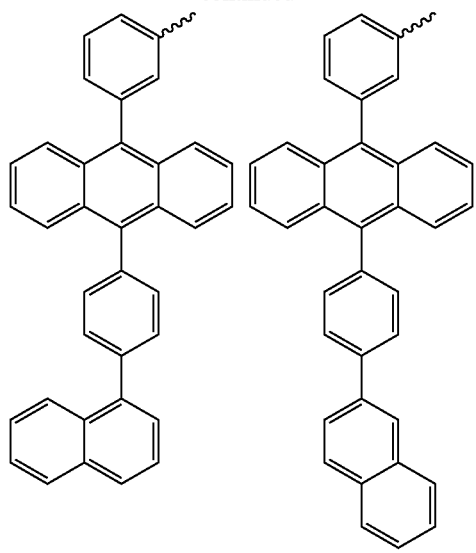
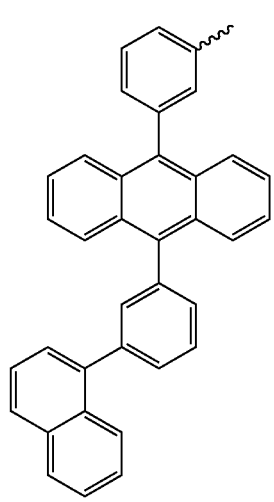
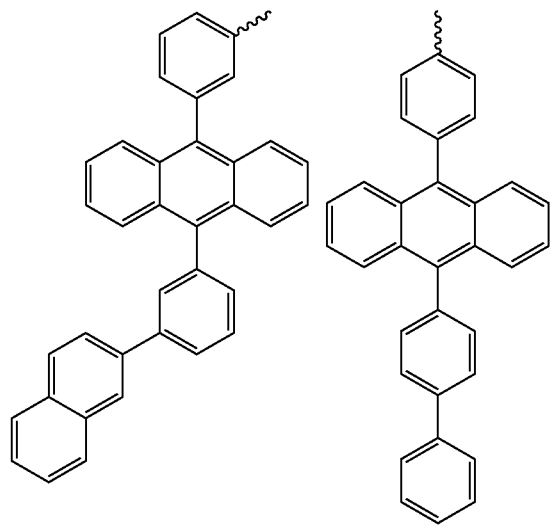
210
-continued
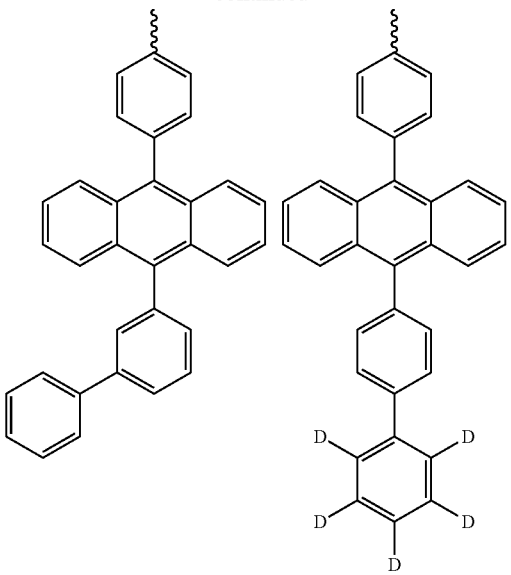
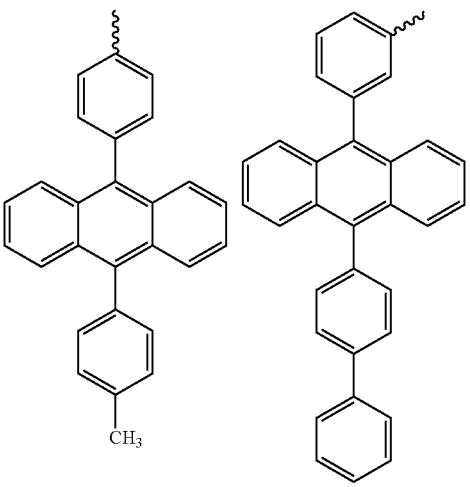

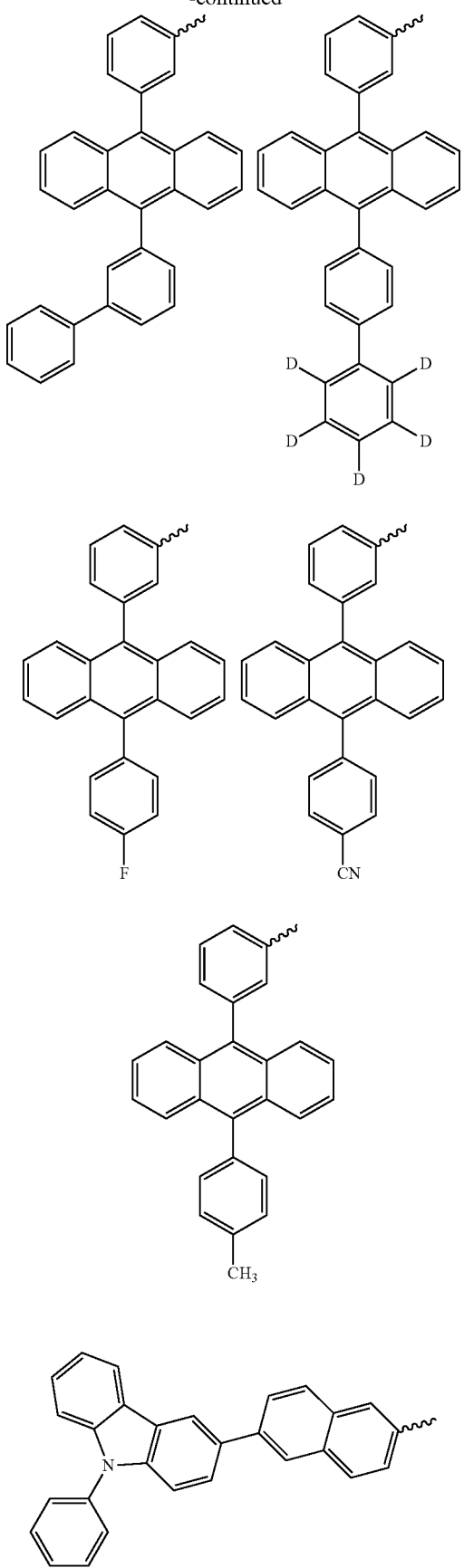
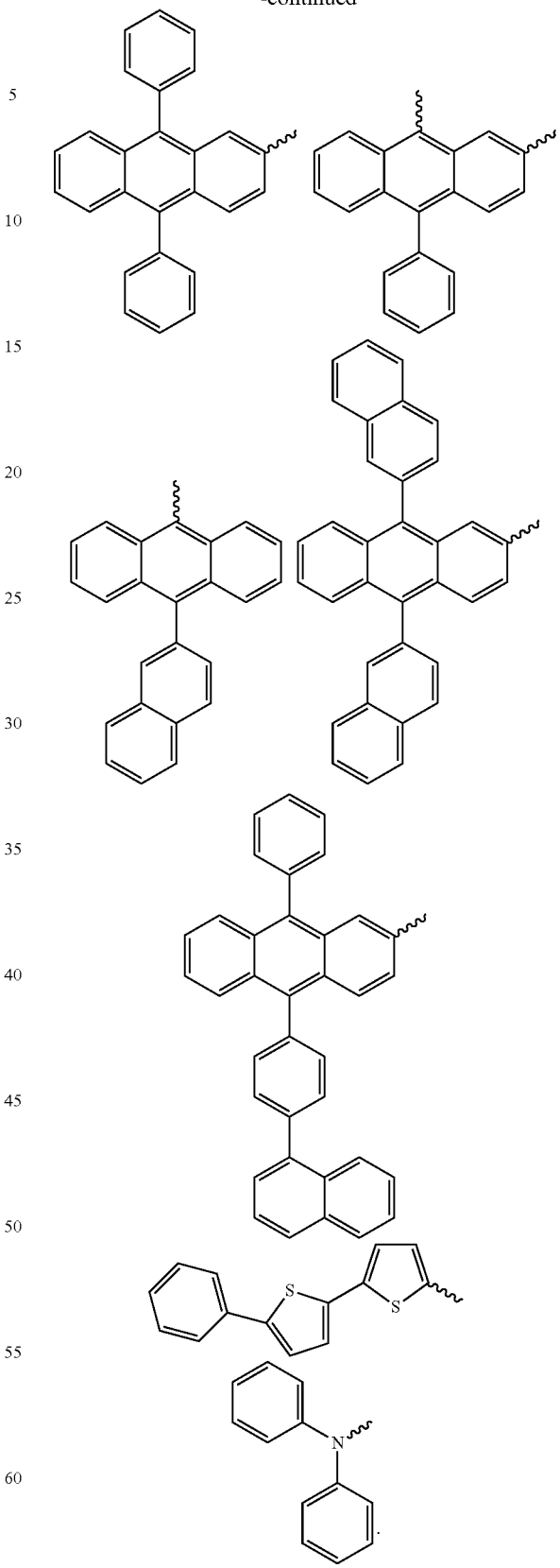
7. The compound according to claim 1, wherein R3 to R7 are hydrogen.

8. The compound according to claim 7, wherein X is selected from the group consisting of substituted or unsubstituted $C_3\sim C_{40}$ heteroaryl group that comprises O or S as a heteroatom; and substituted or unsubstituted $C_3\sim C_{40}$ heteroarylamine group that comprises O or S as a heteroatom.

9. The compound according to claim 7, wherein X is $C_3\sim C_{20}$ heteroaryl group that is substituted by $C_6\sim C_{20}$ aryl group and comprises O or S as a heteroatom.

10. The compound according to claim 7, wherein X is selected from the group consisting of the substituent groups that are represented by the following structural formula:

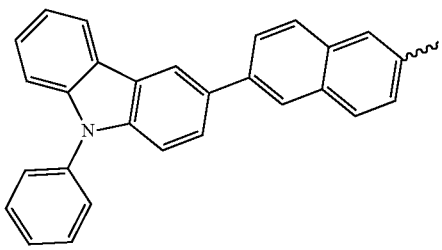

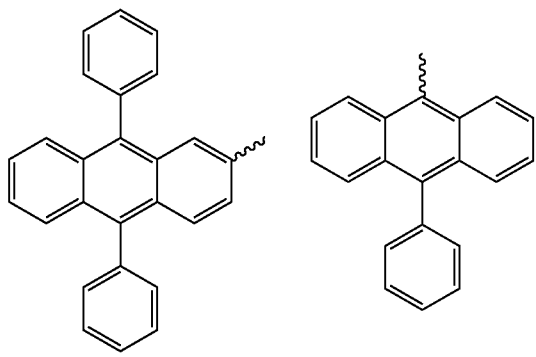

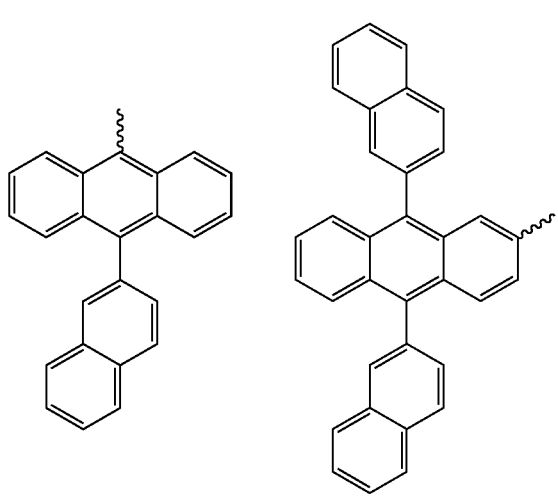

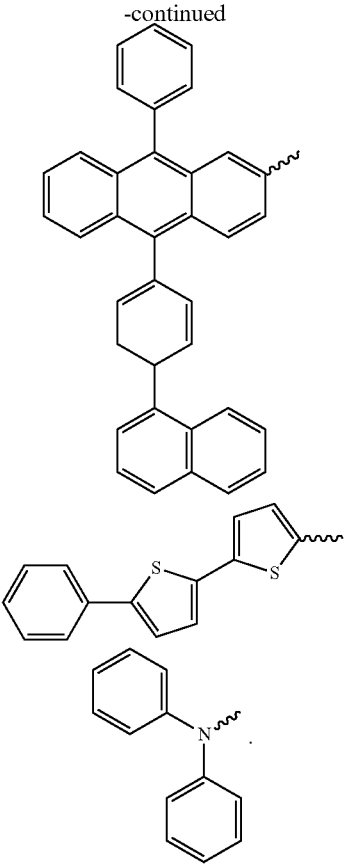

11. The compound according to claim 1, wherein four of R3 to R7 and X are hydrogen.

12. The compound according to claim 11, wherein the substituent group except for hydrogen among R3 to R7 is selected from the group consisting of substituted or unsubstituted $C_6\sim C_{40}$ aryl group; substituted or unsubstituted $C_3\sim C_{40}$ heteroaryl group that comprises O, N or S as a heteroatom; substituted or unsubstituted $C_5\sim C_{40}$ arylamine group; and substituted or unsubstituted $C_3\sim C_{40}$ heteroarylamine group that comprises O, N or S as a heteroatom.

13. The compound according to claim 11, wherein the substituent group except for hydrogen among R3 to R7 is selected from the group consisting of $C_6\sim C_{20}$ aryl group; $C_6\sim C_{20}$ aryl group that is substituted by $C_6\sim C_{40}$ aryl group, $C_3\sim C_{40}$ heteroaryl group that comprises O, N or S as a heteroatom or $C_5\sim C_{40}$ arylamine group; $C_3\sim C_{20}$ heteroaryl group that is substituted by $C_6\sim C_{20}$ aryl group and comprises O, N or S as a heteroatom; and $C_6\sim C_{20}$ arylamine group.

14. The compound according to claim 11, wherein the substituent group except for hydrogen among R3 to R7 is selected from the group consisting of the substituent groups that are represented by the following structural formulas:

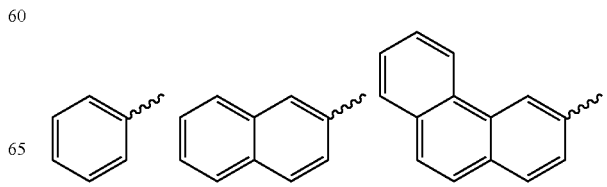

215
-continued
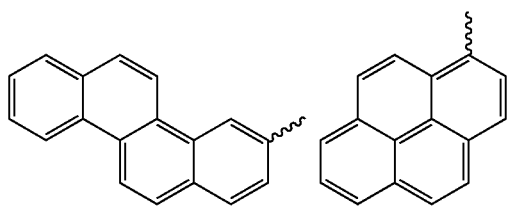
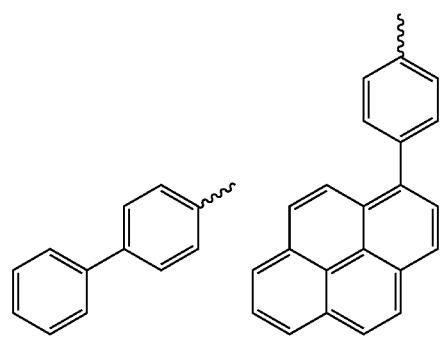
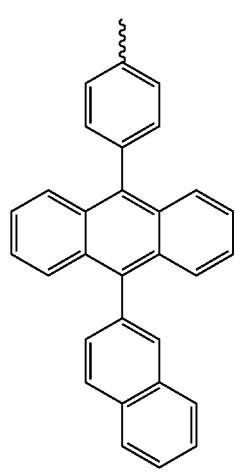
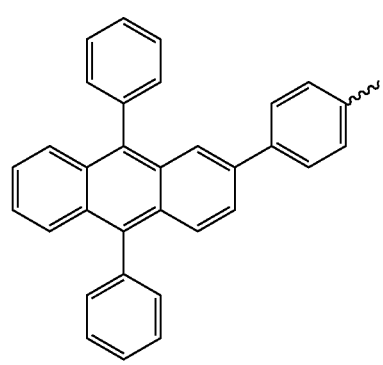
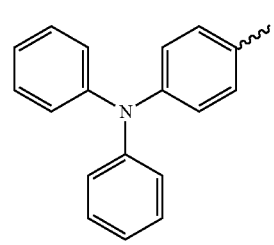
216
-continued
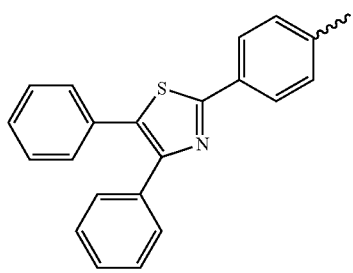
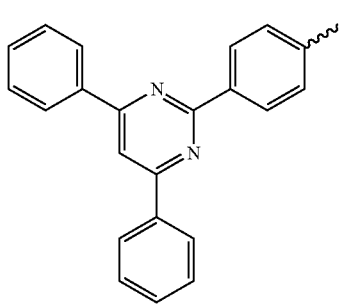
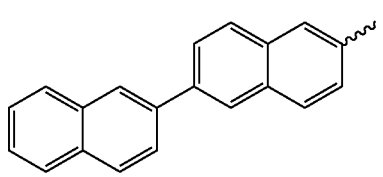
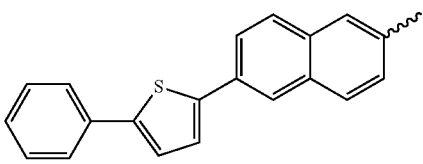
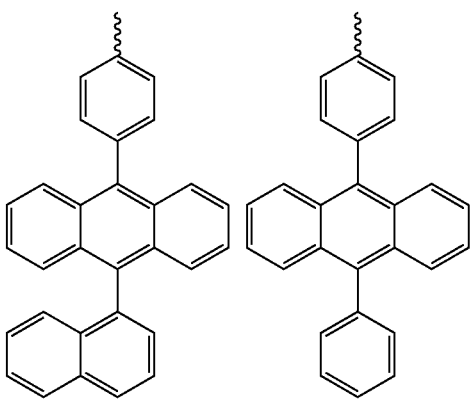

217
-continued
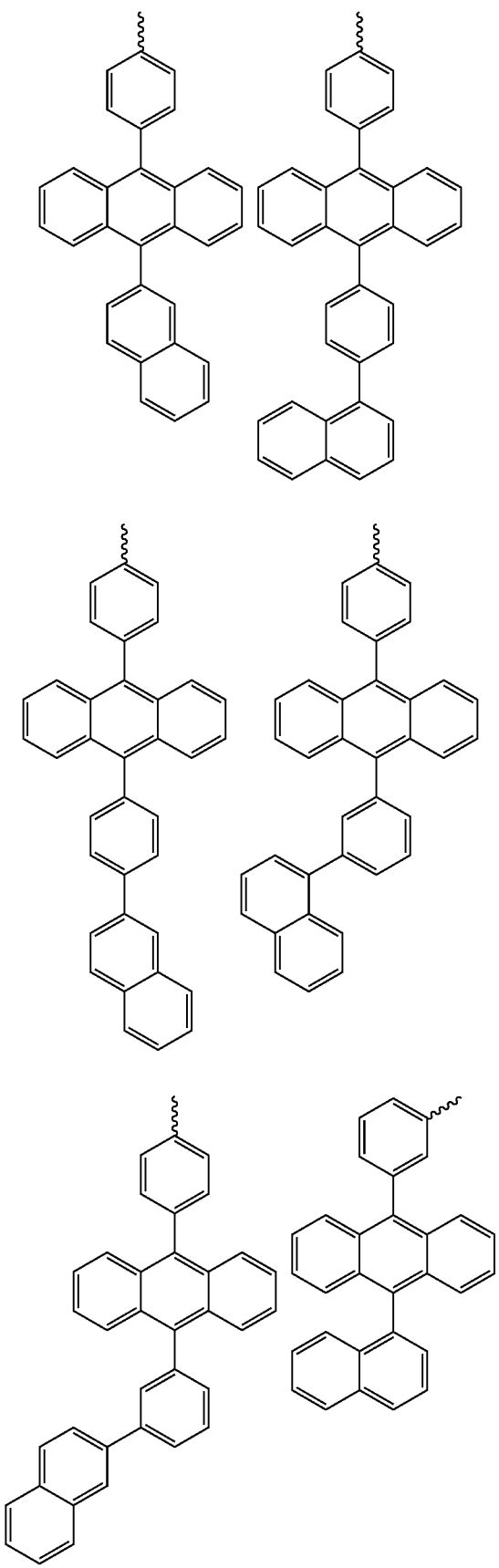
218
-continued
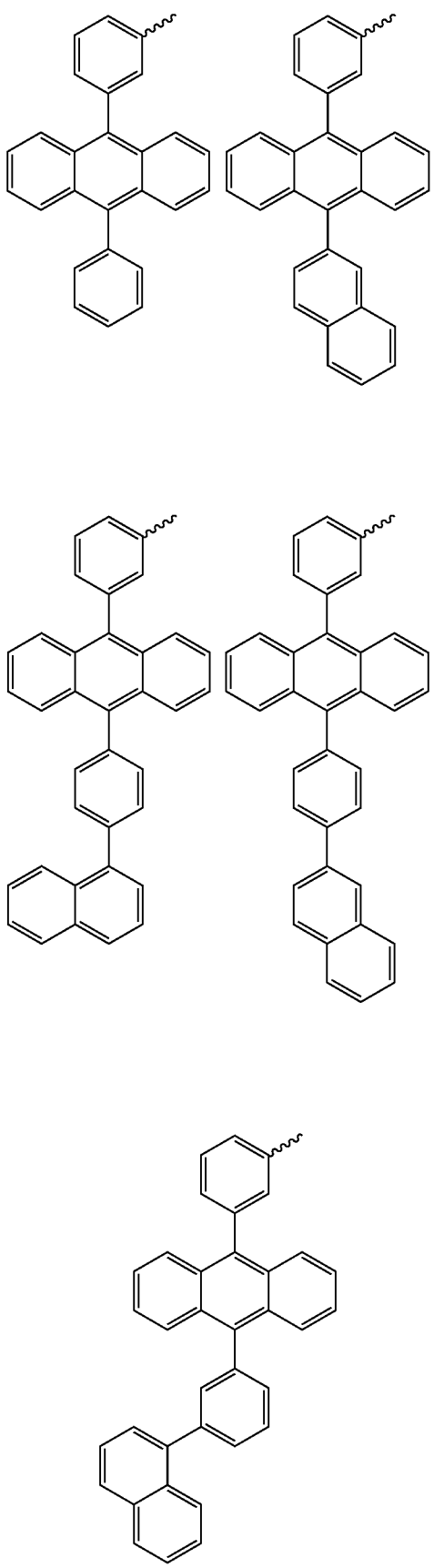

219
-continued
220
-continued
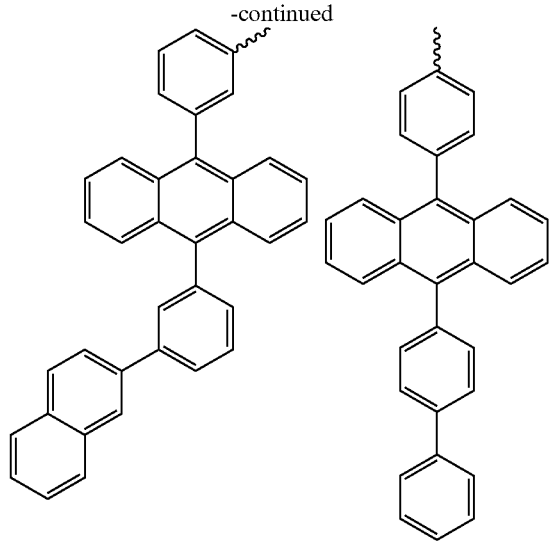
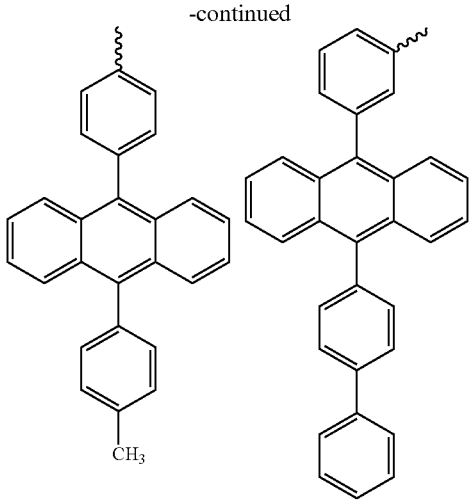
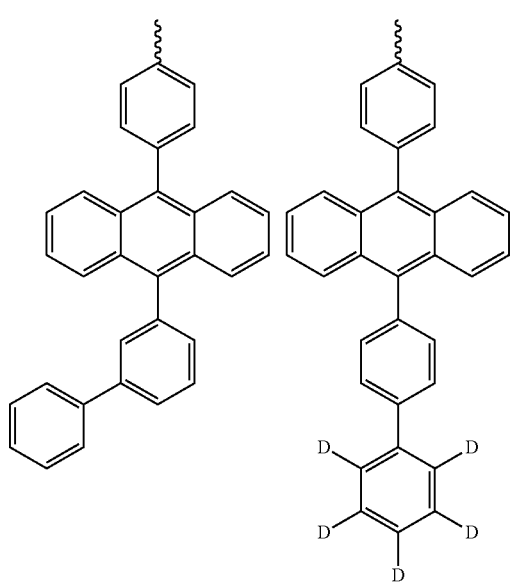
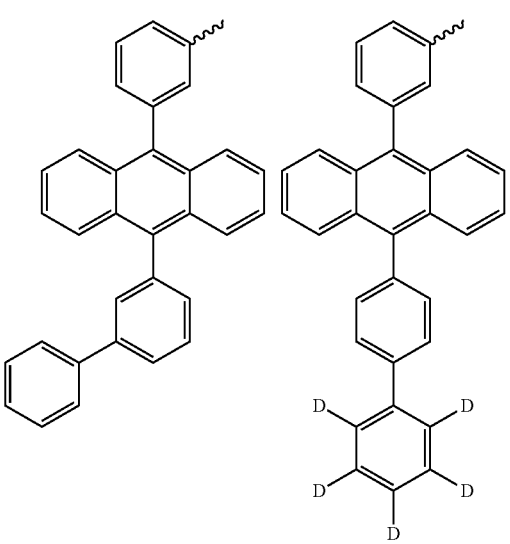
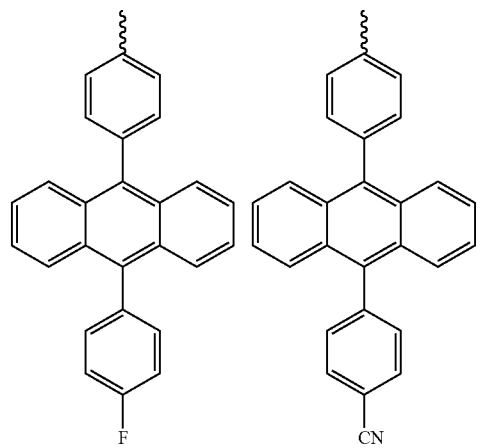
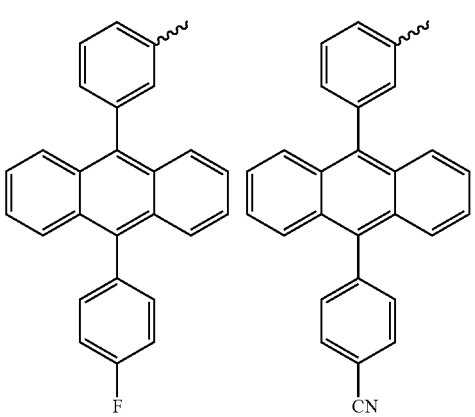

221
-continued

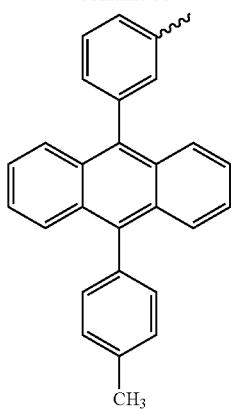

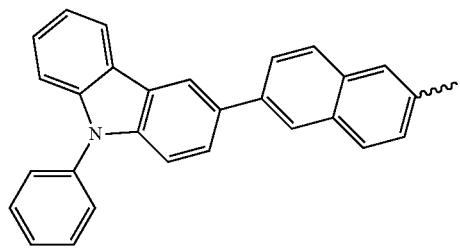

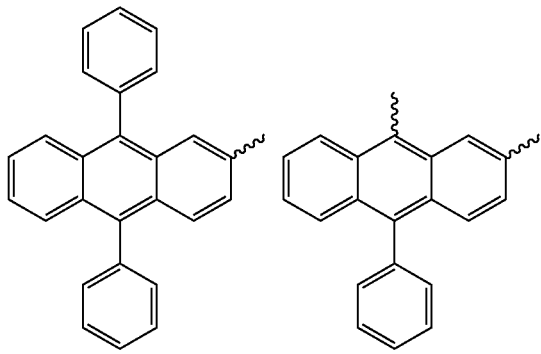

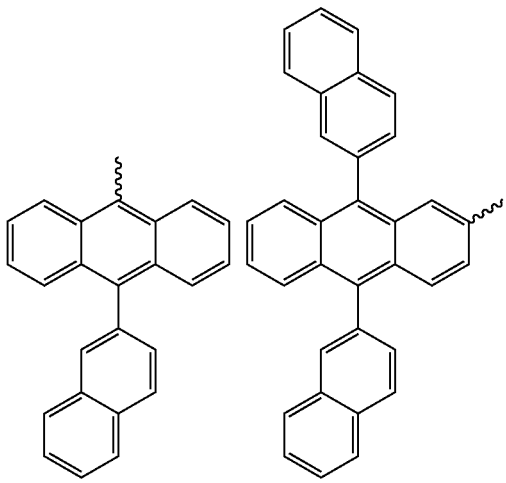

222
-continued

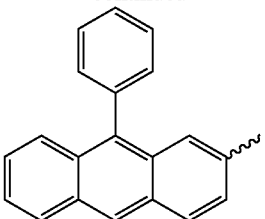

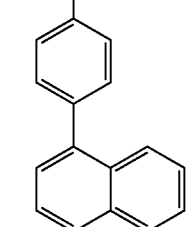

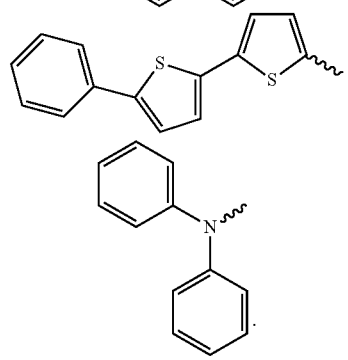

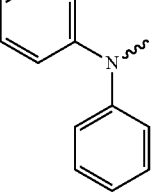

15. The compound according to claim 1, wherein R1 is selected from the group consisting of $C_6$~$C_{20}$ aryl group; $C_6$~$C_{20}$ aryl group that is substituted by $C_6$~$C_{40}$ aryl group or $C_3$~$C_{40}$ heteroaryl group that comprises O or S as a heteroatom; and $C_3$~$C_{20}$ heteroaryl group that is substituted by $C_6$~$C_{20}$ aryl group and comprises O or S as a heteroatom; R2 is selected from the group consisting of $C_6$~$C_{20}$ aryl group; $C_6$~$C_{20}$ aryl group that is substituted by $C_6$~$C_{40}$ aryl group, $C_3$~$C_{40}$ heteroaryl group that comprises O, N or S as a heteroatom or $C_5$~$C_{40}$ arylamine group; $C_3$~$C_{20}$ heteroaryl group that is substituted by $C_6$~$C_{20}$ aryl group and comprises O, N or S as a heteroatom; and $C_6$~$C_{20}$ arylamine group;

R5 is selected from the group consisting of $C_6$~$C_{20}$ aryl group; $C_6$~$C_{20}$ aryl group that is substituted by $C_6$~$C_{40}$ aryl group, $C_3$~$C_{40}$ heteroaryl group that comprises O, N or S as a heteroatom or $C_5$~$C_{40}$ arylamine group; $C_3$~$C_{20}$ heteroaryl group that is substituted by $C_6$~$C_{20}$ aryl group and comprises O, N or S as a heteroatom; and $C_6$~$C_{20}$ arylamine group, and R3, R4, R6, R7 and X are hydrogen.

16. An organic electronic device which comprises a first electrode, a second electrode, and one or more organic material layers that are disposed between the first electrode and the second electrode, wherein one or more layers of the organic material layers comprise the compound according to claim 1.

17. The organic electronic device according to claim 16, wherein the organic material layer comprises at least one layer of a hole injection layer and a hole transport layer, and at least one layer comprises the compound that is represented by Formula 1.

18. The organic electronic device according to claim 16, wherein the organic material layer comprises a light emitting layer, and the light emitting layer comprises the compound that is represented by Formula 1.

19. The organic electronic device according to claim 16, wherein the organic material layer comprises an electron transport layer, and the electron transport layer comprises the compound that is represented by Formula 1.

20. The organic electronic device according to claim 16, wherein the organic electronic device is selected from the group consisting of an organic light emitting device, an organic solar cell, an organic photoconductor (OPC), and an organic transistor.

* * * * *